United States Patent [19]
Wissner et al.

[11] Patent Number: 5,231,091
[45] Date of Patent: Jul. 27, 1993

[54] BIS-ARYLPHOSPHATE ESTER ANTAGONISTS OF PLATELET ACTIVATING FACTOR

[75] Inventors: Allan Wissner, Ardsley; Kenneth Green, Yorktown Heights, both of N.Y.; Robert E. Schaub, Upper Saddle River, N.J.

[73] Assignee: American Cyanamid Company, Stamford, Conn.

[21] Appl. No.: 923,412

[22] Filed: Jul. 31, 1992

Related U.S. Application Data

[62] Division of Ser. No. 599,580, Oct. 18, 1990, Pat. No. 5,147,864, which is a division of Ser. No. 286,193, Dec. 19, 1988, Pat. No. 4,983,592.

[51] Int. Cl.⁵ .................. A61K 41/425; A61K 41/415
[52] U.S. Cl. ........................................................ 514/92
[58] Field of Search ........................................ 514/92

[56] References Cited

U.S. PATENT DOCUMENTS

| | | | |
|---|---|---|---|
| 4,080,443 | 3/1978 | Malhotra | 514/89 |
| 4,160,828 | 7/1979 | Suder et al. | 514/82 |
| 4,316,896 | 2/1982 | Thorsett | 514/92 |
| 4,456,464 | 6/1984 | Lee et al. | 546/22 |
| 4,762,942 | 8/1988 | Wissner | 558/169 |
| 4,777,163 | 10/1988 | Bosies | 514/92 |
| 4,983,592 | 1/1991 | Wissner | 514/82 |
| 5,128,351 | 7/1992 | Wissner et al. | 548/204 |
| 5,147,580 | 9/1992 | Wissner et al. | 514/82 |

FOREIGN PATENT DOCUMENTS

| | | |
|---|---|---|
| 0178261 | 4/1986 | European Pat. Off. |
| 0374510 | 6/1990 | European Pat. Off. |

*Primary Examiner*—Donald G. Daus
*Attorney, Agent, or Firm*—H. G. Jackson

[57] ABSTRACT

The invention is novel compounds of the formula:

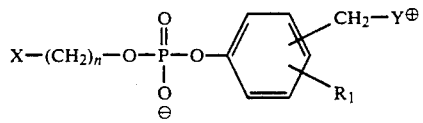

which are antagonists of platelet activating factor.

10 Claims, No Drawings

BIS-ARYLPHOSPHATE ESTER ANTAGONISTS OF PLATELET ACTIVATING FACTOR

This is a divisional of co-pending application Ser. No. 07/599,580, filed on Oct. 18, 1990 now U.S. Pat. No. 5,147,864 which is a divisional of Ser. No. 286,193 filed on Dec. 19, 1988, which is now U.S. Pat. No. 4,983,592.

BACKGROUND OF THE INVENTION

Platelet Activating Factor (PAF), 1-0-hexadecyl/-octadecyl-2-acetyl-sn-glyceryl-3-phosphorylcholine, is an ether lipid produced by a variety of different cell types. Recent studies [Snyder, F., Ann. Rep. Med. Chem., 17, 243 (1982); Pinckard, R.N., et. al., J. Adv. Inflammation Res., 4, 147 (1982); O'Flaherty, J. T., et. al., Clin. Rev. Allergy, 1, 353 (1983); Vargaftig, B. B., et. al., J. Trends. Pharmacol. Sci., 4, 341 (1983)] have shown PAF to be an important mediator of allergic disease. Included among the physiological processes in which PAF is implicated are aggregation of platelets, inflammation, smooth muscle contraction, pain and edema. PAF is implicated in asthma, respiratory distress syndrome, lung edema and other inflammatory and cardiovascular diseases.

The compounds of the present invention have proven to be specific inhibitors of the biological effects of PAF and are consequently useful for the treatment of asthma, anaphylactic and septic shock, psoriasis, bowel necrosis, adult respiratory distress syndrome, transplant rejection, thrombosis, stroke, cardiac anaphylaxis and cancer.

BRIEF SUMMARY OF THE INVENTION

The compounds of the present invention are represented by the Formula I.

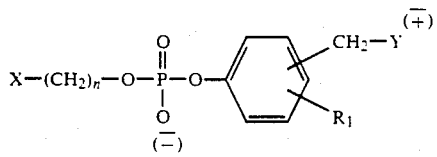

Formula I wherein: (A) X is a phenyl or naphthyl ring optionally substituted in any position with one or more substituents (i) —$R_2$, wherein $R_2$ is $C_1$-$C_{25}$ alkyl, $C_1$-$C_{25}$ alkenyl, $C_1$-$C_{25}$ alkoxy, $C_1$-$C_{25}$ alkenyloxy, $C_1$-$C_{25}$ thioalkyl, phenyl, phenoxy, substituted phenyl or substituted phenoxy wherein the substituents are $C_1$-$C_{20}$ alkyl, $C_1$-$C_{20}$ alkoxy, halogen or trifluoromethyl;

(ii) hydrogen, halogen, trifluoromethyl, cyano, or nitro;

(iii) —$CO_2R_3$, —$CONHR_3$, —CHO, —$OCONHR_3$, or —$NHCOR_3$ wherein $R_3$ is $C_1$-$C_{25}$ alkyl $C_1$-$C_{25}$ alkenyl, phenyl, or substituted phenyl, wherein the substituents are $C_1$-$C_{20}$ alkyl, $C_1$-$C_{20}$ alkoxy, halogen, or trifluoromethyl;

(B) $R_1$ represents one or more substituents of the aromatic ring which may be in any position and is $C_1$-$C_5$ alkyl, $C_1$-$C_5$ alkoxy or halogen.

—$CH_2$—Y represents a single substituent of the aromatic ring which may occupy any position wherein Y is a mono or bicyclic aromatic heterocycle with 5-7 membered rings containing at least one nitrogen atom which is bonded to the methylene group and optionally one or more other nitrogen or sulfur atoms; a preferred embodiment is compounds of formula I, above, wherein Y is

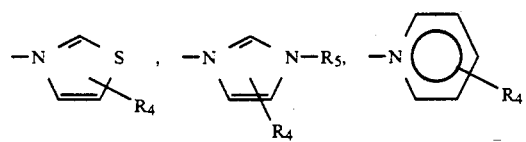

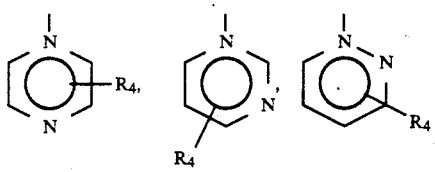

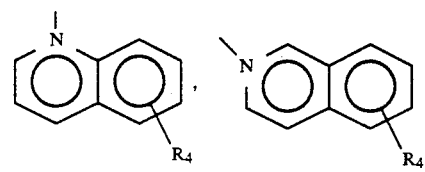

wherein $R_4$ represents one or more substituents of the heterocyclic ring which may occupy and non-hetero atom position and is $C_1$-$C_5$ alkyl, $C_1$-$C_5$ alkoxy, hydrogen or halogen; the moiety $R_5$ is $C_1$-$C_5$ alkyl or hydrogen.

(C) n is the integer 0 or 1.

DETAILED DESCRIPTION OF THE INVENTION

The preparation of compounds of this invention encompassed by Formulas IA-C is described hereinbelow in Flowsheet A, wherein n, X, $R_1$ and $R_5$ are described hereinabove. The moieties —$CH_2$—J and —$CH_2$—Y' represent substituents of the aromatic ring which are meta or para to the phosphate group wherein J is a leaving group such as the halogens chlorine or bromine and Y' is a nitrogen containing heterocycle which can be

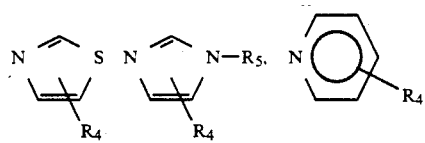

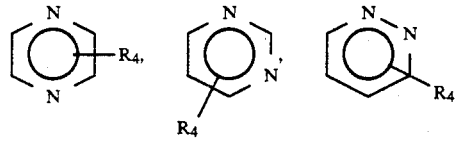

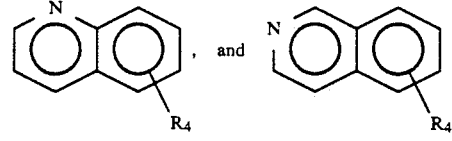

wherein $R_4$ and $R_5$ are as described hereinabove.

According to the sequence of reactions outlined in Flowchart A, the phenol or alcohol 2 is treated with an equivalent of the phosphorus reagent 3 in the presence of a base such as triethylamine in an inert solvent such as carbon tetrachloride to give, after hydrolysis of the resulting intermediate in a buffered solvent system such as tetrahydrofuran-water-sodium acetate, the phosphate 4. The reaction of 4 with a large excess of a nitrogen containing heterocycle in an inert solvent such as toluene at 50°-150° C. gives the compounds of this invention represented by formula IA. These compounds are obtained as internal salts except when A is an imidazole moiety.

In those cases where the compounds contain an imidazole ring (Formula IB), the imidazole moiety can be further alkylated with an excess of alkyl halide by heating in an inert solvent such as toluene to give the internal salts IC.

tion of 6 with a large excess of a nitrogen containing heterocycle in an inert solvent such as toluene at 50°-150° C. gives the compounds of this invention represented by formula ID. These compounds are obtained as internal salts except when Y' is an imidazole moiety. In those cases where the compounds contain an imidazole ring (formula IE), the imidazole moiety can be further alkylated with an excess of alkyl halide by heating in an inert solvent such as toluene to give the internal salts IF.

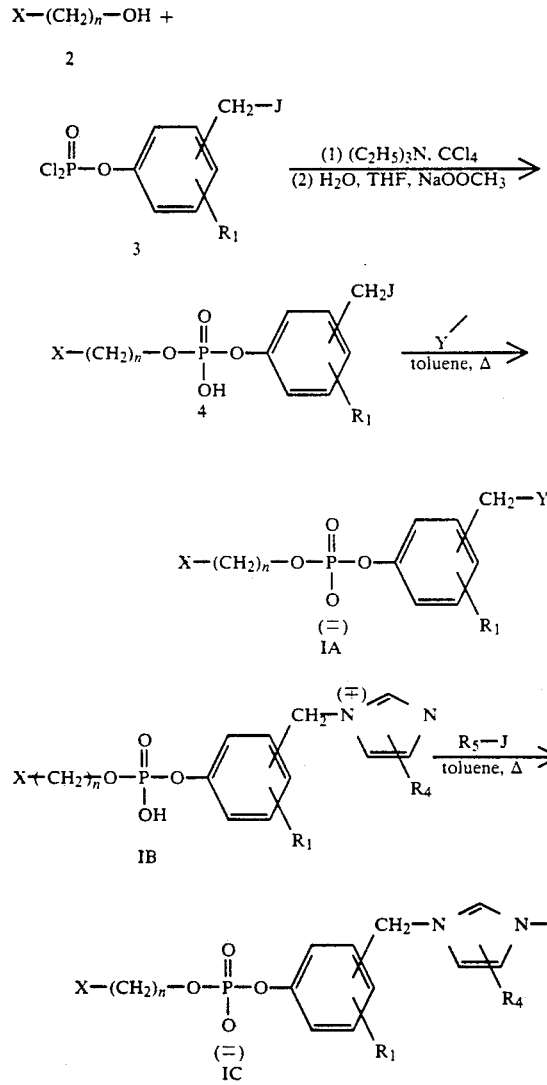

Flowsheet A

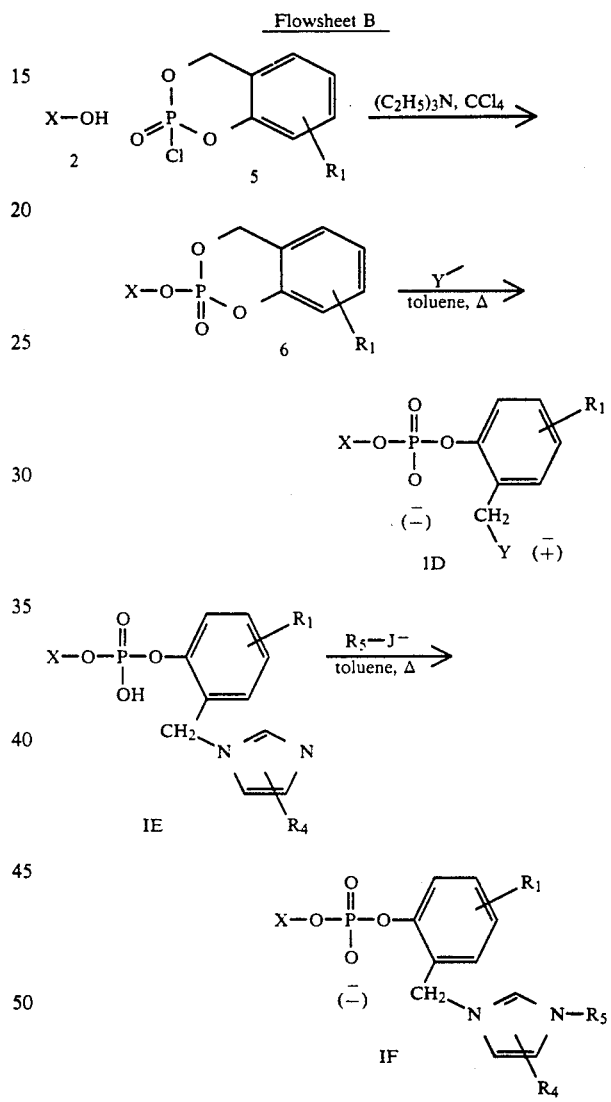

Flowsheet B

The preparation of compounds of this invention encompassed by formulas ID-IF is described hereinbelow in Flowchart B wherein $R_4$, $Y'$, $X$, $R_1$, and $R_5$, and $J$ are as defined hereinabove.

According to the sequence of reactions outlined in Flowchart B, the phenol 2 is treated with an equivalent of the phosphorus reagent 5 in the presence of a base such as triethylamine in an inert solvent such as carbon tetrachloride to give the cyclic phosphate 6. The reac- The phosphorous reagents represented by formulas 7a and 7b needed to prepare some of the compounds of this invention are prepared as described hereinbelow in Flowsheet C and in copending application Ser. No. 679,788, filed Dec. 10, 1984 and in Ser. No. 177,299 wherein $R_1$ is as defined hereinabove and J is chlorine or bromine.

According to the reaction outlined in Flowsheet C, the phenols 8a or 8b are reacted with phosphorous oxychloride and at least one equivalent of an amine base such as triethylamine in an inert solvent such as carbon tetrachloride to give the phosphorous reagents 7a and 7b.

Flowsheet C

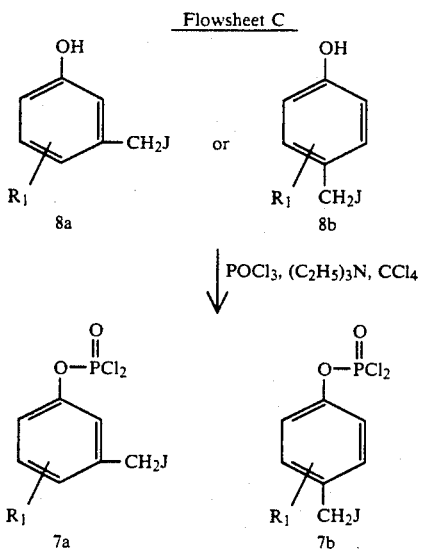

The cyclic phosphorous reagents represented by formula 9 needed to prepare some of the compounds of this invention are prepared as described hereinbelow in Flowsheet D wherein $R_1$ is as defined hereinabove.

According to the reactions outlined in Flowsheet D, the hydroxy phenol 10 is treated with an equivalent of phosphorous trichloride in an inert solvent such as ether in the presence of at least two equivalents of pyridine to give compound 11. Oxidation of 11 with a dry stream of oxygen in benzene then furnishes the phosphorous reagent 9.

Flowsheet D

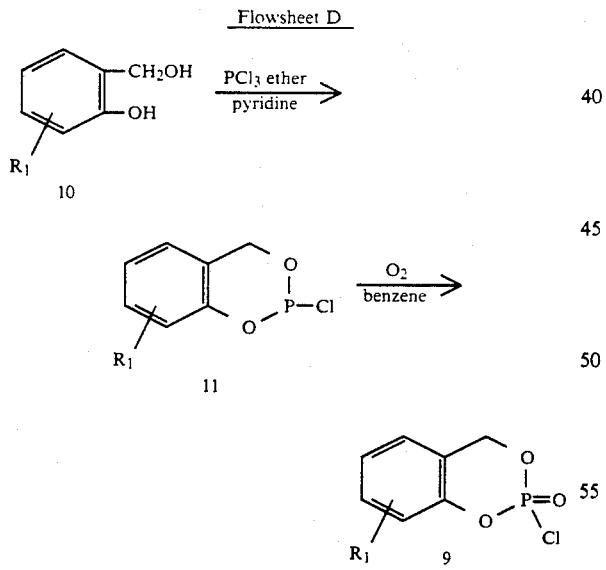

The substituted phenols and hydroxy naphthalenes of Formula 12 needed to prepare the compounds of this invention can be prepared as described in the following U.S. Pat. Nos.: 4,697,031; 4,699,990 and 4,640,913 and as described hereinbelow in Flowsheet E, wherein $R_6$ represents one or more substituents which may occupy any position and are selected from the group consisting of hydrogen, $-R_2$, trifluoromethyl, and fluorine wherein $R_2$ is as described hereinabove, and $R_7$ is $C_1$-$C_{25}$ alkyl or $C_1$-$C_{25}$ alkenyl. J' is chlorine, bromine or iodine.

According to the sequence of reactions outlined in Flowsheet E, a substituted bromo anisol 10 is reacted with magnesium in tetrahydrofuran to form the Grignard reagent which in turn is reacted with an alkyl halide in the presence of $Li_2CuCl_4$. The resulting methyl ether 11 is cleaved to the desired phenol using boron tribromide in an inert solvent such as methylene chloride. An identical sequence of reaction can be applied to furnish substituted hydroxy naphthalenes needed to prepare some of the compounds of this invention.

Flowsheet E

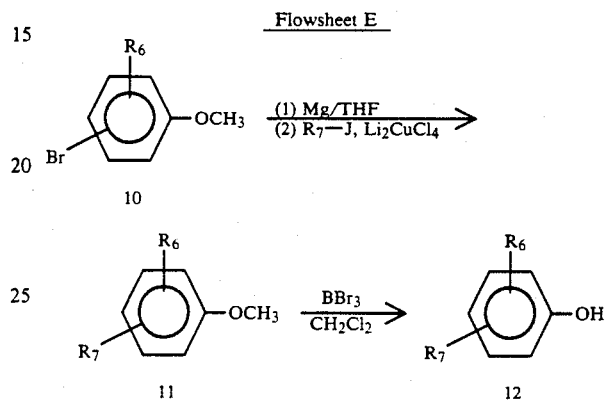

The substituted phenols and hydroxy naphthalenes of Formula 14 needed to prepare the compounds of this invention can be prepared as described in the following U.S. Pat. Nos.: 4,697,031; 4,699,990 and 4,640,913, in the following patent application Ser. No. 679,792, and as described hereinbelow in Flowsheet F wherein $R_2$ and J' are as hereinabove defined and $R_7$ is $C_1$-$C_{25}$ alkyl and $C_1$-$C_{25}$ alkenyl. According to the sequence of reactions shown in Flowsheet F, treatment of the dihydroxy compound 13 with sodium hydride in an inert solvent such as dimethylformamide in the presence of an alkyl halide produces the monoalkylated product 14 which can readily be separated from the unreacted 13 and the dialkylated product by a combination of distillation and chromatography. In those cases where two isometric monoalkylated products result, they can be separated using chromatographic procedures. An identical sequence of reactions can be applied to the synthesis of the hydroxy naphthalenes needed to prepare the compounds of this invention.

Some of the phenols and hydroxy naphthalenes that can be used to prepare the compounds of this invention are listed hereinbelow in Table I.

Flowsheet F

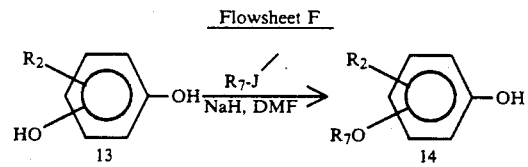

TABLE 1

2-dodecyloxyphenol
2-dodecyloxy-3-chlorophenol
2-dodecyloxy-3-methoxyphenol
2-dodecyloxy-4-chlorophenol
2-dodecyloxy-4-nitrophenol
2-dodecyloxy-4-carbomethoxyphenol

TABLE 1-continued 2-dodecyloxy-5-methylphenol
2-dodecyloxy-5-chlorophenol
2-dodecyloxy-5-t-butylphenol
2-dodecyloxy-5-methoxyphenol
2-tetradecyloxyphenol
2-tetradecyloxy-3-nitrophenol
2-tetradecyloxy-3-carbomethoxyphenol
2-tetradecyloxy-4-methylphenol
2-tetradecyloxy-4-t-butylphenol
2-tetradecyloxy-4-carbomethoxyphenol
2-tetradecyloxy-4-methoxyphenol
2-tetradecyloxy-5-methylphenol
2-tetradecyloxy-5-t-butylphenol
2-tetradecyloxy-5-nitrophenol
2-tetradecyloxy-5-carbomethoxyphenol
2-hexadecyloxyphenol
2-hexadecyloxy-3-chlorophenol
2-hexadecyloxy-3-methoxyphenol
2-hexadecyloxy-4-methylphenol
2-hexadecyloxy-4-chlorophenol
2-hexadecyloxy-4-nitrophenol
2-hexadecyloxy-4-methoxyphenol
2-hexadecyloxy-5-chlorophenol
2-hexadecyloxy-5-methoxyphenol
3-dodecyloxyphenol
3-dodecyloxy-2-methylphenol
3-dodecyloxy-2-chlorophenol
3-dodecyloxy-2-nitrophenol
3-dodecyloxy-2-carbomethoxyphenol
3-dodecyloxy-2-methoxyphenol
3-dodecyloxy-4-methylphenol
3-dodecyloxy-4-chlorophenol
3-dodecyloxy-4-t-butylphenol
3-dodecyloxy-4-methoxyphenol
3-dodecyloxy-5-methylphenol
3-dodecyloxy-5-trifluoromethylphenol
3-dodecyloxy-5-cyanophenol
3-dodecyloxy-5-pentylphenol
3-dodecyloxy-3-methoxy-5-pentadecylphenol
3-dodecyloxy-5-methoxyphenol
3-tetradecyloxyphenol
3-tetradecyloxy-2-methylphenol
3-tetradecyloxy-2-nitrophenol
3-tetradecyloxy-2-carbomethoxyphenol
3-tetradecyloxy-2-methoxyphenol
3-tetradecyloxy-4,6-dichlorophenol
3-tetradecyloxy-4-bromophenol
3-tetradecyloxy-4-n-propylphenol
3-decyloxy-4,6-di-n-hexylphenol
3-tetradecyloxy-5-chlorophenol
3-hexadecyloxyphenol
4-dodecyloxyphenol
4-dodecyloxy-2-methylphenol
4-dodecyloxy-2-chlorophenol
4-dodecyloxy-2-t-butylphenol
4-dodecyloxy-2,5-di-t-butylphenol
5-dodecyloxy-2,4-di-t-butylphenol
4-dodecyloxy-2-carbomethoxyphenol
4-dodecyloxy-3-methylphenol
4-dodecyloxy-3-chlorophenol
4-dodecyloxy-3-t-butylphenol
4-dodecyloxy-3-nitrophenol
4-dodecyloxy-3-carbomethoxyphenol
4-tetradecyloxyphenol
4-tetradecyloxy-2-chlorophenol
4-tetradecyloxy-2-t-butylphenol
4-tetradecyloxy-2-nitrophenol
4-tetradecyloxy-3-methylphenol
4-tetradecyloxy-3-chlorophenol
4-tetradecyloxy-3-t-butylphenol
4-tetradecyloxy-3-nitrophenol
4-hexadecyloxyphenol
4-hexadecyloxy-2-methylphenol
4-hexadecyloxy-2-chlorophenol
4-hexadecyloxy-3-methylphenol
4-hexadecyloxy-3-chlorophenol
5-dodecyloxy-1-naphthalenol
7-dodecyloxy-2-naphthalenol
4-dodecyloxy-1-naphthalenol
6-dodecyloxy-2-naphthalenol
4-tetradecyloxy-2,5-dichlorophenol The compounds of this invention were tested for pharmacological activity as described in the following tests.

Platelet Activating Factor Antagonism In Vitro

Test compounds were evaluated as PAF receptor antagonists in vitro by measuring inhibition of PAF (platelet activating factor) induced platelet aggregation. Platelet aggregation was measured by a modification of the method described in A. Wissner, et. al., J. Med. Chem., 27, 1174, 1984.

Approximately 120-240 ml of blood were collected by cardiac puncture from unanesthetized male New Zealand White rabbits (Whaley's Summit View Farms, Belvedere, N.J.) with the use of 3.2% sodium citrate anticoagulant (1 part of citrate/10 parts of blood). All syringes and pipets were plastic. The blood was gently mixed and immediately centrifuged at 800 rpm for 10-15 minutes at room temperature to recover the platelet rich plasma (PRP). Platelet poor plasma (PPP) was prepared by centrifuging PRP at 2800 rpm for 10 minutes at room temperature.

Dilutions (1:3000) of PRP in Isoton ® diluent were made and platelet counts were determined on a Coulter Thrombocounter which was standardized with platelet reference standards (Interscience Platelet Control, Portland, Oreg.). PRP platelet counts were adjusted to approximately 400,000-500,000 platelets/$\mu$l by the addition of PPP.

L-PAF was obtained from Calbiochem. A stock solution of 1-2 E-3M was prepared in 10% ethanol in water or 100% methanol and serial working dilutions were made using phosphate buffered saline (PBS). 1-2 E-3M stock solutions of test compounds were prepared in 100% methanol and serially diluted in PBS. All solutions were made up in plastic tubes, stored on ice and protected from heat and light. Solutions were prepared fresh or frozen at $-20°$ C. and used within 48 hours.

Incubation mixtures consisted of 400 $\mu$l PRP, 50 $\mu$l of PBS diluent or test compound and 50 $\mu$l of PAF agonist. More specifically, 400 $\mu$l of PRP was stabilized in a cuvette for 1-2 minutes at 37° C. in the aggregometer to achieve a stable baseline, then 50 $\mu$l of PBS or test compound, was added and incubated for 5 minutes before addition of the challenge concentration of PAF (final concentration of 5E-8M or 1E-7M, as determined from the dose response curve for PAF for that experiment). Aggregation was monitored for 5 minutes. Samples containing test compound or diluent were run simultaneously for comparison. Test compounds were initially evaluated at a screening concentration of 1E-5M. Those producing $\geq 50\%$ inhibition of the magnitude of aggregation were then reevaluated in a dose response fashion (final concentrations 1E-8M to 5E-5M) and $IC_{50}$ values were determined from the dose response curve.

The recording equipment consisted of a dual channel Chronolog aggregometer connected to a dual channel 10 MV full scale deflection Omniscribe chart recorder (Houston Instruments). The chart recorder was calibrated daily with the use of a suspension of Bio-Rad latex beads (S-X 12 400 mesh) which had a density slightly greater than rabbit PRP. The bead suspension was used to set the 0% light transmission mark and clear water was used to set the 100% light transmission mark. These limits defined a full scale deflection. The aggregation traces were analyzed by a digitizing method (C. Kohler and B. Zoltan, J. Pharm. Methods, 12, 113, 1984) with x, y coordinate data stored in a computer file. A suitable program computed parameters of interest such as the magnitude of aggregation.

In some experiments, washed rabbit platelets were used instead of rabbit PRP. Washed platelet suspensions were prepared as follows. Rabbit PRP was centrifuged at 2800 rpm for 10 minutes to obtain PPP and a platelet pellet. The pellet was gently suspended and washed in calcium free, albumin free Tyrode's buffer, pH 6.3. The suspension was recentrifuged and the washed pellet was resuspended in normal Tyrodes' buffer (with calcium, but albumin free), pH 7.4. Platelet counts were adjusted to 500,000 platelets/$\mu$l. The challenge concentration of PAF used for washed platelet experiments was 5E-9M.

In some experiments, human PRP was used instead of rabbit PRP. Blood from healthy volunteers was collected in Vacutainers ® containing the Na citrate diluent and processed in a manner similar to rabbit blood to obtain the PRP. For these experiments, the challenge concentration of PAF was 1E-6M.

The results of tests on representative compounds of this invention appear in Tables III, IV, V.

TABLE III

Inhibition of PAF-Induced Aggregation in Rabbit Platelet Rich Plasma

| Compound | IC$_{50}$(M) |
|---|---|
| 3-[[3-[[[3-(hexadecyloxy)phenoxy]hydroxyphosphinyl]oxy]phenyl]methyl]thiazolium, hydroxide, inner salt | 2.13E-6(4) |
| 3-[[3-[[[3-(hexadecyloxy)-2-methyl-phenoxy]hydroxyphosphinyl]oxy]phenyl]methyl]thiazolium, hydroxide, inner salt | 2.65E-6(3) |
| 1-[[3-[[[3-(hexadecyloxy)phenoxy]hydroxyphosphinyl]oxy]phenyl]methyl]pyridinium, hydroxide, inner salt | 1.54E-5(1) |
| 1-[[3-[[[3-(hexadecyloxy)phenoxy]hydroxyphosphinyl]oxy]phenyl]methyl]quinolinium, hydroxide, inner salt | 2.18E-5(1) |
| 3-[[3-[[[3-(dodecyloxy)phenoxy]hydroxyphosphinyl]oxy]phenyl]methyl]thiazolium, hydroxide, inner salt | 5.28E-5(2) |
| 3-[[3-[[3-[4-(hexadecyloxy)phenoxy]hydroxyphosphinyl]oxy]phenyl]methyl]thiazolium, hydroxide, inner salt | 3.28E-6(2) |
| 3-[[3-[[hydroxy]-2-(tetradecyloxy)phenoxy)phophinyl]oxy]phenyl]methyl]thiazolium, hydroxide, inner salt | 5.75E-5(1) |
| 3-[[3-[[hydroxy(3-tetradecyl-phenoxy)phosphinyl]oxy]phenyl]methyl]thiazolium, hydroxide, inner salt | 1.88E-5(2) |
| 3-[[3-[[hydroxy[2-methoxy-3-(tetradecyloxy)phenoxy]phosphonyl]oxy]phenyl]methyl]thiazolium, hydroxide, inner salt | 7.50E-6(3) |
| 1-[[3-[[hydroxy[2-methoxy-3-(tetradecyloxy)phenoxy]phosphinyl]oxy]phenyl]methyl]pyridinium, hydroxide, inner salt | 1.65E-4(2) |
| 3-[[3-[[hydroxy[[3-(tetradecyloxy)phenyl]methoxy]phosphinyl]oxy]phenyl]methyl]thiazolium, hydroxide, inner salt | 4.22E-6(2) |
| 1-[[3-[[hydroxy[2-methoxy-3-(tetradecyloxy)phenoxy]phosphinyl]oxy]phenyl]methyl]-quinolinium, hydroxide, inner salt | 8.0E-6(2) |
| 2-[[3-[[hydroxy[2-methoxy-3-(tetradecyloxy)phenoxy]phosphinyl]oxy]phenyl]methyl]-isoquinolinium, hydroxide, inner salt | 2.0E-5(2) |
| 3-[[3-[[hydroxy[2-methoxy-3-(tetradecyloxy)phenoxy]phosphinyl]oxy]phenyl]methyl]-5-methyl-thiazolium, hydroxide, inner salt | 2.51E-6(7) |
| 3-[[2-[[[3-(hexadecyloxy)phenoxy]hydroxyphosphinyl]oxy]phenyl]methyl]thiazolium, hydroxide, inner salt | 6.36E-6(2) |
| 3-[[3-[[hydroxy[3-(tetradecyl-oxy)phenoxy]phosphinyl]oxy]phenyl]methyl]thiazolium, hydroxide, inner salt | 6.15E-6(2) |
| 3-[[3-[[hydroxy[3-(tetradecyl-oxy)phenoxy]phosphinyl]oxy]phenyl]methyl]-5-methyl-thiazolium, hydroxide, inner salt | 8.82E-6(2) |
| 3-[[3-[[[2,4-bis(1,1-dimethylethyl-5-(dodecyloxy)phenoxy]hydroxyphosphinyl]oxy]phenyl]methyl]thiazolium, hydroxide, inner salt | 3.02E-5(2) |
| 1-[[3-[[[3-(hexadecyloxy)-2-methylphenoxy]hydroxyphosphinyl]oxy]phenyl]methyl]quinolinium | 2.96E-5(2) |
| 3-[[3-[[[7-(dodecyloxy)-2-napthhalenyl]oxy]hydroxyphosphinyl]oxy]phenyl]methyl]thiazolium, hydroxide, inner salt | 2.64E-5(2) |
| 3-[[3-[[hydroxy[2-(methoxycarbonyl)-3-(tetradecyloxy)phenoxy]phosphinyl]oxy]phenyl]methyl]-thiazolium, hydroxide, inner salt | 2.70E-6(2) |
| 3-[[3-[[hydroxy[2-(methoxycarbonyl)-3-(tetradecyloxy)phenoxy]phosphinyl]oxy]phenyl]methyl]-5-methyl-thiazolium, hydroxide, inner salt | 5.21E-7(2) |
| 1-[[3-[[hydroxy[2-(methoxycarbonyl)-3-(tetradecyloxy)phenoxy]phosphinyl]oxy]phenyl]methyl]-quinolinium, hdyroxide, inner salt | 6.26E-6(2) |
| 3-[[3-[[[2,5-bis(1,1-dimethyl-ethyl)-4-(dodecyloxy)phenoxy]hydroxyphosphinyl]oxy]phenyl]methyl]-5-methyl-thiazolium, hydroxide, inner salt | 4.12E-7(4) |
| 1-[[3-[[[2,5-bis(1,1-dimethyl-ethyl)-4-(dodecyloxy)phenoxy]hydroxyphosphinyl]oxy]phenyl]methyl]quinolinium, hydroxide, inner salt | 1.36E-6(3) |
| 1-[[3-[[[3-(didecyloxy)-2-methoxyphenoxy]hydroxyphosphinyl]oxy]phenyl]methyl]-quinolinium, hydroxide, inner salt | 2.47E-5(1) |
| 3-[[3-[[[3-(dedecyloxy)-2-methoxy-decylamino)carbonyl]oxy]phenoxy]phosphinyl]oxy]phenyl]methyl]thiazolium, hydroxide, inner salt | 1.72E-6(2) |
| 3-[[3-[[hydroxy[2-methyl-3-[[(octa-decylamino)carbonyl]oxy]phenoxy]phosphinly]oxy]phenyl]methyl]thiazolium, hydroxide, inner salt | 3.72E-6(2) |
| 3-[[3-[[hydroxy[2-methyl-3-[[(octa-decylamino)carbonyl]oxy]phenoxy]phosphinly]oxy]phenyl]methyl]-5-methyl-thiazolium, hydroxide, inner salt | 1.8E-6(1) |
| 3-[[3-[[hydroxy[4-(phenylmethoxy)phenoxy]phosphinyl]oxy]phenyl]methyl]-5-methyl-thiazolium, hydroxide, inner salt | 1.53E-3(1) |

Data are in Molar IC$_{50}$ values (concentration which produces 50% inhibition) in rabbit platelet rich plasma. The challenge concentration of 1-PAF (platelet activating factor) was 5E-8M. Numbers in parentheses refer to number of experiments.

TABLE IV

Inhibition of PAF-Induced Aggregation in Washed Rabbit Platelets

| Compound | IC$_{50}$(M)* |
| --- | --- |
| 3-[[3-[[hydroxy[2-methoxy-3-(tetradecyloxy)phenoxy]phosphinyl]oxy]phenyl]methyl]-5-methyl-thiazolium, hydroxide, inner salt | 5.49E-9(1) |
| 3-[[3-[[[2,5-bis(1,1-dimethylethyl)-4-(dodecyloxy)phenoxy]hydroxyphosphinyl]oxy]phenyl]methyl]thiazolium, hydroxide, inner salt | 2.12E-9(2) |

Data are in molar IC$_{50}$ values (concentration which produces 50% inhibition) in washed rabbit platelets. The challenge concentration of PAF was 5E-9M. Numbers in parentheses refer to number of experiments.

TABLE V

Inhibition of PAF-Induced Aggregation in Human Platelet Rich Plasma

| Compound | IC$_{50}$(M) |
| --- | --- |
| 3-[[3-[[[3-(hecadecyloxy)phenoxy]hydroxyphosphinyl]oxy]phenyl]methyl]thiazolium, hydroxide, inner salt | 2.5E-6(1) |
| 3-[[3-[[[3-(hexadecyloxy)-2-methylphenoxy]hydroxyphosphinyl]oxy]phenyl]methyl]thiazolium, hydroxide, inner salt | 1.19E-7(1) |
| 3-[[3-[[hydroxy[2-methoxy-3-(tetradecyloxy)phenoxy]phosphinyl]oxy]phenyl]methyl]-thiazolium, hydroxide, inner salt | 2.64E-5(2) |
| 3-[[3-[[hydroxy[2-methoxy-3-(tetradecyloxy)phenoxy]phosphinyl]oxy]phenyl]methyl]-5-methyl-thiazolium, hydroxide, inner salt | 3.10E-5(2) |
| 3-[[3-[[[2,5-bis(1,1-dimethylethyl)-4-(dodecyloxy)phenoxy]hydroxyphosphinyl]oxy]phenyl]-thiazolium, hydroxide, inner salt | 1.93E-6(1) |
| 3-[[3-[[[2,5-bis(1,1-dimethylethyl)-4-(dodecyloxy)phenoxy]hydroxyphosphinyl]oxy]phenyl]-methyl]quinolinium, hydroxide, inner salt | 4.75E-5(2) |

Data are in molar IC$_{50}$ values (concentration which produces 50% inhibition) in human platelet rich plasma. Numbers in parentheses refer to number of experiments.

IN VIVO TESTS FOR PAF ANTAGONISM

A. Guinea Pig Vascular Permeability (Skin Lesion) Model

PAF produces a rapid increase in capillary permeability and intradermal injection of PAF causes leakage of plasma proteins into the extracellular space. If these proteins are previously tagged with Evan's blue dye, a blue spot develops in the skin. A PAF antagonist will reduce the leakage and reduce the size of the spot. Specificity of the PAF antagonist can be determined by also checking the response to other agonists such as histamine.

The initial in vivo test uses coinjection of test compound and PAF agonist in the guinea pig skin model. The following protocol describes the coinjection methodology.

Hartley strain guinea pigs (300-400 gm) were maintained with food and water ad lib. The backs and hind feet of the animals were shaved 1 day before use. PAF (Sigma) P9525) was dissolved in saline at 500 ng/ml and diluted 1:1 to make a 250 ng/ml solution. Histamine diphosphate (Sigma H7375) was dissolved in saline at 25 ug/ml. Test compounds were dissolved in ETOH at 10 mg/ml. The injection solutions were made by mixing 10 ul of test compound solution or ETOH into 1 ml of PAF or histamine solution.

The guinea pigs were given 2 ml of Evan's Blue dye (0.5% w/v) in saline via a foot vein. Immediately after, six 0.1 ml intradermal injections were made into the back of the guinea pig, 3 per side. The left side was injected with 50 ng PAF+10 ug test compound (0.1 ml of 500 ng/ml PAF+100 ug/ml test compound), 25 ng PAF+10 ug test compound, and 2.5 ug histamine +10 ug test compound. The right side was injected with the same pattern of the ETOH control solutions. In addition, a separate group of animals received 10 ug of test compound saline as a control for direct test compound effects.

Twenty minutes later, the animals were killed by a blow to the head and the skin reflected from the back. The blue lesion areas (due to increased vascular permeability) were estimated as the product of the longest and shortest diameters. A compound was considered active if it reduced the PAF induced lesion by 50% or more without altering a histamine induced lesion.

Those compounds which were active by the coinjection route were examined by intraperitoneal administration. Two protocols were used, the first with both PAF and histamine as agonists; the second used 6 concentration levels of PAF. Protocols were similar to the methods described above, except ETOH was eliminated from the solutions.

In protocol I, the PAF was administered by intradermal injections at 50, 25, and 12.5 ng/site and histamine at 2, 1, and 0.5 ug/site. In protocol II, six sites were injected with PAF at 50, 25, 12.5, 6.25, 3.125, and 1.56 ng/site. For each protocol, the methods were as described above. A compound was considered active at the dose used if it significantly reduced the PAF lesions without altering the histamine response.

B. PAF Induced Lethality in Mice

PAF given I.V. to mice causes an immediate hypotensive shock leading to death in 1 hour or less. Compounds were given intraperitoneally or P.O. at various times before the PAF challenge. Animals alive after 2 hours were counted and the activity of test compounds expressed as % survival corrected for any control (saline treated) animals which survived the PAF challenge. Results of this assay appear in Table VI.

C. Endotoxin Induced Hypotension in Rats

Rats given LPS I.V. demonstrates a profound hypotension; to the extent that this is a PAF induced phenomena, a PAF antagonist should restore normal blood pressure.

Bacterial cell wall lipopolysaccharide from *E. coli* strain 0111:B4 (Sigma #L-2630) was dissolved in saline at a concentration of 3.75 mg/ml and administered to rats at 15 mg/kg I.V. Test compounds were dissolved in saline at 1 mg/ml, diluted to 10 ug/ml, and injected intraarterially at 1 ml/kg (10 ug/kg). Male wistar strain rats were obtained from Charles River Labs and maintained according to ALAC standards. They were anesthetized with 30 mg/kg pentobarbital ip with supplementation as needed. The throat was opened, the left carotid artery was cannulated with PE-10 tubing and the trachea cannulated with 0.100 O.D. tubing. Ventilation was maintained by a Harvard Apparatus small animal pump at a rate sufficient to nearly abolish spontaneous respiration. The mean arterial pressure was measured using a Statham PM23 transducer and displayed on a Grass model 7 polygraph. Endotoxin was given intravenously or intraarterially if the tail veins had collapsed. After 5 minutes, the test compound was given intraarterially since the tail veins generally collapsed after endotoxin administration.

Results are expressed as the % reversal of the fall in mean arterial pressure as shown in Table VII.

TABLE VI

| Compound | PAF Induced Skin Lesions % of Control[a] | PAF Induced Lethality[b] % Protection |
|---|---|---|
| 3-[[3-[[3-[4-(hexadecyloxy)phenoxy]hydroxyphosphinyl]oxy]phenyl]methyl]thiazolium, hydroxide, inner salt | 60 | 96 |
| 3-[[3-[[hydroxy[2-methoxy-3-(tetradecyloxy)phenoxy]phosphinyl]oxy]phenyl]methyl]thiazolium, hydroxide, inner salt | 75[c] | 12 |
| 3-[[3-[[hydroxy[2-methoxy-3-(tetradecyloxy)phenoxy]phosphinyl]oxy]phenyl]methyl]-5-methylthiazolium, hydroxide, inner salt | — | 17 |
| 3-[[3-[[[2,5-bis(1,1-dimethylethyl)-4-(dodecyloxy)phenoxy]hydroxyphosphinyl]oxy]phenyl]methyl]thiazolium hydroxide, inner salt | 49[d] | 27[c] |
| 3-[[3-[[hydroxy[2-(methoxycarbonyl)-3-(tetradecyloxy)phenoxy]phosphinyl]oxy]phenyl]methyl]thiazolium, hydroxide, inner salt | — | 12 |
| 3-[[3-[[hydroxy[2-(methoxycarbonyl-3-(tetradecyloxy)phenoxy]phosphinyl]oxy]phenyl]methyl]-5-methyl-thiazolium hydroxide, inner salt | — | 0 |
| 3-[[3-[[[2,5-bis(1,1-dimethylethyl)-4-(dodecyloxy)phenoxy]hydroxyphosphinyl]oxy]phenyl]-methyl]-5-methyl-thiazolium, hydroxide, inner salt | — | 36 |

[a] % of control when 10 μg of test compound was coinjected into guinea pig skin with PAF
[b] % prevention of death when given I.P. at 10 mg/kg except where noted corrected for control lethality
[c] I.P. 4 mg/kg 1 hour before PAF
[d] P.O. 5 mg/kg 4 hours before PAF
[e] P.O. 10 mg/kg 4 hours before PAF

TABLE VII

Effect of PAF Antagonist in Reversing Endotoxin Induced Hypotension
Reversal of LPS Induced Hypotension in anesthetized rats.

| Compound | % Reversal of Hypotension |
|---|---|
| 3-[[3-[[hydroxy[2-methoxy-3-(tetradecyloxy)phenoxy]-phosphinyl]oxy]phenyl]-methyl]thiazolium, hydroxide, inner salt | 89 |
| 3-[[3-[[hydroxy([2-methoxy-3-(tetradecyloxy)phenoxy]-phosphinyl]oxy]phenyl]methyl]-5-methyl-thiazolium, hydroxide, | 84 |

TABLE VII-continued

Effect of PAF Antagonist in Reversing Endotoxin Induced Hypotension
Reversal of LPS Induced Hypotension in anesthetized rats.

| Compound | % Reversal of Hypotension |
|---|---|
| inner salt | |

D. Endotoxin Induced Shock and Mortality in Mice

Endotoxin administration produces a shock state characterized by hypotension, neutropenia, thrombocytopenia and death. PAF administration mimics the signs and symptoms of endotoxin induced shock and death and endotoxin also induces the release of PAF. Therefore, the effects of endotoxin should be blocked with a PAF antagonist.

Male Balb/c mice (approximately 20 g) were obtained from Charles River Laboratories and used after a one week acclimation period. Animals were injected (iv or ip) with test compound at different time intervals prior to the iv or ip injection of endotoxin. Sigma *E. Coli* endotoxin, 0111:B4, phenol extraction, catalog # L2630 was used for these studies.

The endotoxin dose was determined from dose-response titrations and adjusted to a dose that was lethal for 90% ($LD_{90}$) of the mice within a 24 hour period. This $LD_{90}$ value was approximately 50 mg/kg iv and 80 mg/kg ip. The number of survivors in each group (control or treated with test compound) was recorded after 24, 48 or 72 hours and the treated groups (receiving test compound and endotoxin) was compared with the untreated, control group (receiving endotoxin only).

The test compounds, known to be PAF antagonists from in vitro platelet aggregation studies, were active in reducing 24 hour mortality when administered ip prior to a lethal ip injection of endotoxin (Table VIII). The test compounds (PAF antagonists) were also efficacious when administered iv prior to a lethal iv injection of endotoxin (Table IX).

TABLE VIII

Effect of PAF Antagonists on Endotoxin: Induced Mortality in Mice[a]

| Compound | Dose (mg/kg) | 24 Hour Survival (# Alive/Total) Treated | Control |
|---|---|---|---|
| 3-[[3-[[hydroxy[2-methoxy-3-(tetradecyloxy)phenoxy]phosphinyl]-oxy]phenyl]methyl]thiazolium, hydroxide, inner salt | 30 | 12/50 | 4/50 |
|  | 10 | 7/30 | 1/30 |
| 3-[[3-[[hydroxy[2-methoxy-3-(tetradecyloxy)phenoxy]phosphinyl]-oxy]phenyl]methyll]-5-methyl-thiazolium, hydroxide, inner salt | 40 | 13/50 | 4/50 |
| 3-[[3-[[[2,5-bis(1,1-dimethylethyl)-4-(dodecyloxy)phenoxy]hydroxyphosphinyl]oxy]phenyl]-methyl]thiazolium, hydroxide, inner salt | 40 | 6/20 | 0/20 |
|  | 20 | 6/20 | 0/20 |
|  | 10 | 4/20 | 0/20 |

[a] Test compound or placebo was injected (IP) 2 hours prior to the IP injection of endotoxin. The endotoxin dose used was selected to kill 90-100% of the animals. The treated group received test compound plus endotoxin. The control group received placebo plus endotoxin.

TABLE IX

Effect of PAF Antagonists on Endotoxin: Induced Mortality in Mice[a]

| Compound | Dose (mg/kg) | Survival After 24 hrs. (# Alive/Total) | |
|---|---|---|---|
| | | Treated | Control |
| 3-[[3-[[hydroxy[2-methoxy-3-(tetradecyl-oxy)phenoxy]phosphinyl]oxy]phenyl]methyl]thiazolium, hydroxide, inner salt | 10 | 4/20 | 0/20 |
| 3-[[3-[[hydroxy[2-methoxy-3-(tetradecyl-oxy)phenoxy]phosphinyl]oxy]phenyl]methyll]-5-methyl-thiazolium, hydroxide, inner salt | 20 | 14/40 | 3/40 |

[a]Test compound or placebo was injected (IP) 2 hours prior to the IP injection of endotoxin. The endotoxin dose used was selected to kill 90–100% of the animals. The treated group received test compound plus endotoxin. The control group received placebo plus endotoxin.

E. Endotoxin Induced Hemorragic Lesions in Rats

Endotoxin induces an immediate, profound hemorragic lesion in the gut of rodents. 3-[[3-[[hydroxy[2-methoxy-3-(tetradecyloxy)phenoxy]phosphinyl]oxy]-phenyl]-methyl]-5-methyl-thiazolium, hydroxide, inner salt given IP one hour before challenge at doses as low as ½ mg/kg is able to reduce or eliminate the damage produced by IV LPS. Results of this assay appear in Table X.

One of the main sites of LPS induced pathology in the rat and guinea pig is the gut, particularly the duodenum, small intestine and cecum. After LPS exposure hemorragic lesions develop within a few minutes and can involve most of the lumenal surface. The extent of these pathologies can be quantitated histologically or by measuring the amount of plasma proteins that have leaked into the lumen. The second method is much faster and can detect damage in the junctions between capillary or intestinal epithelial cells before gross lesions have developed. Hot tags have shown plasma leakage after LPS challenge using radiolabeled albumin as the probe. In our assay we have chosen to use a non-radioactive tagging method in which plasma albumin is labeled with Evan's blue dye and the lumenal leakage is determined spectrophotometricly.

The data available now indicates that LPS acts by inducing the synthesis and release of tumor necrosis factor (TNF) which in turn causes synthesis and release of platelet activating factor (PAF). PAF seems to be the major cytotoxic agent involved in many of the pathophysiologic changes seen in endotoxic shock and these changes can be induced by direct injection of PAF. Therefore a PAF antagonist ought to prevent the intestinal damage brought on by injection of LPS. We have demonstrated that 3-[[3-[[hydroxy[2-methoxy-3-(tetradecyloxy)phenoxy]phosphinyl]oxy]phenyl]methyl]-5-methyl-thiazolium, hydroxide, inner salt prevents the gut manifestations of endotoxin shock and does so at doses as low as 0.25 mg/kg in rats.

Chemicals

Evan's blue dye: Sigma e-2129, made as a 1% w/v solution in saline which was filtered and kept refrigerated.

Platelet activating factor (PAF) was obtained from Sigma, P-9525. This is supplied as a chloroform solution at 2 mg/ml and was diluted in the dye solution to 2.5 μg/ml.

For each experiment fresh 3-[[3-[[hydroxy[2-methoxy-3-(tetradecyloxy)phenoxy]phosphinyl]oxy]-phenyl]-methyl]-5-methyl-thiazolium, hydroxide, inner salt was sonicated into saline.

Biologicals

Endotoxin: Lipopolysaccharide (LPS) isolated from *E. coli* strain 0111:b4 by phenol extraction was obtained from Sigma, L-2630. LPS solutions were made fresh for each experiment.

Animals

Male Wistar rats, obtained from Charles River, weighing 160–225 gm were maintained in accordance with ALAC standards for at least one week before use.

Protocols

Food was withheld from the animals for 18 hours before the experiment to clear the intestine. The rats were dosed with 3-[[3-[[hydroxy[2-methoxy-3-(tetradecyloxy)phenoxy]phosphinyl]oxy]phenyl]methyl]-5-methyl-thiazolium, hydroxide, inner salt or saline ip, 4 ml/kg, ½ hour before challenge with 25 or 50 mg/kg LPS in the 1% dye at 10 ml/kg. One hour after the LPS insult the animals were sacrificed and the duodenum and initial 6–7 cm of the jejunum isolated. This segment was lavaged with 2 ml of normal saline with the fluid flowing into polyethylene tubes. The lavageate frequently contained mucous and in order to free the stained albumin the samples were sonicated vigorously and then centrifuged to clarify the fluid. The amount of dye was determined spectrophotometrically, using a Vmax microtiter plate reader using the end point mode at 600 nM.

Discussion

The most obvious damage seen in examination of rodents given endotoxin is a massively swollen caecum and hemorragic lesions in the stomach and small intestine. Similar pathology is also seen in humans with systemic septic shock. The relative importance of direct capillary damage by PAF vs ischemia-reperfusion damage brought on by the profound hypotension induced by LPS is unknown. However, 3-[[3-[[hydroxy[2-methoxy-3-(tetradecyloxy)phenoxy]-phosphinyl]oxy]-phenyl]-methyl]-5-methyl-thiazolium, hydroxide, inner salt has demonstrated very potent protection against the end point of gut pathophysiology. Direct observation of the intestinal tract of LPS challenge control animals and 3-[[3-[[hydroxy[2-methoxy-3-(tetradecyloxy)phenoxy]-phosphinyl]oxy]phenyl]methyl]-5-methyl-thiazolium, hydroxide, inner salt protected animals revealed that the protected animals had nearly normal appearing guts. Blind testing became difficult as virtually all the control animals had severe diarrhea while the 3-[[3-[[hydroxy[2-methoxy-3-(tetradecyloxy)phenoxy]phosphinyl]oxy]-phenyl]methyl]-5-methyl-thiazolium, hydroxide, inner salt animals had little or none. The overall activity of 3-[[3-8 [hydroxy[2-methoxy-3-thiazolium, hydroxide, inner salt was significant with activity seen at doses as low as ½ mg/kg IP.

TABLE X

Reduction of IV LPS Induced Gut Leakage
By 3-[[3-[[Hydroxy[2-methoxy-3-(tetra-
decyloxy)phenoxy]phosphinyl]oxy]phenyl]methyl]-
5-methyl-thiazolium, hydroxide, inner salt
Given IP In Rats

| Dose (mg/kg) | % of Control Leakage (K)$^a$ for Each Experimental Run Experiment | | |
|---|---|---|---|
| | 1 | 2 | 3 |
| 20. | 20 ± 2 | 19 ± 31 | |
| 2. | 10 ± 10 | 18 ± 24 | 27 ± 11 |
| 1. | 22 ± 15 | | |
| 0.5 | 15 ± 10 | 16 ± 9 | |
| 0.25 | 36 ± 23 | 65 ± 15 | |
| 0.125 | 24 ± 15 | 107 ± 27 | |

$^a$Values are expressed as the percentage of dye leakage in control LPS animals corrected for background leakage ± SEM. There were from 5 to 8 animals per cell in each determination. Note columns are not necessarily the same experiment.
C = Dye leakage in LPS
(15 mg/kg IV) challenged animals
B = Dye leakage in animals given dye only
R = Dye leakage in animals given 3-[[3-[[hydroxy[2-methoxy-3-(tetradecyloxy)-phenoxy]phosphinyl]oxy]phenyl]methyl]-5-methyl-thiazolium, hydroxide, inner salt $$K = \left\{ \frac{(R - B)}{(C - B)} \right\} \times 100$$

The active compounds of the present invention may be orally administered, for example, with an inert diluent, or with an assimilable edible carrier, or they may be enclosed in hard or soft shell capsules, or they may be compressed into tablets, or they may be incorporated directly with the food of the diet. For oral therapeutic administration, these active compounds may be incorporated with excipients and used in the form of tablets, capsules, elixirs, suspensions, syrups and the like. Such compositions and preparations should contain at least 0.1% of active compound. The percentage of the compound in these compositions may, of course, be varied and may conveniently be between about 2% to about 60% of the weight of the unit. The amount of active compound in such therapeutically useful compositions is such that a suitable dosage will be obtained. Preferred compositions according to this invention are prepared so that an oral dosage unit contains between about 1 and 250 mg of active compound.

The tablets, capsules and the like may also contain a binder such as gun tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When the dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to active ingredient, sucrose as a sweetening agent, methyl and propylparabens as preservatives, a dye and flavoring such as cherry or orange flavor.

These active compounds may also be administered parenterally. Solutions or suspensions of these active compounds can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacterial and fungi. The carrier can be a solvent or dispersion medium containing, for example, water, ethanol, polyol (e.g. glycerol, propylene glycol and liquid polyethylene glycol), suitable mixtures thereof, and vegetable oils.

The compounds of this invention may also be administered directly to the airways in the form of an aerosol.

The invention will be further described by the following examples.

EXAMPLE 1

3-(Bromomethyl)phenyl phosphodichlorodate

A 9.1 g portion of 99% phosphorous tribromide, 10 ml of carbon tetrachloride and 1.32 ml of dry pyridine in 2.5 ml of tetrahydrofuran was reacted with 12.41 g of 4-hydroxybenzyl alcohol in 100 ml of dry tetrahydrofuran containing 0.7 ml of pyridine. The intermediate 4-hydroxybenzyl bromide was treated with phosphorous oxychloride, giving 5.6 g of the desired compound.

EXAMPLE 2

2-Chloro-4H-1,3,2-benzodioxaphosphorin, 2-oxide

To a solution of 100 g of hydroxybenzyl alcohol and 121.69 g of phosphorous trichloride in 1000 ml of ether at $-10°$ C., was added dropwise a solution of 133.81 g of pyridine in 200 ml of ether over 1.5 hours. The mixture was stirred for 1.5 hours at room temperature and then refrigerated overnight. The mixture was filtered, the solvent removed, hexane added, the mixture filtered and the solvent removed. The residue was distilled via a Kugelrohr (1 mm 80°-90° C.) giving 81 g of a colorless liquid. A solution of this material in benzene was stirred and dry oxygen bubbled in for 20 hours, then the benzene was removed, giving 87.5 g of the desired compound as a yellow liquid.

EXAMPLE 3

3-(Hexadecyloxy)phenol

To a suspension of 29.6 g of sodium hydride in 215 ml of N,N-dimethylformamide was added dropwise over 1.5 hours a solution of 54.33 g of resorcinol in 145 ml of N,N-dimethylformamide and 72 ml of tetrahydrofuran. The resulting mixture was cooled to 0° C. and 7.4 g of sodium iodide added followed by the dropwise addition of 155.0 g of hexadecylbromide over 1 hour. The bath was removed and the mixture stirred at ambient temperature for 17 hours. The mixture was diluted with 500 ml of iced dilute hydrochloric acid, extracted with ether and filtered. The ether layer was dried over magnesium sulfate and evaporated to an oil which was purified by chromatography on silica gel using ethyl acetate-hexanes giving 37.2 of the desired compound as a white solid, m.p. 58°-59° C.

EXAMPLE 4

3-(Bromomethyl)phenyl 3-(hexadecyloxy)phenyl phosphate

To a solution of 5.0 g of 3-(hexadecyloxy)phenol in 60 ml of dry carbon tetrachloride cooled in an ice bath was added a solution of 5.5 g of 3-(bromomethyl)phenyl phosphodichloride in 10 ml of carbon tetrachloride in an inert atmosphere. A solution of 2.52 ml of triethylamine in 10 ml of carbon tetrachloride was rapidly added followed by cooling bath removal and stirring overnight. Filtered the mixture through diatomaceous earth and evaporated to a residue which was stirred for two hours with 130 ml of tetrahydrofuran and 130 ml of 0.5M sodium acetate. The tetrahydrofuran was removed under vacuum and the aqueous residue cooled and acidified with hydrochloric acid followed by ether extraction. The organic layer was washed with saturated sodium chloride, dried with magnesium sulfate and evaporated to a viscous oil which was purified by chromatography on magnesium silicate with chloroform and 10% methyl alcohol-chloroform giving 7.0 g of the desired compound as a glass.

EXAMPLE 5

3-[[3-[[[3-(Hexadecyloxy)phenoxy]hydroxyphosphinyl]-oxy]phenyl]methyl]-thiazolium, hydroxide, inner salt To a solution of 2.0 g of 3-(bromomethyl)phenyl 3-(hexadecyloxy)phenyl phosphate in 15 ml of dry toluene was added 2.3 g of triazole followed by stirring at 65°–70° C. in an inert atmosphere for 18 hours. The residue, from solvent removal, was purified by chromatography on silica gel with methyl alcohol-chloroform then chloroform-methyl alcohol-water, triturated with ether and refrigerated giving 1.65 g of the desired compound as a white amorphous solid.

EXAMPLE 6

1-[[3-[[[3-(Hexadecyloxy)phenoxy]hydroxyphosphinyl]-oxy]phenyl]methyl]-quinolinium, hydroxide To a solution of 2.5 g of 3-(bromomethyl)phenyl 3-(hexadecyloxy)phenylphosphate in 20 ml of dry toluene was added 4.43 of quinoline followed by stirring in an inert atmosphere at 70° C. for 18 hours. The solvent was removed in vacuo and the residue stirred with 2.5 of Amberlite IR-4B resin in 50 ml of methyl alcohol for 2 hours. Filtered the mixture and removed the solvent in vacuo then columned the residue on silica gel with methyl alcohol-chloroform and methyl alcohol-chloroform-water. Triturated with ether and refrigerated giving 1.61 g of the desired compound as white amorphous powder.

EXAMPLE 7

1-[[3-[[[3-(Hexadecyloxy)phenoxy]hydroxyphosphinyl]-oxy]phenyl]methyl]-pyridinium, hydroxide inner salt To a solution of 2.5 g of 3-(bromomethyl)phenyl 3-(hexadecyloxy)phenyl phosphate in 22 ml of dry toluene was added 2.7 g of pyridine followed by stirring, in an inert atmosphere, at 70°–75° C. for 18 hours. The solvent was removed in vacuo and the residue stirred with 2.5 g of Amberlite IR-4B resin in 55 ml of methyl alcohol for 2 hours. Filtered the mixture and removed the solvent in vacuo. The residue was columned on silica gel with methyl alcohol-chloroform and methyl alcohol-chloroform-water. Triturated with ether and refrigerated giving 2.1 g of the desired compound as white amorphous powder.

EXAMPLE 8

3-[[2-[[[3-(Hexadecyloxy)phenoxy]hydroxyphosphinyl]oxy]phenyl]methyl]-thiazolium, hydroxide, inner salt A mixture of 4.5 g of 3-(hexadecyloxy)phenol, 2.75 g of 2-chloro-4H-1,3,2-benzodioxaphosphorin, 2-oxide and 2.06 ml of triethylamine in 60 ml of carbon tetrachloride was stirred for 18 hours. The mixture was diluted with ether, filtered and the solvent removed. The residue following solvent removal was heated in a pressure vessel (90° C.) with 10.08 g of triazole in 50 ml of toluene for 4 days. The solvent was removed in vacuo and the residue purified by chromatography on silica gel with methyl alcohol-chloroform and methyl alcohol-chloroform-water. Triturated with ether and refrigerated giving 2.2 g of the desired compound as white powder.

EXAMPLE 9

4-(Hexadecyloxy)phenol

To a suspension of 21.79 g of hexane washed sodium hydride in 155 ml of N,N-dimethylformamide was added dropwise over 1.5 hours a solution of 40.0 g of hydroquinone in 140 ml of N,N-dimethylformamide and 55 ml of tetrahydrofuran. The resulting mixture was cooled to 0° C. and 5.45 g of sodium iodide added, followed by the dropwise addition of 152.0 g of hexadecylbromide over 1.25 hours. The bath was removed and the mixture stirred at ambient temperature for 17 hours. The mixture was diluted with ice and 500 ml of cold dilute hydrochloric acid, extracted with ether and filtered. The ether layer was dried over sodium sulfate and evaporated to a syrup which was purified by chromatography on silica gel with ethyl acetate-hexanes giving 8.0 g of the desired compound as a white solid, m.p. 87°–88° C.

EXAMPLE 10

3-(Bromomethyl)phenyl 4-(hexadecyloxy)phenyl phosphate

To a solution of 1.0 g of 4-(hexadecyloxy)phenol in 10 ml of dry carbon tetrachloride and 2 ml of ether cooled in a water bath was added a solution of 1.1 g of 3-(bromomethyl)phenyl phosphodichlorodate in 2 ml of carbon tetrachloride in an inert atmosphere. A solution of 2.4 ml of triethylamine in 2 ml of carbon tetrachloride was rapidly added followed by cooling bath removal and stirring for 4 hours. The mixture was filtered through diatomaceous earth and evaporated to a residue which was stirred for two hours with 25 ml of tetrahydrofuran and 25 ml of 0.5M sodium acetate then refrigerated overnight. The tetrahydrofuran was removed under vacuum and the aqueous residue cooled and acidified with hydrochloric acid followed by ether extraction. The organic layer was washed with saturated sodium chloride, dried with magnesium sulfate and evaporated to a syrup which was purified by chromatography on magnesium silicate with chloroform and 10% methyl alcohol-chloroform giving 1.57 g of the desired compound as a glass.

EXAMPLE 11

3-[[3-[[[4-(Hexadecyloxy)phenoxy]hydroxyphosphinyl]-oxy]phenyl]methyl]thiazolium, hydroxide, inner salt To a solution of 1.5 g of 3-(bromomethyl)phenyl 4-(hexadecyloxy)phenyl phosphate in 15 ml of dry toluene was added 1.8 g of thiazole followed by stirring in an inert atmosphere, at 65°–70° C. for 18 hours. The solvent was removed in vacuo and the residue stirred with 1.5 of Amberlite ® IR-4B resin in 40 ml of methyl alcohol for 1.5 hours. The mixture was filtered and the solvent removed in vacuo. The residue was columned on silica gel with methyl alcohol-chloroform and methyl alcohol-chloroform-water. Triturated with ether and refrigerated giving 1.18 g of the desired compound as white amorphous powder.

EXAMPLE 12

3-(Hexadecyloxy)-2-methylphenol

To a suspension of 25.0 g of hexane washed sodium hydride in 215 ml of N,N-dimethylformamide was added dropwise over 1.5 hours a solution of 60.0 g of 2-methylresorcinol in 145 ml of N,N-dimethylformamide and 72 ml of tetrahydrofuran. The resulting mixture was cooled to 0° C. and 7.25 g of sodium iodide added followed by the dropwise addition of 152.0 g of hexadecylbromide over 1 hour. The bath was removed and the mixture stirred at ambient temperature for 18 hours. The mixture was diluted with 500 ml of iced dilute hydrochloric acid, extracted with ether and filtered. The ether layer was dried over magnesium sulfate and evaporated to an oil which was purified by chromatography on silica gel giving 54.5 g of the desired compound as a white solid, m.p. 53°–54° C.

EXAMPLE 13

3-(Bromomethyl)phenyl 3-(hexadecyloxy)-2-methylphenyl phosphate

To a solution of 5.0 g of 3-(hexadecyloxy)-2-methylphenol in 60 ml of dry carbon tetrachloride, cooled in an ice bath, was added a solution of 5.23 g of 3-(bromomethyl)phenyl phosphodichlorodate in 10 ml of carbon tetrachloride in an inert atmosphere. A solution of 2.4 ml of triethylamine in 10 ml of carbon tetrachloride was rapidly added followed by cooling bath removal and stirring overnight. Filtered the mixture through diatomaceous earth and evaporated to a residue which was stirred for two hours with 130 ml of tetrahydrofuran and 130 ml of 0.5M sodium acetate. The tetrahydrofuran was removed under vacuum and the aqueous residue cooled and acidified with hydrochloric acid followed by ether extraction. The organic layer was washed with saturated sodium chloride, dried with magnesium sulfate and evaporated to a syrup which was purified by chromatography on magnesium silicate with chloroform and 10% methyl alcohol-chloroform giving 6.5 g of the desired compound as a glass following solvent removal.

EXAMPLE 14

3-[[3-[[[3-(Hexadecyloxy)-2-methylphenoxy]hydroxy phosphinyl]oxy]phenyl]methyl]-thiazolium, hydroxide, inner salt To a solution of 2.3 g of 3-(bromomethyl)phenyl 3-(hexadecyloxy)-2-methylphenyl phosphate in 20 ml of dry toluene was added 2.62 g of thiazole followed by stirring, in an inert atmosphere, at 60°–65° C. for 18 hours. The solvent was removed in vacuo and the residue stirred with 2.3 g of Amberlite ® IR-4B resin in 60 ml of methyl alcohol for 2 hours. The mixture was filtered and the solvent was removed in vacuo. The residue was columned on silica gel with methyl alcohol-chloroform and methyl alcohol-chloroform-water. Triturated with ether and refrigerated giving 1.92 g of the desired compound as a white amorphous powder.

EXAMPLE 15

2-(Tetradecyloxy)phenol

To a mechanically stirred suspension of 29.6 g of hexane washed sodium hydride in 215 ml of N,N-dimethylformamide was added dropwise under argon over 1.5 hours a solution of 54.33 g of catechol in 145 ml of N,N-dimethylformamide and 72 ml of tetrahydrofuran. The resulting mixture was cooled to 0° C. and 7.4 g of sodium iodide added followed by the dropwise addition of 144.0 g of 1-bromotetradecane over 1 hour. The bath was removed and the mixture stirred at ambient temperature for 18 hours. The mixture was diluted with 500 ml of dilute hydrochloric acid, extracted with ether and filtered. The ether layer was dried over magnesium sulfate and evaporated to an oil which was purified by chromatography on silica gel giving 54.5 g of the desired compound as a white solid, m.p. 53°–54° C.

EXAMPLE 16

3-(Bromomethyl)phenyl 2-(tetradecyloxy) phenyl phosphate

To a solution of 1.0 g of 2-(tetradecyloxy)-phenol in 10 ml of dry carbon tetrachloride cooled in a water bath was added a solution of 1.19 g of 3-(bromomethyl)phenyl phosphodichlorodate in 2 ml of carbon tetrachloride in an inert atmosphere. A solution of 396 mg of triethylamine in 23 ml of carbon tetrachloride was rapidly added followed by cooling bath removal and stirring for 4 hours. Filtered the mixture through diatomaceous earth and evaporated to a residue which was stirred for 1.5 hours with 25 ml of tetrahydrofuran and 25 ml of 0.5M sodium acetate. The tetrahydrofuran was removed under vacuum and the aqueous residue cooled and acidified with hydrochloric acid followed by ether extraction. The organic layer was washed with saturated sodium chloride, dried with magnesium sulfate and evaporated to a syrup which was purified by chromatography on magnesium silicate with chloroform and 10% methyl alcohol-chloroform giving 1.75 g of the desired compound as a glass.

EXAMPLE 17

3-[[3-[[Hydroxy[2-(tetradecyloxy)phenoxy]phosphinyl]-oxy]phenyl]methyl]thiazolium, hydroxide, inner salt To a solution of 1.7 g of 3-(bromomethyl)phenyl 2-(tetradecyloxy)phenyl phosphate in 15 ml of dry toluene was added 2.08 g of thiazole followed by stirring, in an inert atmosphere, at 67° C. for 18 hours. The solvent was removed in vacuo after 48 hours and the residue stirred with 1.7 g of Amberlite ® IR-4B resin in 50 ml of methyl alcohol for 1 hour. The mixture was filtered and the solvent removed in vacuo. The residue was columned on silica gel with methyl alcohol-chloroform and methyl alcohol-chloroform-water. Triturated with ether and refrigerated giving 1.38 g of the desired compound as a white amorphous powder.

EXAMPLE 18

3-(Tetradecyloxy)phenol

To a suspension of 29.6 g of hexanes washed sodium hydride under argon in 215 ml of N,N-dimethylformamide was added dropwise over 1.5 hours a solution of 54.33 g of resorcinol in 145 ml of N,N-dimethylformamide and 72 ml of tetrahydrofuran. The resulting mixture was cooled to 0° C. and 7.4 g of sodium iodide added followed by the dropwise addition of 144.0 g of 1-bromotetradecane over 1 hour. The bath was allowed to melt and the mixture stirred for 2 days. The mixture was diluted with ice and 300 ml of cold dilute hydrochloric acid, extracted with ether and filtered. The ether layer was dried over magnesium sulfate and evaporated to an oil which was purified by chromatography on silica gel using ethyl acetatehexanes giving 40.8 g of the desired product as a white solid, m.p. 49°–50° C.

EXAMPLE 19

3-(Bromomethyl)phenyl 3-(tetradecyloxy)phenyl phosphate

To a solution of 2.0 g of 3-(tetradecyloxy)phenol in 25 ml of dry carbon tetrachloride cooled in an ice bath was added a solution of 2.43 g of 3-(bromomethyl)phenyl phosphodichlorodate in 5 ml of carbon tetrachloride in an inert atmosphere. A solution of 1.1 ml of triethylamine in 5 ml of carbon tetrachloride was rapidly added followed by cooling bath removal and stirring overnight. Filtered the mixture through diatomaceous earth and evaporated to a residue which was stirred for 1.5 hours with 55 ml of tetrahydrofuran and 55 ml of 0.5M sodium acetate. The tetrahydrofuran was removed under vacuum and the aqueous residue cooled and acidified with hydrochloric acid followed by ether extraction. The organic layer was washed with saturated sodium chloride, dried with magnesium sulfate and evaporated to a syrup which was purified by chromatography on magnesium silicate with chloroform and 10% methyl alcohol-chloroform giving 3.0 g of the desired compound as a glass.

EXAMPLE 20

3-[[3-[[Hydroxy[3-(tetradecyloxy)phenoxy]phosphinyl]-oxy]phenyl]methyl]thiazolium, hydroxide, inner salt To a solution of 1.5 g of 3-(bromomethyl)phenyl 3-(tetradecyloxy)phenyl phosphate in 15 ml of dry toluene was added 1.84 g of thiazole followed by stirring, in an inert atmosphere, at 65° C. for 18 hours. The solvent was removed in vacuo and the residue stirred with 1.5 g of Amberlite ® IR-4B resin in 40 ml of methyl alcohol for 1 hour. The mixture was filtered and the solvent removed in vacuo. The residue was columned on silica gel with methyl alcohol-chloroform and methyl alcohol-chloroform-water. Triturated with ether and refrigerated giving 1.01 g of the desired compound as a white amorphous powder.

EXAMPLE 21

3-[[3-[[Hydroxy[3-(tetradecyloxy)phenoxy]phosphinyl]-oxy]phenyl]methyl]-5-methyl-thiazolium, hydroxide, inner salt To a solution of 1.5 g of 3-(bromomethyl)phenyl 3-(tetradecyloxy)phenyl phosphate in 15 ml of dry toluene was added 2.14 g of 5-methylthiazole followed by stirring in an inert atmosphere at 65° C. for 17 hours. The solvent was removed in vacuo and the residue stirred with 1.5 g of Amberlite ® IR-4B resin in 40 ml of methyl alcohol for 1.5 hours. The mixture was filtered and the solvent removed in vacuo. The residue was columned on silica gel with methyl alcohol-chloroform and methyl alcohol-chloroform-water. Triturated with ether and refrigerated giving 1.06 g of the desired compound as a white amorphous powder.

EXAMPLE 22

2-Methoxy-3-(tetradecyloxy)phenol

To a suspension of 3.8 g of hexane washed sodium hydride in 25 ml of N,N-dimethylformamide was added dropwise over 1.5 hours a solution of 60.0 g of 2-methoxy resorcinol in 50 ml of N,N-dimethylformamide. The resulting mixture was cooled to 0° C. and 1.07 g of sodium iodide added followed by the dropwise addition of 19.79 g of 1-bromotetradecane over 20 minutes. The bath was removed and the mixture stirred at ambient temperature for 18 hours. The mixture was poured into dilute hydrochloric acid and extracted with ether. The ether layer was dried over magnesium sulfate and evaporated to an oil which was distilled using a Kugelrohr apparatus and the fraction boiling at 130°–180°/0.1 mm collected. Purification using high pressure liquid chromatography on silica gel using hexanes-ether gave 8.7 g of the desired compound as an oil.

EXAMPLE 23

3-(Bromomethyl)phenyl 2-methoxy-3-(tetradecyloxy) phenyl phosphate

To a solution of 8.0 g of 2-methoxy-3-(tetradecyloxy)phenol in 60 ml of dry carbon tetrachloride cooled in an ice bath was added a solution of 8.67 g of 3-bromomethyl)phenyl phosphodichlorodate in 10 ml of carbon tetrachloride in an inert atmosphere. A solution of 3.98 ml of triethylamine in 10 ml of carbon tetrachloride was rapidly added followed by cooling bath removal and stirring overnight. The mixture was filtered through diatomaceous earth and evaporated to a residue which was stirred for 1.5 hours with 250 ml of tetrahydrofuran and 250 ml of 0.5M sodium acetate. The tetrahydrofuran was removed under vacuum and the aqueous residue cooled and acidified with hydrochloric acid followed by ether extraction. The organic layer was washed with saturated sodium chloride, dried with magnesium sulfate and evaporated to a syrup which was purified by chromatography on magnesium silicate with chloroform and 10% methyl alcohol-chloroform giving 11.4 g of the desired compound as an oil.

EXAMPLE 24

3-[[3-[[Hydroxy]2-methoxy-3-(tetradecyloxy)phenoxy]-phosphinyl]oxy]phenyl]methyl]-thiazolium, hydroxide inner salt To a solution of 3.0 g of 3-(bromomethyl)phenyl)-2-methoxy-3-(tetradecyloxy)phenyl phosphate in 20 ml of dry toluene was added 2.62 g of thiazole followed by stirring, in an inert atmosphere, at 95° C. for 2.5 hours. The solvent was removed in vacuo and the residue stirred with 2.18 g of Amberlite ® IR-4B resin in 50 ml of methyl alcohol for 10 minutes. The mixture was filtered and the solvent removed in vacuo. The residue was columned on silica gel with methyl alcohol-chloroform and methyl alcohol-chloroform-water. Triturated with ether and refrigerated giving 1.73 g of the desired compound as a white amorphous powder.

EXAMPLE 25

3-[[3-[[Hydroxy[2-methoxy-3-(tetradecyloxy)phenoxy]-phosphinyl]oxy]phenyl]methyl]-5-methyl-thiazolium, hydroxide, inner salt To a solution of 1.8 g of 3-(bromomethyl)phenyl2-methoxy-3-(tetradecyloxy)phenyl phosphate in 15 ml of dry toluene was added 1.52 g of 5-methyl thiazole followed by stirring, in an inert atmosphere, at 80° C. for 5 hours. The solvent was removed in vacuo and the residue stirred with 5.0 g of Amberlite ® IR-4B resin in 60 ml of methyl alcohol for 1 hour. The mixture was filtered and the solvent removed in vacuo. The residue was columned on silica gel with methyl alcohol-chloroform and methyl alcohol-chloroform-water. Triturated with ether and refrigerated giving 0.93 g of the desired compound as a white amorphous powder.

EXAMPLE 26

1-[[3-[[Hydroxy[2-methoxy-3-(tetradecyloxy)phenoxy]-phosphinyl]oxy]phenyl]methyl]-pyridinium, hydroxide, inner salt To a solution of 2.3 g of 3-(bromomethyl)phenyl2-methoxy-3-(tetradecyloxy)phenyl phosphate in 15 ml of dry toluene was added 2.62 g of pyridine followed by stirring. in an inert atmosphere, at 60°-65° C. for 18 hours. The solvent was removed in vacuo and the residue stirred with 6.0 g of Amberlite ® IR-4B resin in 50 ml of methyl alcohol for 10 minutes. The mixture was filtered and the solvent removed in vacuo. The residue was columned on silica gel with methyl alcohol-chloroform and methyl alcohol-chloroform-water. Triturated with ether and refrigerated giving 1.4 g of the desired compound as a white amorphous powder.

EXAMPLE 27

1-[[3-[[Hydroxy[2-methoxy-3-(tetradecyloxy)phenoxy]-phosphinyl]oxy]phenyl]methyl]-quinolinium, hydroxide, inner salt To a solution of 2.0 g of 3-(bromomethyl)phenyl 2-methoxy-3-(tetradecyloxy)phenyl phosphate in 15 ml of dry toluene was added 2.21 g of quinoline followed by stirring, in an inert atmosphere, at 90° C. for 4 hours. The solvent was removed in vacuo and the residue stirred with 6.0 g of Amberlite ® IR-4B resin in 50 ml of methyl alcohol for 2 hours. The mixture was filtered and the solvent removed in vacuo. The residue was columned on silica gel with methyl alcohol-chloroform and methyl alcohol-chloroform-water. Triturated with ether and refrigerated giving 1.6 g of the desired compound as a white amorphous powder.

EXAMPLE 28

2-[[3-[[Hydroxy[2-methoxy-3-(tetradecyloxy)phenoxy]-phosphinyl]oxy]phenyl]methyl]-isoquinolinium, hydroxide, inner salt To a solution of 1.7 g of 3-(bromomethyl)phenyl 2-methoxy-3-(tetradecyloxy)phenyl phosphate in 15 ml of dry toluene was added 1.87 g of isoquinoline followed by stirring, in an inert atmosphere, at 80° C. for 5 hours. The solvent was removed in vacuo and the residue stirred with 3.0 g of Amberlite ® IR-4B resin in 60 ml of methyl alcohol for 15 minutes. The mixture was filtered and the solvent removed in vacuo. The residue was columned on silica gel with methyl alcohol-chloroform and methyl alcohol-chloroform-water. Triturated with ether and refrigerated giving 1.25 g of the desired product as a white amorphous powder.

EXAMPLE 29

Methyl 2-hydroxy-6-(tetradecyloxy)benzoate

To a suspension of 6.2 g of hexanes washed sodium hydride in 75 ml of N,N-dimethylformamide was added dropwise over 1.5 hours a solution of 20.0 g of methyl 2,6-dihydroxybenzoate in 50 ml of N,N-dimethylformamide and 24 ml of tetrahydrofuran. The resulting mixture was cooled to 0° C. and 1.78 g of sodium iodide added followed by the dropwise addition of 34.7 g of 1-bromotetradecane over 1 hour. The bath was removed and the mixture stirred at ambient temperature for 17 hours. The mixture was diluted with 500 ml of iced dilute hydrochloric acid, and extracted with ether. The ether layer was dried over magnesium sulfate and evaporated to an oil which was purified by chromatography on silica gel with ethyl acetate:hexanes giving an oil which was distilled in a Kugelrohr apparatus giving 3.0 g of the desired compound as a white solid, B.P. 130°-180° C.

EXAMPLE 30

Methyl 2-[[[3-(bromomethyl)phenoxy]hydroxyphosphinyl]-oxy]-6-(tetradecyloxy)benzoate To a solution of 2.9 g of methyl 2-hydroxy-6-(tetradecyloxy)benzoate in 35 ml of dry carbon tetrachloride cooled in an ice bath was added a solution of 2.9 g of 3-(bromomethyl)phenyl phosphodichlorodate in an inert atmosphere. A solution of 1.4 ml of triethylamine in 10 ml of carbon tetrachloride was rapidly added followed by cooling bath removal and stirring overnight. The mixture was filtered through diatomaceous earth and evaporated to a residue which was stirred for 1.5 hours with 70 ml of tetrahydrofuran and 70 ml of 0.5M sodium acetate. The tetrahydrofuran was removed under vacuum and the aqueous residue cooled and acidified with hydrochloric acid followed by ether extraction. The organic layer was washed with saturated sodium chloride, dried with magnesium sulfate and evaporated to a syrup which was purified by chromatography on magnesium silicate with chloroform and 10% methyl alcohol-chloroform giving 3.6 g of the desired compound as a glass.

EXAMPLE 31

3-[[3-[[Hydroxy[2-(methoxycarbonyl)-3-(tetradecyloxy)-phenoxy]phosphinyl]oxy]phenyl]methyl]-thiazolium, hydroxide, inner salt To a solution of 1.10 g of methyl 2-[[[3-(bromomethyl)phenoxy]hydroxyphosphinyl]oxy]-6-(tetradecyloxy)-benzoate in 15 ml of dry toluene was added 1.31 g of thiazole followed by stirring, in an inert atmosphere, at 65°-70° C. for 17 hours. The solvent was removed in vacuo and the residue stirred with 1.26 g of Amberlite ® IR-4B resin in 50 ml of methyl alcohol for 2 hours. The mixture was filtered and the solvent removed in vacuo. The residue was columned on silica gel with methyl alcohol-chloroform and methyl alcohol-chloroform-water. Triturated with ether and refrigerated giving 532 mg of the desired compound as a white amorphous glass.

EXAMPLE 32

3-[[3-[[Hydroxy[2-(methoxycarbonyl)-3-(tetradecyloxy) phenoxy]phosphinyl]oxy]phenyl]methyl]-5-methylthiazolium, hydroxide, inner salt To a solution of 1.18 g of methyl 2-[[[3-(bromomethyl)phenoxy]hydroxyphosphinyl]oxy]-6-(tetradecyloxy)benzoate in 15 ml of dry toluene was added 1.53 g of 5-methylthiazole followed by stirring, in an inert atmosphere, at 65°-70° C. for 17 hours. The solvent was removed in vacuo and the residue stirred with 1.2 g of Amberlite ® IR-4B resin in 50 ml of methyl alcohol for 2 hours. The mixture was filtered and the solvent removed in vacuo. The residue was columned on silica gel with methyl alcohol-chloroform and methyl alcohol-chloroform-water. Triturated with ether and refrigerated giving 0.783 g of the desired compound as a white amorphous glass.

EXAMPLE 33

1-[[3-Hydroxy[2-(methoxycarbonyl)-3-(tetradecyloxy)-phenoxy]phosphinyl]oxy]phenyl]methyl]quinolinium, hydroxide, inner salt To a solution of 1.18 g of methyl 2-[[[3-(bromomethyl)phenoxy]hydroxyphosphinyl]oxy]-6-(tetradecyloxy)-benzoate in 15 ml of dry toluene was added 1.99 g of quinoline followed by stirring, in an inert atmosphere, at 65°-70° C. for 17 hours. The solvent was removed in vacuo and the residue stirred with 1.2 g of Amberlite ® IR-4B resin in 50 ml of methyl alcohol for 1.5 hours. The mixture was filtered and the solvent removed in vacuo. The residue was columned on silica gel with methyl alcohol-chloroform and methyl alcohol-chloroform-water. Triturated with ether and refrigerated giving 0.846 g of the desired compound as a white powdered glass.

EXAMPLE 34

3-(Tetradecyloxy)benzyl alcohol

A mixture of 66 g of 3-hydroxyphenethyl alcohol, 147.43 g of 1-bromotetradecane, 27.65 g of sodium hydroxide and 2.15 g of trioctylmethyl ammonium chloride in 400 ml of toluene was refluxed for 42 hours. The mixture was washed with water and the organic layer dried with magnesium sulfate. The solvent was removed in vacuo and the warm concentrate poured into 1 liter of hexanes. The resulting solid was washed with cold hexanes then dried giving 998.6 g of the desired compound as a white solid.

EXAMPLE 35

Methyl 3-(bromomethyl)phenyl[3-(tetradecyloxy) phenyl phosphate

To a solution of 9.0 g 3-(tetradecyloxy)benzyl alcohol in 60 ml of dry carbon tetrachloride cooled in an ice bath was added a solution of 10.24 g of 3-(bromomethyl)phenyl phosphodichlorodate in 10 ml of carbon tetrachloride in an inert atmosphere. A solution of 4.7 ml of triethylamine in 10 ml of carbon tetrachloride was rapidly added followed by cooling bath removal and stirring for 4 hours. The mixture was filtered through diatomaceous earth and evaporated to a residue which was stirred for 1 hour with 150 ml of tetrahydrofuran and 150 ml of 0.5M sodium acetate. The tetrahydrofuran was removed under vacuum and the aqueous residue cooled and acidified with hydrochloric acid followed by ether extraction. The organic layer was washed with saturated sodium chloride, dried with magnesium sulfate and evaporated to a syrup which was purified by chromatography on magnesium silicate with chloroform and 10% methyl alcohol-chloroform giving 12.5 g of the desired compound as a glass.

EXAMPLE 36

3-[[3-[[Hydroxy[[3-(tetradecyloxy)phenyl]methoxy]-phosphinyl]oxy]phenyl]methyl]thiazolium, hydroxide, inner salt To a solution of 3.0 g of methyl 3-[(tetradecyloxy)-benzyl alcohol in 20 ml of dry toluene was added 1.1 g of thiazole followed by stirring, in an inert atmosphere, at 65°-75° C. for 2 days. The solvent was removed in vacuo and the residue stirred with 3.0 g of Amberlite ® IR-4B resin in 40 ml of methyl alcohol for 2 hours. The mixture was filtered and the solvent removed in vacuo. The residue was columned on silica gel with methyl alcohol-chloroform and methyl alcohol-chloroform-water. Triturated with ether and refrigerated giving 0.4 g of the desired compound as a white amorphous powder.

EXAMPLE 37

3-Methoxy-1-tetradecyl-benzene

A 4.87 g portion of magnesium was placed in a two-necked round bottom flask. The flask was flamed several times and 37.4 g of m-bromoanisole and 200 ml of tetrahydrofuran were added. As soon as the reaction stopped it was refluxed for 1 hour and then added to a boiling solution of 52.68 g of tetradecyl bromide in tetrahydrofuran. Then 10 ml of lithium cupric chloride was added and the mixture was refluxed for 1.25 hours, stirred at room temperature for 16 hours, quenched with water, washed with ammonium chloride solution, brine, dried and the solvent removed. The resulting oily residue was distilled in a Kugelrohr apparatus giving 52.4 g of the desired compound as a clear oil, B.P. (120°/0.5 mm).

EXAMPLE 38

3-Tetradecylphenol

To a solution of 136.8 g of 3-methoxy-1-tetradecyl-benzene in 600 ml of methylene chloride, cooled to −78° C., under inert gas, was added dropwise a solution of 112.8 g of boron tribromide in 100 ml of methylene chloride. The mixture was kept at −78° C. for 1 hour then allowed to warm slowly to room temperature followed by stirring for 16 hours. The mixture was cooled to 0° C. and cold water added dropwise. The organic layer was separated and washed with aqueous sodium bicarbonate, dried and the solvent evaporated. The residue was poured onto crushed ice and 107 g of the desired product collected as a white solid, m.p. 38°-40° C.

EXAMPLE 39

3-(Bromomethyl)phenyl 3-(tetradecyl)phenyl phosphate

A mixture of 1.5 g of 3-tetradecylphenol, 1.88 g of 3-(bromomethyl)phenyl phosphodichlorodate and 627 mg of triethylamine in 15 ml of carbon tetrachloride was stirred at room temperature for 4 hours and filtered. The solvent was removed in vacuo and the residue stirred with 60 ml of 0.5M sodium acetate and 60 ml of tetrahydrofuran for 1.5 hours. The mixture was poured into dilute hydrochloric acid and extracted with ether. The ether layer was washed with water, dried with magnesium sulfate and filtered through a column of magnesium silicate giving 1.5 g of the desired product as an oil.

EXAMPLE 40

3-[[3-[[Hydroxy(3-tetradecylphenoxy)phosphinyl]oxy]phenyl]methyl]thiazolium, hydroxide, inner salt A mixture of 1.5 g of 3-(bromomethyl)phenyl 3-(tetradecyl)phenyl phosphate and 1.89 g of thiazole was heated in 10 ml of toluene under an inert atmosphere for 2 hours. The solvent was removed in vacuo and the residue purified by chromatography on silica gel using methyl alcohol-chloroform and methyl alcohol-chloroform-water. Triturated with ether and refrigerated giving 0.7 g of white powder.

EXAMPLE 41

3-(Dodecyloxy)phenol

To a suspension of 24.67 g of hexanes washed sodium hydride in 215 ml of N,N-dimethylformamide was added dropwise over 1.5 hours a solution of 54.33 g of resorcinol in 145 ml of N,N-dimethylformamide and 72 ml of tetrahydrofuran. The resulting mixture was cooled to 0° C. and 7.4 g of sodium iodide added followed by the dropwise addition of 122.98 g of 1-bromododecane over 1 hour. The bath was removed and the mixture stirred at ambient temperature for 17 hours. The mixture was diluted with 500 ml of cold dilute hydrochloric acid and extracted with ether. The ether layer was dried over magnesium sulfate and evaporated to a low volume and filtered. The filtrate was concentrated to a reddish oil and purified by chromatography on silica gel using ethyl acetate-hexanes to give 36 g of the desired compound as buff colored crystals, m.p. 42°-43° C.

EXAMPLE 42

3-(Bromomethyl)phenyl 3-(dodecyloxy)phenyl phosphate

To a solution of 727 mg of 3-(dodecyloxy)phenol in 8 ml of dry carbon tetrachloride cooled in an ice bath was added a solution of 952 mg of 3-(bromomethyl)phenyl phosphodichlorodate in 2 ml of carbon tetrachloride in an inert atmosphere. A solution of 317 mg of triethylamine in 2 ml of carbon tetrachloride was rapidly added followed by cooling bath removal and stirring overnight. Added 10 ml of toluene and filtered the mixture through diatomaceous earth. Evaporated the filtrate to a residue which was stirred for 1.5 hours with 20 ml of tetrahydrofuran and 20 ml of 0.5M sodium acetate. The tetrahydrofuran was removed under vacuum and the aqueous residue cooled and acidified with hydrochloric acid followed by ether extraction. The organic layer was washed with saturated sodium chloride, dried with magnesium sulfate and evaporated to a syrup which was purified by chromatography on magnesium silicate with chloroform and 10% methyl alcohol-chloroform giving 1.05 g of the desired compound as a glass.

EXAMPLE 43

3-[[3-[[[3-(Dodecyloxy)phenoxy]hydroxyphosphinyl]oxy]phenyl]methyl]thiazolium, hydroxide, inner salt To a solution of 1.0 g of 3-(bromomethyl)phenyl 3-(dodecyloxy)phenyl phosphate in 15 ml of dry toluene was added 1.29 g of thiazole followed by stirring, in an inert atmosphere, at 68° C. for 18 hours. The solvent was removed in vacuo and the residue stirred with 1.0 g of Amberlite® IR-4B resin in 30 ml of methyl alcohol for 1.5 hours. The mixture was filtered and the solvent removed in vacuo. The residue was columned on silica gel with methyl alcohol-chloroform and methyl alcohol-chloroform-water. Triturated with ether and refrigerated giving 760 mg of the desired compound as white amorphous powder.

EXAMPLE 44

3-(Dodecyloxy)-2-methoxyphenol

To a suspension of 3.8 g of hexanes washed sodium hydride in 25 ml of N,N-dimethylformamide, cooled to 0° C. in an inert atmosphere was added a solution of 10 g of 2-methoxy resorcinol in 50 ml of N,N-dimethylformamide dropwise over 20 minutes. Added 1.07 g of sodium iodide followed by the dropwise addition of a solution of 19.8 g of 1-bromododecane in 25 ml of N,N-dimethylformamide over 20 minutes. The bath was removed and the mixture stirred at ambient temperature for 18 hours. Added chips of ice followed by iced dilute hydrochloric acid. The mixture was extracted with ether and the organic layer dried with magnesium sulfate and the solvent evaporated to an oil which was distilled in a Kugelrohr apparatus giving 10 g of an oil, B.P. 120°-180°/0.1 mm. The oil was purified by chromatography on silica gel using ether-hexanes giving 7.7 g of the desired product as an oil following solvent removal.

EXAMPLE 45

3-(Bromomethyl)phenyl 3-(dodecyloxy)-2-(methoxy) phenyl phosphate

To a solution of 7.2 g of 3-(dodecyloxy)-2-methoxyphenol in 45 ml of carbon tetrachloride was added 9.22 g of 3-(bromomethyl)phenyl phosphodichlorodate. The mixture was cooled to 0° C. under inert gas and 3.07 g of triethylamine in 10 ml of carbon tetrachloride carefully added dropwise. The cooling bath was removed and the mixture stirred at ambient temperature for 18 hours The mixture was filtered through diatomaceous earth and the filtrate taken to dryness. The residue was stirred with 225 ml of tetrahydrofuran and 225 ml of 0.5M sodium acetate at room temperature for 2 hours. The tetrahydrofuran was removed in vacuo and the aqueous residue cooled to 0° C. and acidified with hydrochloric acid followed by ether extraction. The organic layer was dried with magnesium sulfate and the solvent removed to afford a thick oil, which was purified by chromatography on magnesium silicate with chloroform and methyl alcohol-chloroform giving 8.1 g of the desired product as a glass.

EXAMPLE 46

1-[[3-[[[3-(Dodecyloxy)-2-methoxyphenoxy]hydroxyphosphinyl]oxy]phenyl]methyl]quinolinium, hydroxide, inner salt To a solution of 2 g of 3-(bromomethyl)phenyl 3-(dodecyloxy)-2-methoxyphenyl phosphate in 15 ml of dry toluene was added 3.7 g of quinoline followed by stirring, in an inert atmosphere, at 65°-ζ° C. for 18 hours. The solvent was removed in vacuo and the residue stirred with 3.0 g of Amberlite ® IR-4B resin in 50 ml of methyl alcohol for 1 hour. The mixture was filtered and the solvent removed in vacuo. The residue was columned on silica gel with methyl alcohol-chloroform and methyl alcohol-chloroform-water. Triturated with ether and refrigerated giving 1.36 g of the desired compound as a white amorphous powder.

EXAMPLE 47

3-[[3-[[[3-(Dodecyloxy)-2-methoxyphenoxy]hydroxyphosphinyl]oxy]phenyl]methyl]thiazolium, hydroxide, inner salt To a solution of 2 g of 3-(bromomethyl)phenyl 3-(dodecyloxy)-2-(methoxy)phenyl phosphate in 15 ml of dry toluene was added 2.44 g of thiazole followed by stirring, in an inert atmosphere, at 65°-70° C. for 24 hours. The solvent was removed in vacuo and the residue stirred with 3.0 g of Amberlite ® IR-4B resin in 50 ml of methyl alcohol for 2 hours. The mixture was filtered and the solvent removed in vacuo. The residue was columned on silica gel with methyl alcohol-chloroform and methyl alcohol-chloroform-water. Triturated with ether and refrigerated giving 1.13 g of the desired compound as a yellow-orange glass.

EXAMPLE 48

4,6-Bis(1,1-dimethylethyl)-3-(dodecyloxy)phenol

To a suspension of 21.04 g of hexanes washed sodium hydride in 200 ml of N,N-dimethylformamide under argon was added 5.06 g of sodium iodide followed by the dropwise addition of 75 g of 4,6-di-t-butyl resorcinol dissolved in 200 ml of N,N-dimethylformamide and 150 ml of tetrahydrofuran over 1 hour. Over a 30 minute period, 84.1 g of 1-bromododecane was added dropwise followed by stirring for 18 hours. The mixture was poured into water and extracted with ether. The organic layer was washed with water and dried with magnesium sulfate. The solvent was evaporated and the oily concentrate distilled to give 38 g of the desired compound as an orange oil, B.P. 180°-205° C./0.5 mm.

EXAMPLE 49

2,4-Bis(1,1-dimethylethyl)-5-(dodecyloxy)phenyl 3-(bromomethyl)phenyl phosphate

To a solution of 2.0 g of 4,6-bis(1,1-dimethylethyl)-3-(dodecyloxy)phenol in 30 ml of dry carbon tetrachloride cooled in an ice bath was added a solution of 1.9 g of 3-(bromomethyl)phenyl phosphodichlorodate in an inert atmosphere. A solution of 0.9 ml of triethylamine in 5 ml of carbon tetrachloride was rapidly added followed by cooling bath removal and stirring overnight. The mixture was filtered through diatomaceous earth and evaporated to a residue which was stirred for 1.5 hours with 65 ml of tetrahydrofuran and 65 ml of 0.5M sodium acetate. The tetrahydrofuran was removed under vacuum and the aqueous residue cooled and acidified with hydrochloric acid followed by ether extraction. The organic layer was washed with saturated sodium chloride, dried with magnesium sulfate and evaporated to a syrup which was purified by chromatography on magnesium silicate with chloroform and 10% methyl alcohol-chloroform giving 1.4 g of the desired compound as a glass.

EXAMPLE 50

3-[[3-[[[2,4-Bis(1,1-dimethylethyl)-5-(dodecyloxy)phenoxy]hydroxyphosphinyl]oxy]phenyl]methyl]thiazolium, hydroxide, inner salt To a solution of 1.35 g of 2,4-bis(1,1-dimethylethyl)-5-(dodecyloxy)phenyl 3-(bromomethyl)phenyl phosphate in 15 ml of dry toluene was added 1.44 g of thiazole followed by stirring, in an inert atmosphere, at 65°-70° C. for 17 hours. The solvent was removed in vacuo and the residue stirred with 1.5 g of Amberlite ® IR-4B resin in 50 ml of methyl alcohol for 2 hours. The mixture was filtered and the solvent removed in vacuo. The residue was columned on silica gel with methyl alcohol-chloroform and methyl alcohol-chloroform-water. Triturated with ether and refrigerated giving 0.643 g of the desired compound as beige amorphous powder.

EXAMPLE 51

2,5-Bis(1,1-dimethylethyl)-4-(dodecyloxy)phenol

To a suspension of 42.08 g of hexanes washed sodium hydride, under inert gas, in 400 ml of N,N-dimethylformamide was added 10.12 g of sodium iodide. While stirring, a solution of 150 g of 2,5-di-tert-butylhydroquinone in 400 ml of N,N-dimethylformamide and 300 ml of tetrahydrofuran was added dropwise over 1.5 hours. Over an additional 30 minutes, 168.16 g of 1-bromododecane was added dropwise. Stirring was continued at ambient temperature for 24 hours. The mixture was diluted with crushed ice and cold dilute hyrochloric acid followed by ether extraction. The organic layer was dried with magnesium sulfate and the solvent removed in vacuo to afford a syrup which was distilled in a Kugelrohr apparatus. The fraction boiling 160°-205° C. was collected and purified by chromatography on silica gel with ether-hexanes giving 23.6 g of the desired compound as an orange oil.

EXAMPLE 52

2,5-Bis(1,1-dimethylethyl)-4-(dodecyloxy)phenyl 3-(bromomethyl)phenyl phosphate

To a solution of 2.0 g of 2,5-bis(1,1-dimethylethyl)-4-(dodecyloxy)phenol in 30 ml of dry carbon tetrachloride cooled in an ice bath was added a solution of 1.9 g of 3-(bromomethyl)phenyl phosphodichlorodate in an inert atmosphere. A solution of 0.9 ml of triethylamine in 10 ml of carbon tetrachloride was rapidly added followed by cooling bath removal and stirring for 4 hours. The mixture was filtered through diatomaceous earth and evaporated to a residue which was stirred for two hours with 65 ml of tetrahydrofuran and 65 ml of 0.5M sodium acetate. The tetrahydrofuran was removed under vacuum and the aqueous residue cooled and acidified with hydrochloric acid followed by ether extraction. The organic layer was washed with saturated sodium chloride, dried with magnesium sulfate and evaporated to a syrup which was purified by chromatography on magnesium silicate with chloroform and 10% methyl alcohol-chloroform giving 2.0 g of the desired product as a glass.

EXAMPLE 53

3-[[3-[[[2,5-Bis(1,1-dimethylethyl)-4-(dodecyloxy) phenoxy]hydroxyphosphinyl]oxy]phenyl]methyl]-thiazolium, hydroxide, inner salt To a solution of 1.95 g of 2,5-bis(1,1-dimethylethyl)-4-(dodecyloxy)phenyl 3-(bromomethyl)phenyl phosphate in 15 ml of dry toluene was added 2.0 g of thiazole followed by stirring, in an inert atmosphere, at 65°–70° C. for 18 hours. The solvent was removed in vacuo and the residue stirred with 2.0 g of Amberlite ® IR-4B resin in 60 ml of methyl alcohol for 2 hours. The mixture was filtered and the solvent removed in vacuo. The residue was columned on silica gel with methyl alcohol-chloroform and methyl alcohol-chloroform-water. Triturated with ether and refrigerated giving 0.83 g of the desired compound as an amorphous solid.

EXAMPLE 54

3-[[3-[[[2,5-Bis(1,1-dimethylethyl)-4-(dodecyloxy)-phenoxy] hydroxyphosphinyl]oxy]phenyl]methyl]-5-methyl-thiazolium, hydroxide, inner salt To a solution of 1.4 g of 2,5-bis(1,1-dimethylethyl)-4-(dodecyloxy)phenyl 3-(bromomethyl)phenyl phosphate in 15 ml of dry toluene was added 1.8 g of 5-methylthiazole followed by stirring, in an inert atmosphere, at 70° C. for 24 hours. The solvent was removed in vacuo and the residue stirred with 1.5 g of Amberlite ® IR-4B resin in 40 ml of methyl alcohol for 1.5 hours. The mixture was filtered and the solvent removed in vacuo. The residue was columned on silica gel with methyl alcohol-chloroform and methyl alcohol-chloroform-water. Triturated with ether and refrigerated giving 0.56 g of the desired compound as a white amorphous glass.

EXAMPLE 55

1-[[3-[[[2,5-Bis(1,1-dimethylethyl)-4-(dodecyloxy)-phenoxy] hydroxyphosphinyl]oxy]phenyl]methyl]quinolinium, hydroxide, inner salt To a solution of 1.4 g of 2,5-bis(1,1-dimethylethyl)-4-(dodecyloxy)phenyl 3-(bromomethyl)phenyl phosphate in 15 ml of dry toluene was added 2.3 g of quinoline followed by stirring, in an inert atmosphere, at 70° C. for 24 hours. The solvent was removed in vacuo and the residue stirred with 1.5 g of Amberlite ® IR-4B resin in 40 ml of methyl alcohol for 1.5 hours. The mixture was filtered and the solvent removed in vacuo. The residue was columned on silica gel with methyl alcohol-chloroform and methyl alcohol-chloroform-water. Triturated with ether and refrigerated giving 1.04 g of the desired product as a hard glass.

EXAMPLE 56

7-(Dodecyloxy)-2-naphthalenol

To a suspension of 19.47 g of hexane washed sodium hydride in 200 ml of N,N-dimethylformamide was added dropwise over 1 hour a solution of 50.0 g of 2,7-dihyroxynaphthalene in 100 ml of N,N-dimethylformamide and 200 ml of tetrahydrofuran. The resulting mixture was cooled to 0° C. and 7.25 g of sodium iodide added followed by the dropwise addition of 92.47 g of 1-iodododecane over 1 hour. The bath was removed and the mixture heated at 60° C. then stirred at ambient temperature for 18 hours. The mixture was diluted with 500 ml of dilute hydrochloric acid and extracted with ether. The ether layer was dried over magnesium sulfate and evaporated to an oil which was distilled in a Kugelrohr apparatus and the fraction boiling from 170°–250° C./3 mm collected as a solid followed by crystallization from methyl alcohol then hexane giving 10.1 g of the desired compound as a white solid.

EXAMPLE 57

3-(Bromomethyl)phenyl 7-(dodecyloxy)-2-naphthalenyl phosphate

To a solution of 0.22 g of 7-(dodecyloxy)-2-naphthalenol in 5 ml of dry carbon tetrachloride was added 0.244 g of 3-(bromomethyl)phenyl phosphodichlorodate in an inert atmosphere. A solution of 0.12 ml of triethylamine in 1 ml of carbon tetrachloride was rapidly added followed by stirring at ambient temperature for 4 hours and refrigeration for two days. The mixture was filtered through diatomaceous earth and evaporated to a residue which was stirred for two hours with 20 ml of tetrahydrofuran and 20 ml of 0.5M sodium acetate. The tetrahydrofuran was removed under vacuum and the aqueous residue cooled and acidified with hydrochloric acid followed by ether extraction. The organic layer was washed with saturated sodium chloride, dried with magnesium sulfate and evaporated giving the desired compound as a syrup.

EXAMPLE 58

3-[[3-[[[[7-(dodecyloxy)-2-naphthalenyl]oxy]hydroxyphosphinyl]oxy]phenyl]methyl]thiazolium, hydroxide, inner salt To a solution of 0.22 g of 7-bis(dodecyloxy)-2-naphthalenol in 5 ml of dry toluene was added 0.5 g of thiazole followed by stirring, in an inert atmosphere, at 65°–70° C. for 18 hours and allowed to stand at ambient temperature for 2 days. The solvent was removed in vacuo and the residue stirred with 500 mg of Amberlite ® IR-4B resin in 20 ml of methyl alcohol for 1.5 hours. The mixture was filtered and the solvent removed in vacuo. The residue was columned on silica gel with methyl alcohol-chloroform and methyl alcohol-chloroform-water. Triturated with ether and refrigerated giving 234 mg of the desired compound as a white amorphous powder.

EXAMPLE 59

3-[[3-[[(3-Chlorophenoxy)hydroxyphosphinyl]oxy]phenyl] methyl]thiazolium, hydroxide, inner salt A mixture of 3 g of 3-chlorophenol and 7.09 g of 3-(bromomethyl)phenyl phosphodichlorodate in 50 ml of carbon tetrachloride was stirred while 2.83 g of triethylamine was added. Stirring was continued for 5 hours then diluted with ether and filtered. The solvent was removed in vacuo and the residue stirred for 2 hours with 250 ml of 0.5M sodium acetate and 250 ml of tetrahydrofuran. The tetrahydrofuran was removed in vacuo and the aqueous residue acidified with hydrochloric acid followed by ether extraction. The organic layer was dried with magnesium sulfate and the solvent evaporated. The residue was heated with 9.93 g of thiazole in 50 ml of toluene in an inert atmosphere at 85° C. for 5 hours, cooled to ambient temperature and the toluene decanted from the precipitated oil. The oil was dissolved in 150 ml of warm methyl alcohol and stirred with 20 g of Amberlite ® IR-45 and 4 ml of water for 20 minutes. The mixture was filtered and the solvent evaporated. The residue was chromatographed on silica gel using chloroform-methanol-water. Evaporation of the fractions and triturated with ether followed by centrifuging gave 3.7 g of the desired product as a white powder.

EXAMPLE 60

3-(Bromomethyl)phenyl 4-chlorophenyl phosphate

To a solution of 2 g of 4-chlorophenol in 35 ml of carbon tetrachloride was added 5.2 g of 3-(bromomethyl)-phenyl phosphodichlorodate. The mixture was cooled to 0° C. under inert gas and 2.6 g of triethylamine carefully added. The cooling bath was removed and the mixture stirred at ambient temperature for 5 hours followed by standing in a refrigerator for 18 hours. The mixture was filtered through diatomaceous earth and the filtrate taken to dryness. The residue stirred with 165 ml tetrahydrofuran and 165 ml of 0.5M sodium acetate at room temperature for 2 hours. The tetrahyrofuran was removed in vacuo and the aqueous residue cooled to 0° C. and acidified with hydrochloric acid followed by ether extraction. The organic layer was dried with magnesium sulfate and the solvent removed to afford a thick oil which was purified by chromatography on magnesium silicate with chloroform and methyl alcohol-chloroform giving 3.9 g of the desired product as a glass.

EXAMPLE 61

1-[[3-[[(4-Chlorophenoxy)hydroxyphosphinyl]oxy] phenyl]methyl]quinolinium, hydroxide, inner salt To a solution of 1.3 g of 3-(bromoethyl)phenyl 4-chlorophenyl phosphate in 15 ml of dry toluene was added 3.56 g of quinoline followed by stirring, in an inert atmosphere, at 70° C. for 72 hours. The solvent was removed in vacuo and the residue stirred with 2.0 g Amberlite ® IR-4B resin in 50 ml of methyl alcohol for 2 hours. The mixture was filtered and the solvent removed in vacuo. The residue was columned on silica gel with methyl alcohol-chloroform and methyl alcohol-chloroform-water. Triturated with ether and refrigerated giving 7.1 mg of the desired compound as a white amorphous solid.

EXAMPLE 62

3-[[3-[[(4-Chlorophenoxy)hydroxyphosphinyl]oxy] phenyl]methyl]thiazolium, hydroxide, inner salt To a solution of 1.3 g of 4-chlorophenyl phosphate in 15 ml of dry toluene was added 2.34 g of thiazole followed by stirring, in an inert atmosphere, at 70° C. for 17 hours. The solvent was removed in vacuo and the residue stirred with 2.0 g of Amberlite ® IR-4B resin in 50 ml of methyl alcohol for 1.5 hours. The mixture was filtered and the solvent removed in vacuo. The residue was columned on silica gel with methyl alcohol-chloroform and methyl alcohol-chloroform-water. Triturated with ether and refrigerated giving 0.53 g of the desired compound as a white amorphous solid.

EXAMPLE 63

3-(Bromomethyl)phenyl-2-chlorophenyl phosphate

To a solution of 2 g of 2-chlorophenol in 35 ml of carbon tetrachloride was added 5.2 g of 3-(bromomethyl)-phenyl phosphodichlorodate. The mixture was cooled to 0° C. under inert gas and 2.6 ml of triethylamine carefully added. The cooling bath was removed and the mixture stirred at ambient temperature for 5 hours followed by standing in a refrigerator for 18 hours. The mixture was filtered through diatomaceous earth and the filtrate taken to dryness. The residue stirred with 165 ml tetrahydrofuran and 165 ml of 0.5M sodium acetate at room temperature for 2 hours. The tetrahyrofuran was removed in vacuo and the aqueous residue cooled to 0° C. and acidified with hydrochloric acid followed by ether extraction. The organic layer was dried with magnesium sulfate and the solvent removed to afford a thick oil, which was purified by chromatography on magnesium silicate with chloroform and methyl alcohol-chloroform giving 3.8 g of the desired product as an oil.

EXAMPLE 64

3-[[3-[[2-Chlorophenoxy)hydroxyphosphinyl]oxy] phenyl]methyl]thiazolium, hydroxide, inner salt To a solution of 1.3 g of 3-(bromomethyl)phenyl-2-chlorophenyl phosphate in 15 ml of dry toluene was added 2.34 g of thiazole followed by stirring, in an inert atmosphere, at 70° C. for 17 hours. The solvent was removed in vacuo and the residue stirred with 2.0 g of Amberlite ® IR-4B resin in 50 ml of methyl alcohol for 1.5 hours. The mixture was filtered and the solvent removed in vacuo. The residue was columned on silica gel with methyl alcohol-chloroform and methyl alcohol-chloroform-water. Triturated with ether and refrigerated giving 377 mg of the desired compound as a white amorphous solid.

EXAMPLE 65

1-[[3-[[(2-Chlorophenoxy)hydroxyphosphinyl]oxy] phenyl]methyl]quinolinium, hydroxide, inner salt To a solution of 1.3 g of 3-(bromomethyl)phenyl-2-chlorophenyl phosphate in 15 ml of dry toluene was added 3.56 g of quinoline followed by stirring, in an inert atmosphere, at 70° C. for 72 hours. The solvent was removed in vacuo and the residue stirred with 2.0 g of Amberlite ® IR-4B resin in 50 ml of methyl alcohol for 2 hours. The mixture was filtered and the solvent removed in vacuo. The residue was columned on silica gel with methyl alcohol-chloroform and methyl alcohol-chloroform-water. Triturated with ether and refrigerated giving 743 mg of the desired compound as an amorphous solid.

EXAMPLE 66

3-[[3-[[([1,1'-Biphenyl]-3-yloxy)hydroxyphosphinyl] oxy]phenyl]methyl]thiazolium, hyroxide, inner salt A mixture of 3.0 g of 3-phenylphenol and 5.36 g of 3-(bromomethyl)phenyl phosphodichlorodate in 50 ml of carbon tetrachloride was stirred while 2.14 g of triethylamine was added. Stirring was continued for 4 hours, diluted with ether and filtered. The ether was removed and the residue stirred for 2 hours with 200 ml of 0.5M sodium acetate and 200 ml of tetrahydrofuran. The tetrahydrofuran was removed in vacuo and the aqueous residue acidified with hydrochloric acid followed by ether extraction. The organic layer was dried with magnesium sulfate and the solvent evaporated. The residue was heated with 7.5 g of thiazole in 45 ml of toluene in an inert atmosphere at 85° C. for 4 hours followed by cooling. The toluene was decanted and the residue slurried with 150 ml of hot methyl alcohol followed by the addition of 20 g of Amberlite ® IR-45 resin. After stirring for 30 minutes, the mixture was filtered and the solvent evaporated. The residue was chromatographed on silica gel using chloroform-methanol-water giving 2.2 g of the desired product as a white powder following stirring with ether, filtering and drying.

EXAMPLE 67

3-[[3-[[Hydroxy[4-(phenylmethoxy)phenoxy]phosphinyl] oxy]phenyl]methyl]-5-methyl-thiazolium, hydroxide, inner salt A mixture of 3.g of 4-(benzyloxy)phenol and 4.6 g of 3-(bromomethyl)phenyl phosphodichlorodate in 50 ml of carbon tetrachloride was stirred while 1.8 g of triethylamine was added. Stirring was continued for 5 hours, diluted with ether and filtered. The ether was removed and the residue stirred for 3 hours with 200 ml of 0.5M sodium acetate and 200 ml of tetrahydrofuran. The tetrahydrofuran was removed in vacuo and the aqueous residue acidified with hydrochloric acid followed by ether extraction. The organic layer was dried with magnesium sulfate and the solvent evaporated. The residue was heated with 6.38 g of 5-methyl thiazole in 45 ml of toluene under an inert atmosphere at 85° C. for 5 hours. The mixture was cooled and the toluene decanted. The residue was dissolved in 200 ml of methyl alcohol and stirred with 20 g of Amberlite ® IR-45 resin. After stirring for 30 minutes, the mixture was filtered and the solvent evaporated. The residue was chromatographed on silica gel using chloroform-methyl alcohol and chloroform-methyl alcohol-water giving 1.6 g of the desired product as a white powder following stirring with ether, filtering and drying.

EXAMPLE 68

Octadecyl 3-hydroxy-2-methylphenyl carbamate

To a suspension of 7.7 g of hexane washed sodium hydride in 100 ml of tetrahydrofuran was added dropwise over 10 minutes a solution of 20 g of 2-methylresorcinol in 100 ml of tetrahydrofuran. After stirring for 1 hour, a solution of 56 ml of octadecylisocyanate in 50 ml of tetrahydrofuran was rapidly added dropwise followed by stirring for 15 hours at room temperature. The mixture was poured into saturated ammonium chloride and extracted with ether. The organic layer was dried with sodium sulfate and evaporated to a waxy solid which was purified by chromatography on silica gel using ethyl acetate-hexanes, and giving 17.5 g of the desired product as a waxy solid.

EXAMPLE 69

3-[[3-[[Hydroxy[2-methyl-3-[[(octadecylamino)carbonyl] oxy]phenoxy]phosphinyl]oxy]phenyl]methyl]-thiazolium, hydroxide, inner salt To a solution of 5 g of octadecyl 3-hydroxy-2-methylphenyl carbamate in 100 ml of carbon tetrachloride was added 2.5 ml of triethylamine followed by a solution of 4.5 g of 3-(bromomethyl)phenyl phosphodichlorodate in 20 ml of carbon tetrachloride. After stirring at ambient temperature for 15 hours, the mixture was filtered through diatomaceous earth and evaporated. The residue was stirred with 30 ml of tetahydrofuran and 15 ml of 0.5N sodium acetate for 1 hour then acidified with 5% hyrochloric acid and extracted with ethyl acetate. The organic layer was dried with sodium sulfate and evaporated. The residue was dissolved in 20 ml of toluene and 1.4 ml of thiazole added followed by heating at 90° C. for 5 hours. The volatiles were removed in vacuo and 50 ml of methyl alcohol added to the residue followed by stirring with 2 g of Amberlite ® A-21 resin for 2 hours. The mixture was filtered and the solvent removed in vacuo. The residue was purified by chromatography on silica gel using chloroform-methyl alcohol-water. The desired compound was obtained as a waxy solid.

EXAMPLE 70

3-[[3-[[Hydroxy[2-methyl-3-[[(octadecylamino)carbonyl] oxy]phenoxy]phosphinyl]oxy]phenyl]methyl]-5-methylthiazolium, hydroxide, inner salt To a solution of 1.26 g of octadecyl 3-hydroxy-2-methylphenyl carbamate in 100 ml of carbon tetrachloride was added 2.5 ml of triethylamine followed by a solution of 1.13 g of 3-(bromomethyl)phenyl phosphodichlorodate in 20 ml of carbon tetrachloride. After stirring at ambient temperature for 15 hours, the mixture was filtered through diatomaceous earth and evaporated. The residue was stirred with 30 ml of tetahydrofuran and 15 ml of 0.5N sodium acetate for 1 hour then acidified with 5% hyrochloric acid and extracted with ethyl acetate. The organic layer was dried with sodium sulfate and evaporated. The residue was dissolved in 20 ml of toluene and 1.4 ml of 5-methylthiazole followed by heating at 90° C. for 5 hours. The volatiles were removed in vacuo and 50 ml of methyl alcohol added to the residue followed by stirring with 2 g of Amberlite ® A-21 resin for 2 hours. The mixture was filtered and the solvent removed in vacuo. The residue was purified by chromatography on silica gel using chloroform-methyl alcohol-water. The desired product weighing 555 mg was obtained as a waxy solid.

EXAMPLE 71

2,5-Dichloro-4-(tetradecyloxy)phenol

To a suspension of 14.86 g of hexanes washed sodium hydride in 100 ml of N,N-dimethylformamide containing 4.19 g of sodium iodide and cooled to 0° C. was added a solution of 50 g of 2,5-dichloro-4-hydroxyphenol in 200 ml of N,N-dimethylformamide over 1 hour. A solution of 1-bromododecane in 100 ml of N,N-dimethylformamide was added over 10 minutes. The bath was removed and the mixture stirred at ambient temperature for 18 hours. The mixture was poured into dilute hydrochloric acid and extracted with ether then filtered. The ether layer was separated, washed with brine and dried over magnesium sulfate. The ether was removed by evaporation and the concentrate distilled using a Kugelrohr apparatus. The fraction boiling at 130°-180° C./0.1 mm was collected and chromatographed on silica gel with hexanes-ether giving 15.2 g of the desired compound as a white solid following hexanes crystallization.

EXAMPLE 72

3-(Bromomethyl)phenyl 2,5-dichloro-4-(tetradecyloxy)-phenyl phosphate

To a solution of 8.0 g of 2,5-dichloro-4-(tetradecyloxy)phenol in 50 ml of dry carbon tetrachloride was added a solution of 4.86 g of 3-(bromomethyl)phenyl phosphodichlorodate in 10 ml of carbon tetrachloride in an inert atmosphere. A solution of 1.86 ml of triethylamine in 10 ml of carbon tetrachloride was rapidly added followed by and stirring for 4 hours. The mixture was filtered through diatomaceous earth and evaporated to a residue which was stirred for 3 hours with 200 ml of tetrahydrofuran and 200 ml of 0.5M sodium acetate. The tetrahydrofuran was removed under vacuum and the aqueous layer extracted with ether. The organic layer was washed with saturated sodium chloride, dried with magnesium sulfate and evaporated to give 9.0 g of the desired compound as an off white solid.

EXAMPLE 73

3-[[3-[[[2,5-Dichloro-4-(tetradecyloxy)phenoxy]hydroxyphosphinyl]oxy]phenyl]methyl]-5-methylthiazolium, hydroxide, inner salt To a solution of 4.5 g of 3-(bromomethyl)phenyl-2,5-dichloro-4-(tetradecyloxy)phenyl phosphate in 40 ml of dry toluene was added 3.58 g of 5-methyl thiazole followed by stirring, in an inert atmosphere, at 85° C. for 5 hours. The solvent was removed in vacuo and the residue stirred with 20 g of Amberlite ® IR-4B resin in 200 ml of methyl alcohol for 10 minutes. The mixture was filtered and the solvent removed in vacuo. The residue was columned on silica gel with methyl alcohol-chloroform and methyl alcohol-chloroform-water. Triturated with ether and refrigerated giving 2.2 g of the desired compound as a white amorphous powder.

EXAMPLE 74

3-[[2-[[[2,5-Bis(1,1-dimethylethyl)-4-(dodecyloxy)-phenoxy]hydroxyphosphinyl]oxy]phenyl]methyl]-2-methylthiazolium, hydroxide, inner salt A suspension of 5 g of 2,5-bis(1,1-dimethylethyl)-4-dodecyloxyphenol, 2.59 g of 2-chloro-4H-1,3,2-benzodioxaphosphorin, 2-oxide and 1.55 g of triethylamine in 60 ml of carbon tetrachloride was stirred at room temperature for 5 hours followed by storing in a freezer for 2 days. The mixture was diluted with ether and filtered. The solvent was removed from the filtrate and the residue dissolved in 75 ml of acetonitrile containing 6.35 g of 5-methylthiazole and 191.8 mg of sodium iodide. The mixture was heated at 85° C. for 19 hours. The solvent was removed in vacuo and the residue stirred with 200 ml of methyl alcohol and 20 g of Amberlite ® IR-45 resin for 1.5 hours. The mixture was filtered and the solvent removed in vacuo. The residue was columned on silica gel with chloroform-methyl alcohol and chloroform-methyl alcohol-water. Dissolved in ether and cooled giving 1.8 g of the desired compound as a white amorphous powder.

EXAMPLE 75

Octadecyl 2,5-bis (1,1-dimethylethyl)-4-hydroxyphenyl carbamate

To a suspension of 2.16 g of hexanes washed sodium hydride in 50 ml of dry tetrahydrofuran was added a solution of 10 g of di-t-butylhydroquinone in 100 ml of tetrahydrofuran dropwise over 20 minutes. After stirring for 1 hour, a solution of 13.3 g of octadecylisocyanate in 50 ml of tetrahydrofuran was added dropwise over 20 minutes followed by stirring for 24 hours. The mixture was poured into saturated ammonium chloride and extracted with ether several times. The combined extracts were dried with magnesium sulfate and evaporated to a syrup which was columned on silica gel with hexanes and ethyl acetate-hexanes to give 2.93 g of the desired compound as a heavy yellow oil.

EXAMPLE 76

3-[[3-[[[2,5-Bis(1,1-dimethylethyl)-4-[[(octadecylamino) carbonyl]oxy]phenoxy]hydroxyphosphinyl]oxy]phenyl] methyl]thiazolium, hydroxide, inner salt To a solution of 2.0 g of octadecyl 2,5-bis(1,1-dimethylethyl)-4-hydroxyphenyl carbamate in 10 ml of carbon tetrachloride was added 0.84 ml of triethylamine followed by the slow addition of 1.76 g of 3-(bromomethyl)phenyl phosphodichlorodate dissolved in 5 ml of carbon tetrachloride. The reaction was stirred at room temperature for 1 hour. An additional 1 g of 3-(bromomethyl)phenyl phosphodichlorodate was added followed by 1 ml of triethylamine and continued stirring for 48 hours. The mixture was refluxed for 1.5 hours. The solvent was evaporated and the residue stirred for 45 minutes with 25 ml of tetrahyrofuran and 25 ml of 0.5N sodium acetate. The mixture was acidified and extracted with ethyl acetate. The organic layer was dried with sodium acetate and evaporated. The residue was dissolved in 15 ml of toluene and 0.35 ml of thiazole added followed by heating at 90° C. for 15 hours. The solvent was removed in vacuo and the residue stirred with 30 ml of methyl alcohol and 2 g of Amberlite ® A-21 resin for 1 hour. The mixture was filtered and the solvent removed in vacuo. The residue was columned on silica gel using chloroform-methyl alcohol-water giving 800 mg of the desired compound as a white solid.

According to the methods described in detail hereinabove in Examples 1–76, the compounds of this invention listed hereinbelow in Table II can be prepared using the appropriate, hydroxy compound, phosphorous reagent, and nitrogen containing heterocycle. The hydroxy compounds needed to prepare these compounds are either articles of commerce or can be obtained using the procedure described hereinabove in Flowsheets E and F, and U.S. Pat. Nos. 4,697,031; 4,699,990 and 4,640,913, and in our copending patent application 177,299.

The phosphorous reagents are prepared as described hereinabove in Flowsheet C and D and in the patents and copending applications described hereinabove. These methods are applicable to the preparation of the compounds of this invention by one skilled in the art.

TABLE II

3-[3-[[[3-(Hexadecyloxy)phenoxy]hydroxyphosphinyl]oxy]phenyl] methyl]-5-methylthiazolium, hydroxide, inner salt
3-[3-[[[3-(Hexadecyloxy)-2-methylphenoxy]hydroxyphosphinyl]oxy]phenyl] methyl]thiazolium, hydroxide, inner salt
3-[3-[[[3-(Hexadecyloxy)-2-methylphenoxy]hydroxyphosphinyl]oxy)phenyl] methyl]-4-methylthiazolium, hydroxide, inner salt
3-[3-[[[3-(Hexadecyloxy)-2-methoxyphenoxy]hydroxyphosphinyl]oxy]phenyl] methyl]thiazolium, hydroxide, inner salt
3-[3-[[[3-(Hexadecyloxy)-2-methoxyphenoxy]hydroxyphosphinyl]oxy]phenyl]

TABLE II-continued methyl]-5-methylthiazolium, hydroxide, inner salt
3-[3-[[[3-(Hexadecyloxy)-2-nitrophenoxy]hydroxyphosphinyl]oxy]phenyl]
methyl]thiazolium, hydroxide, inner salt
3-[3-[[[3-(Hexadecyloxy)-2-nitrophenoxy]hydroxyphosphinyl]oxy]phenyl]
methyl]-5-methylthiazolium, hydroxide, inner salt
3-[3-[[[3-(Hexadecyloxy)-2-carbomethoxyphenoxy]hydroxyphosphinyl]oxy]phenyl]
methyl]thiazolium, hydroxide, inner salt
3-[3-[[[3-(Hexadecyloxy)-2-carbomethoxyphenoxy]hydroxyphosphinyl]oxy]phenyl]
methyl]-5-methylthiazolium, hydroxide, inner salt
3-[3-[[[3-(Hexadecyloxy)-5-methylphenoxy]hydroxyphosphinyl]oxy]phenyl]
methyl]thiazolium, hydroxide, inner salt
3-[3-[[[3-(Hexadecyloxy)-5-methylphenoxy]hydroxyphosphinyl]oxy]phenyl]
methyl]-5-methylthiazolium, hydroxide, inner salt
3-[3-[[[3-(Hexadecyloxy)-5-methoxyphenoxy]hydroxyphosphinyl]oxy]phenyl]
methyl)thiazolium, hydroxide, inner salt
3-[3-[[[3-(Hexadecyloxy)-5-methoxyphenoxy]hydroxyphosphinyl]oxy]phenyl]
methyl]-5-methylthiazolium, hydroxide, inner salt
3-[3-[[[3-(Tetradecyloxy)phenoxy]hydroxyphosphinyl]oxy]phenyl]
methyl]thiazolium, hydroxide, inner salt
3-[3-[[[3-(Tetradecyloxy)phenoxy]hydroxyphosphinyl]oxy]phenyl]
methyl]-5-methylthiazolium, hydroxide, inner salt
3-[3-[[[3-(Tetradecyloxy)phenoxy]hydroxyphosphinyl]oxy]phenyl]
methyl]-4-methylthiazolium, hydroxide, inner salt
3-[3-[[[3-(Tetradecyloxy)-2-methylphenoxy]hydroxyphosphinyl]oxy]phenyl]
methyl]thiazolium, hydroxide, inner salt
3-[3-[[[3-(Tetradecyloxy)-2-methylphenoxy]hydroxyphosphinyl]oxy]phenyl]
methyl]-5-methylthiazolium, hydroxide, inner salt
3-[3-[[[3-(Tetradecyloxy)-2-methylphenoxy]hydroxyphosphinyl]oxy]phenyl]
methyl]-4-methylthiazolium, hydroxide, inner salt
3-[3-[[[3-(Tetradecyloxy)-2-methoxyphenoxy]hydroxyphosphinyl]oxy]phenyl]
methyl]thiazolium, hydroxide, inner salt
3-[3-[[[3-(Tetradecyloxy)-2-methoxyphenoxy]hydroxyphosphinyl]oxy]phenyl]
methyl]-5-methylthiazolium, hydroxide, inner salt
3-[3-[[[3-(Tetradecyloxy)-2-methoxyphenoxyhydroxyphosphinyl]oxy]phenyl)
methyl]-4-methylthiazolium, hydroxide, inner salt
3-[3-[[[3-(Tetradecyloxy)-2-nitrophenoxy]hydroxyphosphinyl]oxy]phenyl]
methyl]thiazolium, hydroxide, inner salt
3-[3-[[[3-(Tetradecyloxy)-2-nitrophenoxy]hydroxyphosphinyl]oxy]phenyl]
methyl]-5-methylthiazolium, hydroxide, inner salt
3-[3-[[[3-(Tetradecyloxy)-2-nitrophenoxy]hydroxyphosphinyl]oxy]phenyl]
methyl]-4-methylthiazolium, hydroxide, inner salt
3-[3-[[[3-(Tetradecyloxy)-2-carbomethoxyphenoxy]hydroxyphosphinyl]oxy]phenyl]
methyl]thiazolium, hydroxide, inner salt
3-[3-[[[3-(Tetradecyloxy)-2-carbomethoxyphenoxy)hydroxyphosphinyl]oxy]phenyl]
methyl]-5-methylthiazolium, hydroxide, inner salt
3-[3-[[[3-(Tetradecyloxy)-2-carbomethoxyphenoxy]hydroxyphosphinyl]oxy]phenyl]
methyl]-4-methylthiazolium, hydroxide, inner salt
3-[3-[[[3-(Tetradecyloxy)-5-methylphenoxy]9 hydroxyphosphinyl]oxy]phenyl]
methyl]thiazolium, hydroxide, inner salt
3-[3-[[[3-(Tetradecyloxy)-5-methylphenoxy]hydroxyphosphinyl]oxy]phenyl]
methyl]-5-methylthiazolium, hydroxide, inner salt
3-[3-[[[3-(Tetradecyloxy)-5-methylphenoxy]hydroxyphosphinyl]oxy]phenyl]
methyl]-4-methylthiazolium, hydroxide, inner salt
3-[3-[[[3-(Tetradecyloxy)-5-methoxyphenoy]hydroxyphosphinyl]oxy]phenyl]
methyl]thiazolium, hydroxide, inner salt
3-[3-[[[3-(Tetradecyloxy)-5-methoxyphenoxy]hydroxyphosphinyl]oxy]phenyl]
methyl]-5-methylthiazolium, hydroxide, inner salt
3-[3-[[[3-(Dodecyloxy)phenoxy]hydroxyphosphinyl]oxy]phenyl]
methyl]thiazolium, hydroxide, inner salt
3-[3-[[[3-(Dodecyloxy)phenoxy]hydroxyphosphinyl]oxy]phenyl]
methyl]-4-methylthiazolium, hydroxide, inner salt
3-[3-[[[3-(Dodecyloxy)-2-methylphenoxy]hydroxyphosphinyl]oxy]phenyl]
methyl]thiazolium, hydroxide, inner salt
3-[3-[[[3-(Dodecyloxy)-2-methylphenoxy]hydroxyphosphinyl]oxy]phenyl]
methyl]-4-methylthiazolium, hydroxide, inner salt
3-[3-[[[3-(Dodecyloxy)-2-methoxyphenoxy]hydroxyphosphinyl]oxy]phenyl]
methyl]thiazolium, hydroxide, inner salt
3-[3-[[[3-(Dodecyloxy)-2-methoxyphenoxy]hydroxyphosphinyl]oxy]phenyl]
methyl]-4-methylthiazolium, hydroxide, inner salt
3-[3-[[[3-(Dodecyloxy)-2-nitrophenoxy]hydroxyphosphinyl]oxy]phenyl]
methyl]thiazolium, hydroxide, inner salt
3-[3-[[[3-(Dodecyloxy)-2-nitrophenoxy]hydroxyphosphinyl]oxy]phenyl]
methyl]-4-methylthiazolium, hydroxide, inner salt
3-[3-[[[3-(Dodecyloxy)-2-carbomethoxyphenoxy]hydroxyphosphinyl]oxy]phenyl]
methyl]thiazolium, hydroxide, inner salt
3-[3-[[[3-(Dodecyloxy)-2-carbomethoxyphenoxy]hydroxyphosphinyl]oxy]phenyl]
methyl]-4-methylthiazolium, hydroxide, inner salt
3-[3-[[[3-(Dodecyloxy)-5-methylphenoxy]hydroxyphosphinyl]oxy]phenyl]
methyl]thiazolium, hydroxide, inner salt
3-[3-[[[3-(Dodecyloxy)-5-methylphenoxy]hydroxyphosphinyl]oxy]phenyl]
methyl]-4-methylthiazolium, hydroxide, inner salt
3-[3-[[[3-(Dodecyloxy)-5-methoxyphenoxy]hydroxyphosphinyl]oxy]phenyl]

TABLE II-continued methyl]thiazolium, hydroxide, inner salt
3-[3-[[[3-(Dodecyloxy)-5-methoxyphenoxy]hydroxyphosphinyl]oxy]phenyl]
methyl]-4-methylthiazolium, hydroxide, inner salt
3-[3-[[[2-(Hexadecyloxy)phenoxy]hydroxyphosphinyl]oxy]phenyl]
methyl]thiazolium, hydroxide, inner salt
3-[3-[[[2-(Hexadecyloxy)phenoxy]hydroxyphosphinyl]oxy]phenyl]
methyl]-5-methylthiazolium, hydroxide, inner salt
3-[3-[[[2-(Hexadecyloxy)-5-methylphenoxy]hydroxyphosphinyl]oxy]phenyl]
methyl]thiazolium, hydroxide, inner salt
3-[3-[[[2-(Hexadecyloxy)-5-methylphenoxy]hydroxyphosphinyl]oxy]phenyl]
methyl]-5-methylthiazolium, hydroxide, inner salt
3-[3-[[[2-(Hexadecyloxy)-5-methoxyphenoxy]hydroxyphosphinyl]oxy]phenyl]
methyl]thiazolium, hydroxide, inner salt
3-[3-[[[2-(Hexadecyloxy)-5-methoxyphenoxy]hydroxyphosphinyl]oxy]phenyl]
methyl]-5-methylthiazolium, hydroxide, inner salt
3-[3-[[[2-(Hexadecyloxy)-3-chlorophenoxy]hydroxyphosphinyl]oxy]phenyl]
methyl]thiazolium, hydroxide, inner salt
3-[3-[[[2-(Tetradecyloxy)phenoxy]hydroxyphosphinyl]oxy]phenyl]
methyl]thiazolium, hydroxide, inner salt
3-[3-[[[2-(Tetradecyloxy)phenoxy]hydroxyphosphinyl]oxy]phenyl]
methyl]-5-methylthiazolium, hydroxide, inner salt
3-[3-[[[2-(Tetradecyloxy)phenoxy]hydroxyphosphinyl]oxy]phenyl]
methyl]-4-methylthiazolium, hydroxide, inner salt
3-[3-[[[2-(Tetradecyloxy)-5-methylphenoxy]hydroxyphosphinyl]oxy]phenyl]
methyl]thiazolium, hydroxide, inner salt
3-[3-[[[2-(Tetradecyloxy)-5-methylphenoxy]hydroxyphosphinyl]oxy]phenyl]
methyl]-5-methylthiazolium, hydroxide, inner salt
3-[3-[[[2-(Tetradecyloxy)-5-methylphenoxy]hydroxyphosphinyl]oxy]phenyl]
methyl]-4-methylthiazolium, hydroxide, inner salt
3-[3-[[[2-(Tetradecyloxy)-5-methoxyphenoxy]hydroxyphosphinyl]oxy]phenyl]
methyl]thiazolium, hydroxide, inner salt
3-[3-[[[2-(Tetradecyloxy)-5-methoxyphenoxy]hydroxyphosphinyl]oxy]phenyl]
methyl]-5-methylthiazolium, hydroxide, inner salt
3-[3-[[[2-(Tetradecyloxy)-5-methoxyphenoxy]hydroxyphosphinyl]oxy]phenyl]
methyl]-4-methylthiazolium, hydroxide, inner salt
3-[3-[[[2-(Tetradecyloxy)-3-chlorophenoxy]hydroxyphosphinyl]oxy]phenyl]
methyl]thiazolium, hydroxide, inner salt
3-[3-[[[2-(Tetradecyloxy)-3-chlorophenoxy]hydroxyphosphinyl]oxy]phenyl]
methyl]-5-methylthiazolium, hydroxide, inner salt
3-[3-([[2-(Tetradecyloxy)-3-chlorophenoxy)hydroxyphosphinyl]oxy]phenyl]
methyl]-4-methylthiazolium, hydroxide, inner salt
3-[3-[[[2-(Dodecyloxy)phenoxy)hydroxyphosphinyl]oxy]phenyl]
methyl]thiazolium, hydroxide, inner salt
3-[3-[[[2-(Dodecyloxy)phenoxy]hydroxyphosphinyl]oxy]phenyl]
methyl]-4-methylthiazolium, hydroxide, inner salt
3-[3-[[[2-(Dodecyloxy)-5-methylphenoxy]hydroxyphosphinyl]oxy]phenyl]
methyl]thiazolium, hydroxide, inner salt
3-[3-[[[2-(Dodecyloxy)-5-methylphenoxy]hydroxyphosphinyl]oxy]phenyl]
methyl]-4-methylthiazolium, hydroxide, inner salt
3-[3-[[[2-(Dodecyloxy)-5-methoxyphenoxy]hydroxyphosphinyl]oxy]phenyl]
methyl]thiazolium, hydroxide, inner salt
3-[3-[[[2-(Dodecyloxy)-5-methoxyphenoxy]hydroxyphosphinyl]oxy]phenyl]
methyl]-4-methylthiazolium, hydroxide, inner salt
3-[3-[[[2-(Dodecyloxy)-3-chlorophenoxy]hydroxyphosphinyl]oxy]phenyl]
methyl]thiazolium, hydroxide, inner salt
3-[3-[[[2-(Dodecyloxy)-3-chlorophenoxy]hydroxyphosphinyl]oxy]phenyl]
methyl]-4-methylthiazolium, hydroxide, inner salt
3-[3-[[[4-(Hexadecyloxy)phenoxy]hydroxyphosphinyl]oxy]phenyl]
methyl]thiazolium, hydroxide, inner salt
3-[3-[[[4-(Hexadecyloxy)phenoxy]hydroxyphosphinyl]oxy]phenyl]
methyl]-5-methylthiazolium, hydroxide, inner salt
3-[3-[[[4-(Hexadecyloxy)-2-methylphenoxy]hydroxyphosphinyl]oxy]phenyl]
methyl]thiazolium, hydroxide, inner salt
3-[3-[[[4-(Hexadecyloxy)-2-methylphenoxhydroxyphosphinyl]oxy]phenyl]
methyl]-5-methylthiazolium, hydroxide, inner salt
3-[3-[[[4-(Hexadecyloxy)-2-methoxyphenoxy]hydroxyphosphinyl]oxy]phenyl]
methyl]thiazolium, hydroxide, inner salt
3-[3-[[[4-(Hexadecyloxy)-2-methoxyphenoxy]hydroxyphosphinyl]oxy]phenyl]
methyl]-5-methylthiazolium, hydroxide, inner salt
3-[3-[[[4-(Hexadecyloxy)-2-nitrophenoxhydroxyphoaphinyl]oxy]phenyl]
methyl]-5-methylthiazolium, hydroxide, inner salt
3-[3-[[[4-(Hexadecyloxy)-2-carbomethoxyphenoxy]hydroxyphosphinyl]oxy]phenyl]
methyl]thiazolium, hydroxide, inner salt
3-[3-[[[4-(Hexadecyloxy)-2,5-di-t-butylphenoxy]hydroxyphosphinyl]
methyl]thiazolium, hydroxide, inner salt
3-[3-[[[4-(Hexadecyloxy)-2,5-di-t-butylphenoxy]hydroxyphosphinyl]
methyl]-5-methylthiazolium, hydroxide, inner salt
3-[3-[[[4-(Hexadecyloxy)-2,5-dichlorophenoxy]hydroxyphosphinyl]oxy]
methyl]thiazolium, hydroxide, inner salt
3-[3-[[[4-(Hexadecyloxy)-2,5-dichlorophenoxy]hydroxyphosphinyl]oxy]
methyl]-5-methylthiazolium, hydroxide, inner salt
3-[3-[[[4-(Hexadecyloxy)-2-chlorophenoxy]hydroxyphosphinyl]oxy]phenyl]

TABLE II-continued methyl]thiazolium, hydroxide, inner salt
3-[3-[[[4-(Hexadecyloxy)-2-chlorophenoxy]hydroxyphosphinyl]oxy]phenyl]
methyl]-5-methylthiazolium, hydroxide, inner salt
3-[3-[[[4-(Hexadecyloxy)-3-chlorophenoxy]hydroxyphosphinyl]oxy]phenyl]
methyl]-5-methylthiazolium, hydroxide, inner salt
3-[3-[[[4-(Tetradecyloxy)phenoxy]hydroxyphosphinyl]oxy]phenyl]
methyl]thiazolium, hydroxide, inner salt
3-[3-[[[4-(Tetradecyloxy)phenoxy]hydroxyphosphinyl]oxy]phenyl]
methyl]-5-methylthiazolium, hydroxide, inner salt
3-[3-[[[4-(Tetradecyloxy)-2-methylphenoxy]hydroxyphosphinyl]oxy]phenyl]
methyl]-5-methylthiazolium, hydroxide, inner salt
3-[3-[[[4-(Tetradecyloxy)-2-methylphenoxy]hydroxyphosphinyl]oxy]phenyl]
methyl]-4-methylthiazolium, hydroxide, inner salt
3-[3-[[[4-(Tetradecyloxy)-2-methoxyphenoxy]hydroxyphosphinyl]oxy]phenyl]
methyl]thiazolium, hydroxide, inner salt
3-[3-[[[4-(Tetradecyloxy)-2-methoxyphenoxy]hydroxyphosphinyl]oxy]phenyl]
methyl]-4-methylthiazolium, hydroxide, inner salt
3-[3-[[[4-(Tetradecyloxy)-2-nitrophenoxy]hydroxyphosphinyl]oxy]phenyl]
methyl]thiazolium, hydroxide, inner salt
3-[3-[[[4-(Tetradecyloxy)-2-nitrophenoxy]hydroxyphosphinyl]oxy]phenyl]
methyl]-5-methylthiazolium, hydroxide, inner salt
3-[3-[[[4-(Tetradecyloxy)-2-nitrophenoxy]hydroxyphosphinyl]oxy]phenyl]
methyl]-4-methylthiazolium, hydroxide, inner salt
3-[3-[[[4-(Tetradecyloxy)-2-carbomethoxyphenoxy]hydroxyphosphinyl]oxy]phenyl]
methyl]thiazolium, hydroxide, inner salt
3-[3-[[[4-(Tetradecyloxy)-2-carbomethoxyphenoxy]hydroxyphosphinyl]oxy]phenyl]
methyl]-5-methylthiazolium, hydroxide, inner salt
3-[3-[[[4-(Tetradecyloxy)-2-carbomethoxyphenoxy]9 hydroxyphosphinyl]oxy]phenyl]
methyl]-4-methylthiazolium, hydroxide, inner salt
3-[3-[[[4-(Tetradecyloxy)-2,5-di-t-butylphenoxy]hydroxyphosphinyl]oxy]phenyl]
methyl]-4-methylthiazoliu, hydroide, inner salt
3-[3-[[[4-(Tetradecyloxy)-2,5-dichlorophenoy]hydroxyphosphinyl]oxy]phenyl]
methyl]thiazolium, hydroxide, inner salt
3-[3-[[[4-(Tetradecyloxy)-2,5-dichlorophenoxy]hydroxyphosphinyl]oxy]phenyl]
methyl]-5-methylthiazolium, hydroxide, inner salt
3-[3-[[[4-(Tetradecyloxy)-2,5-dichlorophenoxhydroxyphosphinyl]oxy]phenyl]
methyl]-4-methylthiazolium, hydroxide, inner salt
3-[3-[[[4-(Tetradecyloxy)-2-chlorophenoxy]hydroxyphosphinyl]oxy]phenyl]
methyl]thiazolium, hydroxide, inner salt
3-[3-[[[4-(Tetradecyloxy)-2-chlorophenoxy]hydroxyphosphinyl]oxy]phenyl]
methyl]-5-methylthiazolium, hydroxide, inner salt
3-[3-[[[4-(Tetradecyloxy)-2-chlorophenoxy]hydroxyI:hosphinyl]oxy]phenyl]
methyl]-4-methylthiazolium, hydroxide, inner salt
3-[3-[[[4-(Tetradecyloxy)-3-chlorophenoxy]hydroxyphosphinyl]oxy]phenyl]
methyl]thiazolium, hydroxide, inner salt
3-[3-[[[4-(Tetradecyloxy)-3-chlorophenoxy]hydroxyphosphinyl]oxy]phenyl]
methyl]-4-methylthiazolium, hydroxide, inner salt
3-[3-[[[4-(Dodecyloxy)phenoxy]hydroxyphosphinyl]oxy]phenyl]
methyl]thiazolium, hydroxide, inner salt
3-[3-[[[4-(Dodecyloxy)phenoxy]hydroxyphosphinyl]oxy]phenyl]
methyl]-4-methylthiazolium, hydroxide, inner salt
3-[3-[[[4-(Dodecyloxy)-2-methylphenoxylhydroxyphosphinyl]oxy]phenyl]
methyl]thiazolium, hydroxide, inner salt
3-[3-[[[4-(Dodecyloxy)-2-methylphenoxy]hydroxyphosphinyl]oxy]phenyl]
methyl]-4-methylthiazolium, hydroxide, inner salt
3-[3-[[[4-(Dodecyloxy)-2-methoxyphenoxy]hydroxyphosphinyl]oxy]phenyl]
methyl]thiazolium, hydroxide, inner salt
3-[3-[[[4-(Dodecyloxy)-2-methoxyphenoxy]hydroxyphosphinyl]oxy]phenyl]
methyl]-4-methylthiazolium, hydroxide, inner salt
3-[3-[[[4-(Dodecyloxy)-2-nitrophenoxy]hydroxyphosphinyl]oxy]phenyl]
methyl]thiazolium, hydroxide, inner salt
3-[3-[[[4-(Dodecyloxy)-2-nitrophenoxy]hydroxyphosphinyl]oxy]phenyl]
methyl]-4-methylthiazolium, hydroxide, inner salt
3-[3-[[[4-(Dodecyloxy)-2-carbomethoxyphenoxy]hydroxyphosphinyl]oxy]phenyl]
methyl]-4-methylthiazolium, hydroxide, inner salt
3-[3-[[[4-(Dodecyloxy)-2,5-di-t-butylphenoxy]hydroxyphosphinyl]oxy]phenyl]
methyl]thiazolium, hydroxide, inner salt
3-[3-[[[4-(Dodecyloxy)-2,5-di-t-butylphenoxy]hydroxyphosphinyl]oxy]phenyl]
methyl]-4-methylthiazolium, hydroxide, inner salt
3-[3-[[[4-(Dodecyloxy)-2,5-dichlorophenoxy]hydroxyphosphinyl]oxy]phenyl]
methyl]-4-methylthiazolium, hydroxide, inner salt
3-[3-[[[4-(Dodecyloxy)-2-chlorophenoxy]hydroxyphosphinyl]oxy]phenyl]
methyl]thiazolium, hydroxide, inner salt
3-[3-[[[4-(Dodecyloxy)-2-chlorophenoxy]hydroxyphosphinyl]oxy]phenyl]
methyl]-4-methylthiazolium, hydroxide, inner salt
3-[3-[[[4-(Dodecyloxy)-3-chlorophenoxy]hydroxyphosphinyl]oxy]phenyl]
methyl]thiazolium, hydroxide, inner salt
3-[3-[[[4-(Dodecyloxy)-3-chlorophenoxy]hydroxyphosphinyl]oxy]phenyl]
methyl]-4-methylthiazolium, hydroxide, inner salt
3-[2-[[[3-(Hexadecyloxy)phenoxy]hydroxyphosphinyl]oxy]phenyl]
methyl]thiazolium, hydroxide, inner salt
3-[2-[[[3-(Hexadecyloxy)phenoxy]hydroxyphosphinyl]oxy]phenyl]

TABLE II-continued methyl]-5-methylthiazolium, hydroxide, inner salt
3-[2-[[[3-(Hexadecyloxy)-2-methylphenoxy]hydroxyphosphinyl]oxy]phenyl]
methyl]thiazolium, hydroxide, inner salt
3-[2-[[[3-(Hexadecyloxy)-2-methylphenoxy]hydroxyphosphinyl]oxy]phenyl]
methyl]-5-methylthiazolium, hydroxide, inner salt
3-[2-[[[3-(Hexadecyloxy)-2-methoxyphenoxy]hydroxyphosphinyl]oxy]phenyl]
methyl]thiazolium, hydroxide, inner salt
3-[2-[[[3-(Hexadecyloxy)-2-nitrophenoxy]hydroxyphosphinyl]oxy]phenyl]
methyl]thiazolium, hydroxide, inner salt
3-[2-[[[3-(Hexadecyloxy)-2-nitrophenoxy]hydroxyphosphinyl]oxy]phenyl]
methyl]-5-methylthiazolium, hydroxide, inner salt
3-[2-[[[3-(Hexadecyloxy)-2-carbomethoxyphenoxy]hydroxyphosphinyl]oxy]phenyl]
methyl]thiazolium, hydroxide, inner salt
3-[2-[[[3-(Hexadecyloxy)-2-carbomethoxyphenoxy]hydroxyphosphinyl]oxy]phenyl]
methyl]-5-methylthiazolium, hydroxide, inner salt
3-[2-[[[3-(Hexadecyloxy)-5-methylphenoxy]hydroxyphosphinyl]oxy]phenyl]
methyl]thiazolium, hydroxide, inner salt
3-[2-[[[3-(Hexadecyloxy)-5-methylphenoxy]hydroxyphosphinyl]oxy]phenyl]
methyl]-5-methylthiazolium, hydroxide, inner salt
3-[2-[[[3-(Hexadecyloxy)-5-methoxyphenoxy]hydroxyphosphinyl]oxy]phenyl]
methyl]thiazolium, hydroxide, inner salt
3-[2-[[[3-(Hexadecyloxy)-5-methoxyphenoxy]hydroxyphosphinyl]oxy]phenyl]
methyl]-5-methylthiazolium, hydroxide, inner salt
3-[2-[[[3-(Tetradecyloxy)phenoxy]hydroxyphosphinyl]oxy]phenyl]
methyl]thiazolium, hydroxide, inner salt
3-[2-[[[3-(Tetradecyloxy)phenoxy]hydroxyphosphinyl]oxy]phenyl]
methyl]-4-methylthiazolium, hydroxide, inner salt
3-[2-[[[3-(Tetradecyloxy)-2-methylphenoxhydroxyphosphinyl]oxy]phenyl]
methyl]thiazolium, hydroxide, inner salt
3-[2-[[[3-(Tetradecyloxy)-2-methylphenoxy]hydroxyphosphinyl]oxy]phenyl]
methyl]-5-methylthiazolium, hydroxide, inner salt
3-[2-[[[3-(Tetradecyloxy)-2-methylphenoxy]hydroxyphosphinyl]oxy]phenyl]
methyl]-4-methylthiazolium, hydroxide, inner salt
3-[2-[[[3-(Tetradecyloxy)-2-methoxyphenoxy]hydroxyphosphinyl]oxy]phenyl]
methyl]thiazolium, hydroxide, inner salt
3-[2-[[[3-(Tetradecyloxy)-2-methoxyphenoxy]hydroxyphosphinyl]oxy]phenyl]
methyl]-5-methylthiazolium, hydroxide, inner salt
3-[2-[[[3-(Tetradecyloxy)-2-methoxyphenoxy]hydroxyphosphinyl]oxy]phenyl]
methyl]-4-methylthiazolium, hydroxide, inner salt
3-[2-[[[3-(Tetradecyloxy)-2-nitrophenoxy]hydroxyphosphinyl]oxy]phenyl]
methyl]thiazolium, hydroxide, inner salt
3-[2-[[[3-(Tetradecyloxy)-2-nitrophenoxy]hydroxyphosphinyl]oxy]phenyl]
methyl]-4-methylthiazolium, hydroxide, inner salt
3-[2-[[[3-(Tetradecyloxy)-2-carbomethoxyphenoxy]hydroxyphosphinyl]oxy]phenyl]
methyl]thiazolium, hydroxide, inner salt
3-[2-[[[3-(Tetradecyloxy)-2-carbomethoxyphenoxy]hydroxyphosphinyl]oxy]phenyl]
methyl]-5-methylthiazolium, hydroxide, inner salt
3-[2-[[[3-(Tetradecyloxy)-2-carbomethoxyphenoxy]hydroxyphosphinyl]oxy]phenyl]
methyl]-4-methylthiazolium, hydroxide, inner salt
3-[2-[[[3-(Tetradecyloxy)-5-methylphenoxy]hydroxyphosphinyl]oxy]phenyl]
methyl]thiazolium, hydroxide, inner salt
3-[2-[[[3-(Tetradecyloxy)-5-methylphenoxy]hydroxyphosphinyl]oxy]phenyl]
methyl]-4-methylthiazolium, hydroxide, inner salt
3-[2-[[[3-(Tetradecyloxy)-5-methoxyphenoxy]hydroxyphosphinyl]oxy]phenyl]
methyl]thiazolium, hydroxide, inner salt
3-[2-[[[3-(Tetradecyloxy)-5-methoxyphenoxy]hydroxyphosphinyl]oxy]phenyl]
methyl]-5-methylthiazolium, hydroxide, inner salt
3-[2-[[[3-(Tetradecyloxy)-5-methoxyphenoxy]hydoxyphosphinyl]oxy]phenyl]
methyl]-4-methylthiazolium, hydroxide, inner salt
3-[2-[[[3-(Dodecyloxy)phenoxy]hydroxyphosphinyl]oxy]9 phenyl]
methyl]thiazolium, hydroxide, inner salt
3-[2-[[[3-(Dodecyloxy)phenoxy]hydroxyphosphinyl]oxy]phenyl]
methyl]-4-methylthiazolium, hydroxide, inner salt
3-[2-[[[3-(Dodecyloxy)-2-methylphenoxy]hydroxyphosphinyl]oxy]phenyl]
methyl]thiazolium, hydroxide, inner salt
3-[2-[[[3-(Dodecyloxy)-2-methylphenoxy]hydroxyphosphinyl]oxy]phenyl]
methy!]-4-methylthiazolium, hydroxide, inner salt
3-[2-[[[3-(Dodecyloxy)-2-methoxyphenoxy]hydroxyphosphinyl]oxy]phenyl]
methyl]thiazolium, hydroxide, inner salt
3-[2-[[[3-(Dodecyloxy)-2-nitrophenoxy]hydroxyphosphinyl]oxy]phenyl]
methyl]thiazolium, hydroxide, inner salt
3-[2-[[[3-(Dodecyloxy)-2-nitrophenoxy]hydroxyphosphinyl]oxy]phenyl]
methyl]-4-methylthiazolium, hydroxide, inner salt
3-[2-[[[3-(Dodecyloxy)-2-carbomethoxyphenoxy]hydroxyphosphinyl]oxy]phenyl]
methyl]thiazolium, hydroxide, inner salt
3-[2-[[[3-(Dodecyloxy)-2-carbomethoxyphenoxy]hydroxyphosphinyl]oxy]phenyl]
methyl]-4-methylthiazolium, hydroxide, inner salt
3-[2-[[[3-(Dodecyloxy)-5-methylphenoxy]hydroxyphosphinyl]oxy]phenyl]
methyl]thiazolium, hydroxide, inner salt
3-[2-[[[3-(Dodecyloxy)-5-methylphenoxy]hydroxyphosphinyl]oxy]phenyl]
methyl]-4-methylthiazolium, hydroxide, inner salt
3-[2-[[[3-(Dodecyloxy)-5-methoxyphenoxylhydroxyphosphinyl]oxy]phenyl]

TABLE II-continued methyl]thiazolium, hydroxide, inner salt
3-[2-[[[(2-(Hexadecyloxy)phenoxy)hydroxyphosphinyl]oxy]phenyl]
methyl]thiazolium, hydroxide, inner salt
3-[2-[[[2-(Hexadecyloxy)phenoxy)hydroxyphosphinyl]oxy]phenyl]
methyl]-5-methylthiazolium, hydroxide, inner salt
3-[2-[[[2-(Hexadecyloxy)-5-methylphenoxy]hydroxyphosphinyl]oxy]phenyl]
methyl]thiazolium, hydroxide, inner salt
3-[2-[[[2-(Hexadecyloxy)-5-methylphenoxy]hydroxyphosphinyl]oxy]phenyl]
methyl]-5-methylthiazolium, hydroxide, inner salt
3-[2-[[[2-(Hexadecyloxy)-5-methoxyphenoxy]hydroxyphosphinyl]oxy]phenyl]
methyl]thiazolium, hydroxide, inner salt
3-[2-[[[2-(Hexadecyloxy)-5-methoxyphenoxy]hydroxyphosphinyl]oxy]phenyl]
methyl]-5-methylthiazolium, hydroxide, inner salt
3-[2-[[[2-(Hexadecyloxy)-3-chlorophenoxy]hydroxyphosphinyl]oxy]phenyl]
methyl]thiazolium, hydroxide, inner salt
3-[2-[[[2-(Hexadecyloxy)-3-chlorophenoxy]hydroxyphosphinyl]oxy]phenyl]
methyl]-5-methylthiazolium, hydroxide, inner salt
3-[2-[[[2-(Tetradecyloxy)phenoxy]hydroxyphosphinyl]oxy]phenyl]
methyl]thiazolium, hydroxide, inner salt
3-[2-[[[2-(Tetradecyloxy)phenoxy]hydroxyphosphinyl]oxy]phenyl]
methyl]-4-methylthiazolium, hydroxide, inner salt
3-[2-[[[2-(Tetradecyloxy)-5-methylphenoxy]hydroxyphosphinyl]oxy]phenyl]
methyl]thiazolium, hydroxide, inner salt
3-[2-[[[2-(Tetradecyloxy)-5-methylphenoxy]hydroxyphosphinyl]oxy]phenyl]
methyl]-5-methylthiazolium, hydroxide, inner salt
3-[2-[[[2-(Tetradecyloxy)-5-methylphenoxy]hydroxyphosphinyl]oxy]phenyl]
methyl]-4-methylthiazolium, hydroxide, inner salt
3-[2-[[[2-(Tetradecyloxy)-5-methoxyphenoxy]hydroxyphosphinyl]oxy]phenyl]
methyl]thiazolium, hydroxide, inner salt
3-[2-[[[2-(Tetradecyloxy)-5-methoxyphenoxy]hydroxyphosphinyl]oxy]phenyl]
methyl]-5-methylthiazolium, hydroxide, inner salt
3-[2-[[[2-(Tetradecyloxy)-5-methoxyphenoxy]hydroxyphosphinyl]oxy]phenyl]
methyl]-4-methylthiazolium, hydroxide, inner salt
3-[2-[[[2-(Tetradecyloxy)-3-chlorophenoxy]hydroxyphosphinyl]oxy]phenyl]
methyl]thiazolium, hydroxide, inner salt
3-[2-[[[2-(Tetradecyloxy)-3-chlorophenoxy]hydroxyphosphinyl]oxy]phenyl]
methyl]-4-methylthiazolium, hydroxide, inner salt
3-[2-[[[2-(Dodecyloxy)phenoxy]hydroxyphosphinyl]oxy]phenyl]
methyl]thiazolium, hydroxide, inner salt
3-[2-[[[2-(Dodecyloxy)phenoxy]hydroxyphosphinyl]oxy]phenyl]
methyl]-4-methylthiazolium, hydroxide, inner salt
3-[2-[[[2-(Dodecyloxy)-5-methylphenoxy]hydroxyphosphinyl]oxy]phenyl]
methyl]thiazolium, hydroxide, inner salt
3-[2-[[[2-(Dodecyloxy)-5-methylphenoxy]hydroxyphosphinyl]oxy]phenyl]
methyl]-4-methylthiazolium, hydroxide, inner salt
3-[2-[[[2-(Dodecyloxy)-5-methoxyphenoxy]hydroxyphosphinyl]oxy]phenyl]
methyl]thiazolium, hydroxide, inner salt
3-[2-[[[2-(Dodecyloxy)-3-chlorophenoxy]hydroxyphosphinyl]oxy]phenyl]
methyl]thiazolium, hydroxide, inner salt
3-[2-[[[2-(Dodecyloxy)-3-chlorophenoxy]hydroxyphosphinyl]oxy]phenyl]
methyl]-4-methylthiazolium, hydroxide, inner salt
3-[2-[[[4-(Hexadecyloxy)phenoxy]hydroxyphosphinyl]oxy]phenyl]
methyl]thiazolium, hydroxide, inner salt
3-[2-[[[4-(Hexadecyloxy)phenoxy]hydroxyphosphinyl]oxy]phenyl]
methyl]-5-methylthiazolium, hydroxide, inner salt
3-[2-[[[4-(Hexadecyloxy)-2-methylphenoxy]hydroxyphosphinyl]oxy]phenyl]
methyl]thiazolium, hydroxide, inner salt
3-[2-[[[4-(Hexadecyloxy)-2-methylphenoxy]hydroxyphosphinyl]oxy]phenyl]
methyl]-5-methylthiazolium, hydroxide, inner salt
3-[2-[[[4-(Hexadecyloxy)-2-methoxyphenoxy]hydroxyphosphinyl]oxy]phenyl]
methyl]thiazolium, hydroxide, inner salt
3-[2-[[[4-(Hexadecyloxy)-2-methoxyphenoxy]hydroxyphosphinyl]oxy]phenyl]
methyl]-5-methylthiazolium, hydroxide, inner salt
3-[2-[[[4-(Hexadecyloxy)-2-nitrophenoxy]hydroxyphosphinyl]oxy]phenyl]
methyl]thiazolium, hydroxide, inner salt
3-[2-[[[4-(Hexadecyloxy)-2-carbomethoxyphenoxy]hydroxyphosphinyl]oxy]phenyl]
methyl]thiazolium, hydroxide, inner salt
3-[2-[[[4-(Hexadecyloxy)-2-carbomethoxyphenoxy]hydroxyphosphinyl]oxy]phenyl]
methyl]-5-methylthiazolium, hydroxide, inner salt
3-[2-[[[4-(Hexadecyloxy)-2,5-di-t-butylphenoxy]hydroxlhosphinyl]oxy]phenyl]
methyl]thiazolium, hydroxide, inner salt
3-[2-[[[4-(Hexadecyloxy)-2,5-di-t-butylphenoxy]hydroxhosphinyl]oxy]phenyl]
methyl]-5-methylthiazolium, hydroxide, inner salt
3-[2-[[[4-(Hexadecyloxy)-2,5-dichlorophenoxhydroxyphosphinyl]oxy]phenyl]
methyl]thiazolium, hydroxide, inner salt
3-[2-[[[4-(Hexadecyloxy)-2-chlorophenoxy]hydroxyphosphinyl]oxy]phenyl]
methyl]thiazolium, hydroxide, inner salt
3-[2-[[[4-(Hexadecyloxy)-2-chlorophenoxhydroxyphosphinyl]oxy]phenyl]
methyl]-5-methylthiazolium, hydroxide, inner salt
3-[2-[[[4-(Hexadecyloxy)-3-chlorophenoxy]hydrophosphinyl]oxy]phenyl]
methyl]thiazolium, hydroxide, inner salt
3-[2-[[[4-(Hexadecyloxy)-3-chlorophenoxy]hydroxyphosphinyl]oxy]phenyl]

TABLE II-continued methyl]-5-methylthiazolium, hydroxide, inner salt
3-[2-[[[4-(Tetradecyloxy)phenoxy]hydroxyphosphinyl]oxy]phenyl]
methyl]thiazolium, hydroxide, inner salt
3-[2-[[[4-(Tetradecyloxy)phenoxy]hydroxyphosphinyl]oxy]phenyl]
methyl]-5-methylthiazolium, hydroxide, inner salt
3-[2-[[[4-(Tetradecyloxy)phenoxy]hydroxyphosphinyl]oxy]phenyl]
methyl]-4-methylthiazolium, hydroxide, inner salt
3-[2-[[[4-(Tetradecyloxy)-2-methylphenoxy]hydroxyphosphinyl]oxy]phenyl]
methyl]thiazolium, hydroxide, inner salt
3-[2-[[[4-(Tetradecyloxy)-2-methylphenoxy]hydroxyphosphinyl]oxy]phenyl]
methyl]-5-methylthiazolium, hydroxide, inner salt
3-[2-[[[4-(Tetradecyloxy)-2-methoxyphenoxy]hydroxyphosphinyl]oxy]phenyl]
methyl]thiazolium, hydroxide, inner salt
3-[2-[[[4-(Tetradecyloxy)-2-methoxyphenoxy]hydroxyphosphinyl]oxy]phenyl]
methyl]-5-methylthiazolium, hydroxide, inner salt
3-[2-[[[4-(Tetradecyloxy)-2-methoxyphenoxy]hydroxyphosphinyl]oxy]phenyl]
methyl]-4-methylthiazolium, hydroxide, inner salt
3-[2-[[[4-(Tetradecyloxy)-2-nitrophenoxy]hydroxyphosphinyl]oxy]phenyl]
methyl]thiazolium, hydroxide, inner salt
3-[2-[[[4-(Tetradecyloxy)-2-nitrophenoxy]hydrox,phosphinyl]oxy]phenyl]
methyl]-5-methylthiazolium, hydroxide, inner salt
3-[2-[[[4-(Tetradecyloxy)-2-nitrophenoxy]hydroxyphosphinyl]oxy]phenyl]
methyl]-4-methylthiazolium, hydroxide, inner salt
3-[2-[[[4-(Tetradecyloxy)-2-carbomethoxyphenoxy]hydroxyphosphinyl]oxy]phenyl]
methyl]thiazolium, hydroxide, inner salt
3-[2-[[[4-(Tetradecyloxy)-2-carbomethoxyphenoxy]hydroxyphosphinyl]oxy]phenyl]
methyl]-5-methylthiazolium, hydroxide, inner salt
3-[2-[[[4-(Tetradecyloxy)-2-carbomethoxyphenoxy]hydroxyphosphinyl]oxy]phenyl]
methyl]-4-methylthiazolium, hydroxide, inner salt
3-[2-[[[4-(Tetradecyloxy)-2,5-di-t-butylphenoxy]hydroxyphosphinyl]oxy]phenyl]
methyl]thiazolium, hydroxide, inner salt
3-[2-[[[4-(Tetradecyloxy)-2,5-di-t-butylphenoxy]hydroxyphosphinyl]oxy]phenyl]
methyl]-5-methylthiazolium, hydroxide, inner salt
3-[2-[[[4-(Tetradecyloxy)-2,5-di-t-butylphenoxy]hydroxyphosphinyl]oxy]phenyl]
methyl]-4-methylthiazolium, hydroxide, inner salt
3-[2-[[[4-(Tetradecyloxy)-2,5-dichlorophenoxy]hydroxyphosphinyl]oxy]phenyl]
methyl]thiazolium, hydroxide, inner salt
3-[2-[[[4-(Tetradecyloxy)-2,5-dichlorophenoxy]hydroxyphosphinyl]oxy]phenyl]
methyl]-4-methylthiazolium, hydroxide, inner salt
3-[2-[[[4-(Tetradecyloxy)-2-chlorophenoxy]hydroxhosphinyl]oxy]phenyl]
methyl]thiazolium, hydroxide, inner salt
3-[2-[[[4-(Tetradecyloxy)-2-chlorophenoxy]hydroxhosphinyl]oxy]phenyl]
methyl]-5-methylthiazolium, hydroxide, inner salt
3-[2-[[[4-(Tetradecyloxy)-2-chlorophenoxy]hydroxyphosphinyl]oxy]phenyl]
methyl]-4-methylthiazolium, hydroxide, inner salt
3-[2[[[4-(Tetradecyloxy)-3-chlorophenoxy]hydroxyphosphinyl]oxy]phenyl]
methyl]thiazolium, hydroxide, inner salt
3-[2-[[[4-(Tetradecyloxy)-3-chlorophenoxy]hydroxyphosphinyl]oxy]phenyl]
methyl]-5-methylthiazolium, hydroxide, inner salt
3-[2-[[[4-(Tetradecyloxy)-3-chlorophenoxy]hydroxyphosphinyl]oxy]phenyl]
methyl])-4-methylthiazolium, hydroxide, inner salt
3-[2-[[[4-(Dodecyloxy)phenoxy]hydroxyphosphinyl]oxy]phenyl]
methyl]thiazolium, hydroxide, inner salt
3-[2-[[[4-(Dodecyloxy)-2-methylphenoxy]hydroxyphosphinyl]oxy]phenyl]
methyl]thiazolium, hydroxide, inner salt
3-[2-[[[4-(Dodecyloxy)-2-methylphenoxy]hydroxyphosphinyl]oxy]phenyl]
methyl]-4-methylthiazolium, hydroxide, inner salt
3-[2-[[[4-(Dodecyloxy)-2-methoxyphenoxy]hydroxyphosphinyl]oxy]phenyl]
methyl]thiazolium, hydroxide, inner salt
3-[2-[[[4-(Dodecyloxy)-2-methoxyphenoxy]hydroxyphosphinyl]oxy]phenyl]
methyl]-4-methylthiazolium, hydroxide, inner salt
3-[2-[[[4-(Dodecyloxy)-2-nitrophenoxy]hydroxyphosphinyl]oxy]phenyl]
methyl]thiazolium, hydroxide, inner salt
3-[2-[[[4-(Dodecyloxy)-2-carbomethoxyphenoxy]hydroxyphosphinyl]oxy]phenyl]
methyl]thiazolium, hydroxide, inner salt
3-[2-[[[4-(Dodecyloxy)-2-carbomethoxyphenoxy]hydroxyphosphinyl]oxy]phenyl]
methyl]-4-methylthiazolium, hydroxide, inner salt
3-[2-[[[4-(Dodecyloxy)-2,5-di-t-butylphenoxy]hydroxyphosphinyl]oxy]phenyl]
methyl]thiazolium, hydroxide, inner salt
3-[2-[[[4-(Dodecyloxy)-2,5-di-t-butylphenoxy]hydroxyphosphinyl]oxy]phenyl]
methyl]-4-methylthiazolium, hydroxide, inner salt
3-[2-[[[4-(Dodecyloxy)-2,5-dichlorophenoxy]hydroxyphosphinyl]oxy]phenyl]
methyl]thiazolium, hydroxide, inner salt
3-[2-[[[4-(Dodecyloxy)-2,5-dichlorophenoxy]hydroxyphosphinyl]oxy]phenyl]
methyl]-4-methylthiazolium, hydroxide, inner salt
3-[2-[[[4-(Dodecyloxy)-2-chlorophenoxy]hydroxyphosphinyl]oxy]phenyl]
methyl]thiazolium, hydroxide, inner salt
3-[2-[[[4-(Dodecyloxy)-2-chlorophenoxy]hydroxyphosphinyl]oxy]phenyl]
methyl]-4-methylthiazolium, hydroxide, inner salt
3-[2-[[[4-(Dodecyloxy)-3-chlorophenoxy]hydroxyphosphinyl]oxy]phenyl]
methyl thiazolium, hydroxide, inner salt
3-[2-[[[4-(Dodecyloxy)-3-chlorophenoxy]hydroxyphosphinyl]oxy]phenyl]

TABLE II-continued methyl]-4-methylthiazolium, hydroxide, inner salt
3-[4-[[[3-(Hexadecyloxy)phenoxy]hydroxyphosphinyl]oxy]phenyl]
methyl]thiazolium, hydroxide, inner salt
3-[4-[[[3-(Hexadecyloxy)phenoxy]hydroxyphosphinyl]oxy]phenyl]
methyl]-5-methylthiazolium, hydroxide, inner salt
3-[4-[[[3-(Hexadecyloxy)-2-methylphenoxy]hydroxyphosphinyl]oxy]phenyl]
methyl]thiazolium, hydroxide, inner salt
3-[4-[[[3-(Hexadecyloxy)-2-methylphenoxy]hydroxyphosphinyl]oxy]phenyl]
methyl]-5-methylthiazolium, hydroxide, inner salt
3-[4-[[[3-(Hexadecyloxy)-2-methoxyphenoxy]hydroxyphosphinyl]oxy]phenyl]
methyl]thiazolium, hydroxide, inner salt
3-[4-[[[3-(Hexadecyloxy)-2-methoxyphenoxy]hydroxyphosphinyl]oxy]phenyl]
methyl]-5-methylthiazolium, hydroxide, inner salt
3-[4-[[[3-(Hexadecyloxy)-2-nitrophenoxy]hydroxyphosphinyl]oxy]phenyl]
methyl]thiazolium, hydroxide, inner salt
3-[4-[[[3-(Hexadecyloxy)-2-nitrophenoxy]hydroxyphosphinyl]oxy]phenyl]
methyl]-5-methylthiazolium, hydroxide, inner salt
3-[4-[[[3-(Hexadecyloxy)-2-carbomethoxyphenoxy]hydroxyphosphinyl]oxy]phenyl]
methyl]thiazolium, hydroxide, inner salt
3-[4-[[[3-(Hexadecyloy)-5-methylphenoy]hydroxyphosphinyl]oxy]phenyl]
methyl]thiazolium, hydroxide, inner salt
3-[4-[[[3-(Hexadecyloy)-5-methylphenoxy]hydroxyphosphinyl]oxy]phenyl]
methyl]-5-methylthiazolium, hydroxide, inner salt
3-[4-[[[3-(Hexadecyloxy)-5-methoxyphenoxy]hydroxyphosphinyl]oxy]phenyl]
methyl]thiazolium, hydroxide, inner salt
3-[4-[[[3-(Hexadecyloxy)-5-methoxyphenoxy]hydroxyphosphinyl]oxy]phenyl]
methyl]-5-methylthiazolium, hydroxide, inner salt
3-[4-[[[3-(Tetradecyloxy)phenoxy]hydroxyphosphinyl]oxy]phenyl]
methyl]thiazolium, hydroxide, inner salt
3-[4-[[[3-(Tetradecyloxy)phenoxy]hydroxyphosphinyl]oxy]phenyl]
methyl]-5-methylthiazolium, hydroxide, inner salt
3-[4-[[[3-(Tetradecyloxy)phenoxy]hydroxyphosphinyl]oxy]phenyl]
methyl]-4-methylthiazolium, hydroxide, inner salt
3-[4-[[[3-(Tetradecyloxy)-2-methylphenoxy]hydroxyphosphinyl]oxy]phenyl]
methyl]thiazolium, hydroxide, inner salt
3-[4-[[[3-(Tetradecyloxy)-2-methylphenoxy]hydroxyphosphinyl]oxy]phenyl]
methyl]-4-methylthiazolium, hydroxide, inner salt
3-[4-[[[3-(Tetradecyloxy)-2-methoxyphenoxy]hydroxyphosphinyl]oxy]phenyl]
methyl]thiazolium, hydroxide, inner salt
3-[4-[[[3-(Tetradecyloxy)-2-methoxyphenoxy]hydroxyphosphinyl]oxy]phenyl]
methyl]-5-methylthiazolium, hydroxide, inner salt
3-[4-[[[3-(Tetradecyloxy)-2-methoxyphenoxy]hydroxyphosphinyl]oxy]phenyl]
methyl]-4-methylthiazolium, hydroxide, inner salt
3-[4-[[[3-(Tetradecylox-2-nitrophenoxy]hydroxyphosphinyl]oxy]phenyl]
methyl]thiazolium, hydroxide, inner salt
3-[4-[[[3-(Tetradecyloxy)-2-nitrophenoxy]hydroxyphosphinyl]oxy]phenyl]
methyl]-5-methylthiazolium, hydroxide, inner salt
3-[4-[[[3-(Tetradecyloxy)-2-carbomethoxyphenoxy]hydroxyphosphinyl]oxy]phenyl]
methyl]thiazolium, hydroxide, inner salt
3-[4-[[[3-(Tetradecyloxy)-2-carbomethoxyphenoxy]hydroxyphosphinyl]oxy]phenyl]
methyl]-5-methylthiazolium, hydroxide, inner salt
3-[4-[[[3-(Tetradecyloxy)-2-carbomethoxyphenoxy]hydroxyphosphinyl]oxy]phenyl]
methyl]-4-methylthiazolium, hydroxide, inner salt
3-[4-[[[3-(Tetradecyloxy)-5-methylphenoxy]hydroxyphosphinyl]oxy]phenyl]
methyl]thiazolium, hydroxide, inner salt
3-[4-[[[3-(Tetradecyloxy)-5-methylphenoxy]hydroxyphosphinyl]oxy]phenyl]
methyl]-5-methylthiazolium, hydroxide, inner salt
3-[4-[[[3-(Tetradecyloxy)-5-methylphenoxy]hydroxyphosphinyl]oxy]phenyl]
methyl]-4-methylthiazolium, hydroxide, inner salt
3-[4-[[[3-(Tetradecyloxy)-5-methoxyphenoxy]hydroyphosphinyl]oxy]phenyl]
methyl]thiazolium, hydroxide, inner salt
3-[4-[[[3-(Tetradecyloxy)-5-methoxyphenoxy]hydroxyphosphinyl]oxy]phenyl]
methyl]-5-methylthiazolium, hydroxide, inner salt
3-[4-[[[3-(Dodecyloxy)phenoxy]hydroxyphosphinyl]oxy]phenyl]
methyl]thiazolium, hydroxide, inner salt
3-[4-[[[3-(Dodecyloxy)phenoxy]hydroxyphosphinyl]oxy]phenyl]
methyl]-4-methylthiazolium, hydroxide, inner salt
3-[4-[[[3-(Dodecyloxy)-2-methylphenoxy]hydroxyphosphinyl]oxy]phenyl]
methyl]thiazolium, hydroxide, inner salt
3-[4[[[3-(Dodecyloxy)-2-methylphenoxy]hydroxyphosphinyl]oxy]phenyl]
methyl]-4-methylthiazolium, hydroxide, inner salt
3-[4-[[[3-(Dodecyloxy)-2-methoxyphenoxy]hydroxyphosphinyl]oxy]phenyl]
methyl]thiazolium, hydroxide, inner salt
3-[4-[[[3-(Dodecyloxy)-2-nitrophenoxy]hydroxyphosphinyl]oxy]phenyl]
methyl]thiazolium, hydroxide, inner salt
3-[4-[[[3-(Dodecyloxy)-2-nitrophenoxy]hydroxyphosphinyl]oxy]phenyl]
methyl]-4-methylthiazolium, hydroxide, inner salt
3-[4-[[[3-(Dodecyloxy)-2-carbomethoxyphenoxy]hydroxyphosphinyl]oxy]phenyl]
methyl]thiazolium, hydroxide, inner salt
3-[4-[[[3-(Dodecyloxy)-2-carbomethoxyphenoxy]hydroxyphosphinyl]oxy]phenyl]
methyl]-4-methylthiazolium, hydroxide, inner salt
3-[4-[[[3-(Dodecyloxy)-5-methylphenoxy]hydroxyphosphinyl]oxy]phenyl]

TABLE II-continued methyl]thiazolium, hydroxide, inner salt
3-[4-[[[3-(Dodecyloxy)-5-methylphenoxy]hydroxyphosphinyl]oxy]phenyl]
methyl]-4-methylthiazolium, hydroxide, inner salt
3-[4-[[[3-(Dodecyloxy)-5-methoxyphenoxy]hydroxyphosphinyl]oxy]phenyl]
methyl]thiazolium, hydroxide, inner salt
3-[4-[[[3-(Dodecyloxy)-5-methoxyphenoxy]hydroxyphosphinyl]oxy]phenyl]
methyl]-4-methylthiazolium, hydroxide, inner salt
3-[4-[[[2-(Hexadecyloxy)phenoxy]hydroyphosphinyl]oxy]phenyl]
methyl]thiazolium, hydroxide, inner salt
3-[4-[[[2-(Hexadecyloxy)-5-methylphenoxy]hydroxyphosphinyl]oxy]phenyl]
methyl]thiazolium, hydroxide, inner salt
3-[4-[[[2-(Hexadecyloxy)-5-methylphenoxy]hydroxyphosphinyl]oxy]phenyl]
methyl]-5-methylthiazolium, hydroxide, inner salt
3-[4-[[[2-(Hexadecyloxy)-5-methoxyphenoxy]hydroxyphosphinyl]oxy]phenyl]
methyl]thiazolium, hydroxide, inner salt
3-[4-[[[2-(Hexadecyloxy)-5-methoxyphenoxy]hydroxyphosphinyl]oxy]phenyl]
methyl]-5-methylthiazolium, hydroxide, inner salt
3-[4-[[[2-(Hexadecyloxy)-3-chlorophenoxy]hydroxyphosphinyl]oxy]phenyl]
methyl]thiazolium, hydroxide, inner salt
3-[4-[[[2-(Hexadecyloxy)-3-chlorophenoxylhydroxyphosphinyl]oxy]phenyl]
methyl]-5-methylthiazolium, hydroxide, inner salt
3-[4-[[[2-(Tetradecyloxy)phenoxy]hydroxyphosphinyl]oxy]phenyl]
methyl]thiazolium, hydroxide, inner salt
3-[4-[[[2-(Tetradecyloxy)phenoxy]hydroxyphosphinyl]oxy]phenyl]
methyl]-4-methylthiazolium, hydroxide, inner salt
3-[4-[[[2-(Tetradecyloxy)-5-methylphenoxy]hydroxyphosphinyl]oxy]phenyl]
methyl]thiazolium, hydroxide, inner salt
3-[4-[[[2-(Tetradecyloxy)-5-methylphenoxy]hydroxyphosphinyl]oxy]phenyl]
methyl]-4-methylthiazolium, hydroxide, inner salt
3-[4-[[[2-(Tetradecyloxy)-5-methoxyphenoxy]hydroxyphosphinyl]oxy]phenyl]
methyl]thiazolium, hydroxide, inner salt
3-[4-[[[2-(Tetradecyloxy)-5-methoxyphenoxy]hydroxyphosphinyl]oxy]phenyl]
methyl]-5-methylthiazolium, hydroxide, inner salt
3-[4-[[[2-(Tetradecyloxy)-5-methoxyphenoxy]hydroxyphosphinyl]oxy]phenyl]
methyl]-4-methylthiazolium, hydroxide, inner salt
3-[4-[[[2-(Tetradecyloxy)-3-chlorophenoxy]hydroxyphosphinyl]oxy]phenyl]
methyl]thiazolium, hydroxide, inner salt
3-[4-[[[2-(Tetradecyloxy)-3-chlorophenoxy]hydroxyphosphinyl]oxy]phenyl]
methyl]-4-methylthiazolium, hydroxide, inner salt
3-[4-[[[2-(Dodecyloxy)phenoxy]hydroxyphosphinyl]oxy]phenyl]
methyl]thiazolium, hydroxide, inner salt
3-[4-[[[2-(Dodecyloxy)phenoxy]hydroxyphosphinyl]oxy]phenyl]
methyl]-4-methylthiazolium, hydroxide, inner salt
3-[4-[[[2-(Dodecyloxy)-5-methylphenoxy]hydroxyphosphinyl]oxy]phenyl]
methyl]thiazolium, hydroxide, inner salt
3-[4-[[[2-(Dodecyloxy)-5-methylphenoxy]hydroxyphosphinyl]oxy]phenyl]
methyl]-4-methylthiazoliynm hydroxide, inner salt
3-[4-[[[2-(Dodecyloxy)-5-methoxyphenoxy]hydroxyphosphinyl]oxy]phenyl]
methyl]thiazolium, hydroxide, inner salt
3-[4-[[[2-(Dodecyloxy)-5-methoxyphenoxy]hydroxyphosphinyl]oxy]phenyl]
methyl]-4-methylthiazolium, hydroxide, inner salt
3-[4-[[[2-(Dodecyloxy)-3-chlorophenoxy]hydroxyphosphinyl]oxy]phenyl]
methyl]thiazolium, hydroxide, inner salt
3-[4-[[[4-(Hexadecyloxy)phenoxy]hydroxyphosphinyl]oxy]phenyl]
methyl]thiazolium, hydroxide, inner salt
3-[4-[[[4-(Hexadecyloxy)phenoxy]hydroxyphosphinyl]oxy]phenyl]
methyl]-5-methylthiazolium, hydroxide, inner salt
3-[4-[[[4-(Hexadecyloxy)-2-methylphenoxy]hydroxyphosphinyl]oxy]phenyl]
methyl]thiazolium, hydroxide, inner salt
3-[4-[[[4-(Hexadecyloxy)-2-methylphenoxy]hydroxyphosphinyl]oxy]phenyl]
methyl]-5-methylthiazolium, hydroxide, inner salt
3-[4-[[[4-(Hexadecyloxy)-2-methoxyphenoxy]hydroxhosphinyl]oxy]phenyl]
methyl]thiazolium, hydroxide, inner salt
3-[4[[[4-(Hexadecyloxy)-2-methoxyphenoxy]hydroxyphosphinyl]oxy]phenyl]
methyl]-5-methylthiazolium, hydroxide, inner salt
3-[4-[[[4-(Hexadecyloxy)-2-nitrophenoxy]hydroxyphosphinyl]oxy]phenyl]
methyl]thiazolium, hydroxide, inner salt
3-[4-[[[4-(Hexadecyloxy)-2-carbomethoxyphenoxy]hydroxyphosphinyl]oxy]phenyl]
methyl]thiazolium, hydroxide, inner salt
3-[4-[[[4-(Hexadeoyloxy)-2-carbomethoxyphenoxy]hydroxyphosphinyl]oxy]phenyl]
methyl]-5-methylthiazolium, hydroxide, inner salt
3-[4-[[[4-(Hexadecyloxy)-2,5-di-t-butylphenoxy]hydroxyphosphinyl]oxy]phenyl]
methyl]thiazolium, hydroxide, inner salt
3-[4-[[[4-(Hexadecyloxy)-2,5-di-t-butylphenoxy]hydroxyphosphinyl]oxy]phenyl]
methyl]-5-mthylthiazolium, hydroxide, inner salt
3-[4-[[[4-(Hexadecyloxy)-2,5-dichlorophenoxy]hydroxyphosphinyl]oxy]phenyl]
methyl]thiazolium, hydroxide, inner salt
3-[4-[[[4-(Hexadecyloxy)-2,5-dichlorophenoxy]hydroxyphosphinyl]oxy]phenyl]
methyl]-5-methylthiazolium, hydroxide, inner salt
3-[4-[[[4-(Hexadecyloxy)-2-chlorophenoxy]hydroxyphosphinyl]oxy]phenyl]
methyl]thiazolium, hydroide, inner salt
3-[4-[[[4-(Hexadecyloxy)-3-chlorophenoxy]hydroxyphosphinyl]oxy]phenyl]

TABLE II-continued methyl]thiazolium, hydroxide, inner salt
3-[4-[[[4-(Tetradecyloxy)phenoxy]hydroxyphosphinyl]oxy]phenyl]
methyl]thiazolium, hydroxide, inner salt
3-[4-[[[4-(Tetradecyloxy)phenoxy]hydroxyphosphinyl]oxy]phenyl]
methyl]-5-methylthiazolium, hydroxide, inner salt
3-[4-[[[4-(Tetradecyloxy)phenoxy]hydroxyphosphinyl]oxy]phenyl]
methyl]-4-methylthiazolium, hydroxide, inner salt
3-[4-[[[4-(Tetradecyloxy)-2-methylphenoxy]hydroxyphosphinyl]oxy]phenyl]
methyl]thiazolium, hydroxide, inner salt
3-[4-[[[4-(Tetradecyloxy)-2-methylphenoxy]hydroxyphosphinyl]oxy]phenyl]
methyl]-5-methylthiazolium, hydroxide, inner salt
3-[4-[[[4-(Tetradecyloxy)-2-methylphenoxy]hydroxyphosphinyl]oxy]phenyl]
methyl]-4-methylthiazolium, hydroxide, inner salt
3-[4-[[[4-(Tetradecyloxy)-2-methoxyphenoxy]hydroxyphosphinyl]oxy]phenyl]
methyl]thiazolium, hydroxide, inner salt
3-[4-[[[4-(Tetradecyloxy)-2-methoxyphenoxy]hydroxyphosphinyl]oxy]phenyl]
methyl]-5-methylthiazolium, hydroxide, inner salt
3-[4-[[[4-(Tetradecyloxy)-2-nitrophenoxy]hydroxyphosphinyl]oxy]phenyl]
methyl]thiazolium, hydroxide, inner salt
3-[4-[[[4-(Tetradecyloxy)-2-nitrophenoxy]hydroxyphosphinyl]oxy]phenyl]
methyl]-5-methylthiazolium, hydroxide, inner salt
3-[4-[[[4-(Tetradecyloxy)-2-nitrophenoxy]hydroxyphosphinyl]oxy]phenyl]
methyl]-4-methylthiazolium, hydroxide, inner salt
3-[4-[[[4-(Tetradecyloxy)-2-carbomethoxyphenoxy]hydroxyphosphinyl]oxy]phenyl]
methyl]thiazolium, hydroxide, inner salt
3-[4-[[[4-(Tetradecyloxy)-2-carbomethoxyphenoxy]hydroxyphosphinyl]oxy]phenyl]
methyl]-5-methylthiazolium, hydroxide, inner salt
3-[4-[[[4-(Tetradecyloxy)-2-carbomethoxyphenoxy]hydroxyphosphinyl]oxy]phenyl]
methyl]-4-methylthiazolium, hydroxide, inner salt
3-[4-[[[4-(Tetradecyloxy)-2,5-di-t-butylphenoxy]hydroxyphosphinyl]oxy]phenyl]
methyl]thiazolium, hydroxide, inner salt
3-[4-[[[4-(Tetradecyloxy)-2,5-di-t-butylphenoxy]hydroxyphosphinyl]oxy]phenyl]
methyl]-4-methylthiazolium, hydroxide, inner salt
3-[4-[[[4-(Tetradecyloxy)-2,5-dichlorophenoxy]hydroxyphosphinyl]oxy]phenyl]
methyl]thiazolium, hydroxide, inner salt
3-[4-[[[4-(Tetradecyloxy)-2,5-dichlorophenoxy]hydroxyphosphinyl]oxy]phenyl]
methyl]-5-methylthiazolium, hydroxide, inner salt
3-[4-[[[4-(Tetradecyloxy)-2,5-dichlorophenoxy]hydroxyphosphinyl]oxy]phenyl]
methyl]-4-methylthiazolium, hydroxide, inner salt
3-[4-[[[4-(Tetradecyloxy)-2-chlorophenoxy]hydroxyphosphinyl]oxy]phenyl]
methyl]thiazolium, hydroxide, inner salt
3-[4-[[[4-(Tetradecyloxy)-2-chlorophenoxy]hydroxyphosphinyl]oxy]phenyl]
methyl]-5-methylthiazolium, hydroxide, inner salt
3-[4-[[[4-(Tetradecyloxy)-3-chlorophenoxy]hydroxyphosphinyl]oxy]phenyl]
methyl]thiazolium, hydroxide, inner salt
3-[4-[[[4-(Tetradecyloxy)-3-chlorophenoxy]hydroxyphosphinyl]oxy]phenyl]
methyl]-4-methylthiazolium, hydroxide, inner salt
3-[4-[[[4-(Dodecyloxy)phenoxy]hydroxyphosphinyl]oxy]phenyl]
methyl]thiazolium, hydroxide, inner salt
3-[4-[[[4-(Dodecyloxy)phenoxy]hydroxyphosphinyl]oxy]phenyl]
methyl]-4-methylthiazolium, hydroxide, inner salt
3-[4-[[[4-(Dodecyloxy)-2-methylphenoxy]hydroxyphosphinyl]oxy]phenyl]
methyl]thiazolium, hydroxide, inner salt
3-[4-[[[4-(Dodecyloxy)-2-methylphenoxy]hydroxyphosphinyl]oxy]phenyl]
methyl]-4-methylthiazolium, hydroxide, inner salt
3-[4-[[[4-(Dodecyloxy)-2-methoxyphenoxy]hydroxyphosphinyl]oxy]phenyl]
methyl]thiazolium, hydroxide, inner salt
3-[4-[[[4-(Dodecyloxy)-2-methoxyphenoxy]hydroxyphosphinyl]oxy]phenyl]
methyl]-4-methylthiazolium, hydroxide, inner salt
3-[4-[[[4-(Dodecyloxy)-2-nitrophenoxy]hydroxyphosphinyl]oxy]phenyl]
methyl]thiazolium, hydroxide, inner salt
3-[4-[[[4-(Dodecyloxy)-2-carbomethoxyphenoxy]hydroxyphosphinyl]oxy]phenyl]
methyl]thiazolium, hydroxide, inner salt
3-[4-[[[4-(Dodecyloxy)-2-carbomethoxyphenoxy]hydroxyphosphinyl]oxy]phenyl]
methyl]-4-methylthiazolium, hydroxide, inner salt
3-[4-[[[4-(Dodecyloxy)-2,5-di-t-butylphenoxy]hydroxyphosphinyl]oxy]phenyl]
methyl]thiazolium, hydroxide, inner salt
3-[4-[[[4-(Dodecyloxy)-2,5-di-t-butylphenoxy]hydroxyphosphinyl]oxy]phenyl]
methyl]-4-methylthiazolium, hydroxide, inner salt
3-[4-[[[4-(Dodecyloxy)-2,5-dichlorophenoxy]hydroxyphosphinyl]oxy]phenyl]
methyl]thiazolium, hydroxide, inner salt
3-[4-[[[4-(Dodecyloxy)-2,5-dichlorophenoxy]hydroxyphosphinyl]oxy]phenyl]
methyl]-4-methylthiazolium, hydroxide, inner salt
3-[4-[[[4-(Dodecyloxy)-2-chlorophenoxy]hydroxyphosphinyl]oxy]phenyl]
methyl]thiazolium, hydroxide, inner salt
3-[4-[[[4-(Dodecyloxy)-3-chlorophenoxy]hydroxyphosphinyl]oxy]phenyl]
methyl]thiazolium, hydroxide, inner salt
3-[4-[[[4-(Dodecyloxy)-3-chlorophenoxy]hydroxyphosphinyl]oxy]phenyl]
methyl]-4-methylthiazolium, hydroxide, inner salt
1-[3-[[[3-(Hexadecyloxy)phenoxy]hydroxyphosphinyl]oxy]phenyl]
methyl]quinolinium, hydroxide, inner salt
1-[3-[[[3-(Hexadecyloxy)-2-methylphenoxy]hydroxyphosphinyl]oxy]phenyl]

TABLE II-continued methyl]quinolinium, hydroxide, inner salt
1-[3-[[[3-(Hexadecyloxy)-2-msthoxyphenoxy]hydroxyphosphinyl]oxy]phenyl]
methyl]quinolinium, hydroxide, inner salt
1-[3-[[[3-(Hexadecyloxy)-2-nitrophenoxy]hydroxyphosphinyl]oxy]phenyl]
methyl]quinolinium, hydroxide, inner salt
1-[3-[[[3-(Hexadecyloxy)-2-carbomethoxyphenoxy]hydroxyphosphinyl]oxy]phenyl]
methyl]quinolinium, hydroxide, inner salt
1-[3-[[[3-(Hexadecyloxy)-5-methylphenoxy]hydroxyphosphinyl]oxy]phenyl]
methyl]quinolinium, hydroxide, inner salt
1-[3-[[[3-(Tetradecyloxy)-2-methoxyphenoxy]hydroxyphosphinyl]oxy]phenyl]
methyl]pyridinium, hydroxide, inner salt
1-[3-[[[3-(Tetradecyloxy)-2-nitrophenoxy]hydroxyphosphinyl]oxy]phenyl]
methyl]pyridinium, hydroxide, inner salt
1-[3-[[[3-(Tetradecyloxy)-2-carbomethoxyphenoxy]hydroxyphosphinyl]oxy]phenyl]
methyl]pyridinium, hydroxide, inner salt
1-[3-[[[3-(Tetradecyloxy)-5-methylphenoxy]hydroxyphosphinyl]oxy]phenyl]
methyl]pyridinium, hydroxide, inner salt
1-[3-[[[3-(Tetradecyloxy)-5-methoxyphenoxy]hydroxyphosphinyl]oxy]phenyl]
methyl]pyridinium, hydroxide, inner salt
1-[3-[[[3-(Dodecyloxy)phenoxy]hydroxyphosphinyl]oxy]phenyl]
methyl]quinolinium, hydroxide, inner salt
1-[3-[[[3-(Dodecyloxy)-2-methylphenoxy)hydroxyphosphinyl]oxy]phenyl]
methyl]quinolinium, hydroxide, inner salt
1-[3-[[[3-(Dodecyloxy)-2-methoxyphenoxy]hydroxyphosphinyl]oxy]phenyl]
methyl]quinolinium, hydroxide, inner salt
1-[3-[[[3-(Dodecyloxy)-2-carbomethoxyphenoxy]hydroxyphosphinyl]oxy]phenyl]
methyl]quinolinium, hydroxide, inner salt
1-[3-[[[3-(Dodecyloxy)-5-methylphenoxy]hydroxyphosphinyl]oxy]phenyl]
methyl]quinolinium, hydroxide, inner salt
1-[3-[[[3-(Dodecyloxy)-5-methoxyphenoxy]hydroxyphosphinyl]oxy]phenyl]
methyl]quinolinium, hydroxide, inner salt
1-[3-[[[2-(Hexadecyloxy)phenoxy]hydroxyphosphinyl]oxy]phenyl]
methyl]quinolinium, hydroxide, inner salt
1-[3-[[[2-(Hexadecyloxy)-5-methylphenoxy]hydroxyphosphinyl]oxy]phenyl]
methyl]quinolinium, hydroxide, inner salt
1-[3-[[[2-(Hexadecyloxy)-5-methoxyphenoxy]hydroxyphosphinyl]oxy]phenyl]
methyl]quinolinium, hydroxide, inner salt
1-[3-[[[2-(Hexadecyloxy)-3-chlorophenoxy]hydroxyphosphinyl]oxy]phenyl]
methyl]quinolinium, hydroxide, inner salt
1-[3-[[[2-(Tetradecyloxy)phenoxy]hydroxyphosphinyl]oxy]phenyl]
methyl]pyridinium, hydroxide, inner salt
1-[3-[[[2-(Tetradecyloxy)-5-methoxyphenoxy]hydroxyphosphinyl]oxy]phenyl]
methyl]pyridinium, hydroxide. inner salt
1-[3-[[[2-(Tetradecyloxy)-3-chlorophenoxy]hydroxyphosphinyl]oxy]phenyl]
methyl]pyridinium, hydroxide, inner salt
1-[3-[[[2-(Dodecyloxy)phenoxy]hydroxyphosphinyl]oxy]phenyl]
methyl]quinolinium, hydroxide. inner salt
1-[3-[[[2-(Dodecyloxy)-5-methylphenoxy]hydroxyphosphinyl]oxy]phenyl]
methyl]quinolinium, hydroxide, inner salt
1-[3-[[[2-(Dodecyloxy)-5-methoxyphenoxy]hydroxyphosphinyl]oxy]phenyl]
methyl]quinolinium, hydroxide, inner salt
1-[3-[[[2-(Dodecyloxy)-3-chlorophenoxy]hydroxyphosphinyl]oxy]phenyl]
methyl]quinolinium, hydroxide, inner salt
1-[3-[[[4-(Hexadecyloxy)phenoxy]hydroxyphosphinyl]oxy]phenyl]
methyl]quinolinium, hydroxide, inner salt
1-[3-[[[4-(Hexadecyloxy)-2-nitrophenoxy]hydroxyphosphinyl]oxy]phenyl]
methyl]quinolinium, hydroxide. inner salt
1-[3-[[[4-(Hexadecyloxy)-2-carbomethoxyphenoxy]hydroxyphosphinyl]oxy]phenyl]
methyl]quinolinium, hydroxide, inner salt
1-[3-[[[4-(Hexadecyloxy)-2,5-di-t-butylphenoxy]hydroxyphosphinyl]oxy]phenyl]
methyl]quinolinium, hydroxide, inner salt
1-[3-[[[4-(Hexadecyloxy)-2,5-dichlorophenoxy]hydroxyphosphinyl]oxy]phenyl]
methyl]quinolinium, hydroxide, inner salt
1-[3-[[[4-(Hexadecyloxy)-2-chlorophenoxy]hydroxyphosphinyl]oxy]phenyl]
methyl]quinolinium, hydroxide, inner salt
1-[3-[[[4-(Tetradecyloxy)phenoxy]hydroxyphosphinyl]oxy]phenyl]
methyl]pyridinium, hydroxide, inner salt
1-[3-[[[4-(Tetradecyloxy)-2-nitrophenoxy]hydroxyphosphinyl]oxy]phenyl]
methyl]pyridinium, hydroxide. inner salt
1-[3-[[[4-(Tetradecyloxy)-2-carbomethoxyphenoxy]hydroxyphosphinyl]oxy]phenyl]
methyl]pyridinium, hydroxide, inner salt
1-[3-[[[4-(Tetradecyloxy)-2,5-di-t-butylphenoxy]hydroxyphosphinyl]oxy]phenyl]
methyl]pyridinium. hydroxide, inner salt
1-[3-[[[4-(Tetradecyloxy)-2,5-dichlorophenoxyhydroxyphosphinyl]oxy]phenyl]
methyl]pyridinium. hydroxide. inner salt
1-[3-[[[4-(Tetradecyloxy)-2-chlorophenoxy]hydroxyphosphinyl]oxy]phenyl]
methyl]pyridinium, hydroxide, inner salt
1-[3-[[[4-(Tetradecyloxy)-3-chlorophenoxy]hydroxyphosphinyl]oxy]phenyl]
methyl]pyridinium, hydroxide. inner salt
1-[3-[[[4-(Dodecyloxy)phenoxy]hydroxyphosphinyl]oxy]phenyl]
methyl]quinolinium, hydroxide, inner salt
1-[3-[[[4-(Dodecyloxy)-2-methylphenoxy]hydroxyphosphinyl]oxy]phenyl]

TABLE II-continued methyl]quinolinium, hydroxide, inner salt
1-[3-[[[4-(Dodecyloxy)-2-carbomethoxyphenoxy]hydroxyphosphinyl]oxy]phenyl]
methyl]quinolinium, hydroxide, inner salt
1-[3-[[[4-(Dodecyloxy)-2,5-di-t-butylphenoxy]hydroxyphosphinyl]oxy]phenyl]
methyl]quinolinium, hydroxide, inner salt
1-[3-[[[4-(Dodecyloxy)-2,5-dichlorophenoxy]hydroxyphosphinyl]oxy]phenyl]
methyl]quinolinium, hydroxide, inner salt
1-[3-[[[4-(Dodecyloxy)-2-chlorophenoxy]hydroxyphosphinyl]oxy]phenyl]
methyl]quinolinium, hydroxide, inner salt
1-[3-[[[4-(Dodecyloxy)-3-chlorophenoxy]hydroxyphosphinyl]oxy]phenyl]
methyl]quinolinium, hydroxide, inner salt
1-[2-[[[3-(Hexadecyloxy)phenoxy]hydroxyphosphinyl]oxy]phenyl]
methyl]quinolinium, hydroxide, inner salt
1-[2-[[[3-(Hexadecyloxy)-2-methylphenoxy]hydroxyphosphinyl]oxy]phenyl]
methyl]quinolinium, hydroxide, inner salt
1-[2-[[[3-(Hexadecyloxy)-2-methoxyphenoxy]hydroxyphosphinyl]oxy]phenyl]
methyl]quinolinium, hydroxide, inner salt
1-[2-[[[3-(Hexadecyloxy)-5-methylphenoxy]hydroxyphosphinyl]oxy]phenyl]
methyl]quinolinium, hydroxide, inner salt
1-[2-[[[3-(Hexadecyloxy)-5-methoxyphenoxy]hydroxyphosphinyl]oxy]phenyl]
methyl]quinolinium, hydroxide, inner salt
1-[2-[[[3-(Tetradecyloxy)phenoxy]hydroxyphosphinyl]oxy]phenyl]
methyl]pyridinium, hydroxide, inner salt
1-[2-[[[3-(Tetradecyloxy)-2-methoxyphenoxy]hydroxyphosphinyl]oxy]phenyl]
methyl]pyridinium, hydroxide, inner salt
1-[2-[[[3-(Tetradecyloxy)-2-nitrophenoxy]hydroxyphosphinyl]oxy]phenyl]
methyl]pyridinium, hydroxide, inner salt
1-[2-[[[3-(Tetradecyloxy)-2-carbomethoxyphenoxy]hydroxyphosphinyl]oxy]phenyl]
methyl]pyridinium, hydroxide, inner salt
1-[2-[[[3-(Tetradecyloxy)-5-methoxyphenoxy]hydroxyphosphinyl]oxy]phenyl]
methyl]pyridinium, hydroxide, inner salt
1-[2-[[[3-(Dodecyloxy)phenoxy]hydroxyphosphinyl]oxy]phenyl]
methyl]quinolinium, hydroxide, inner salt
1-[2-[[[3-(Dodecyloxy)-2-methylphenoxy]hydroxyphosphinyl]oxy]phenyl]
methyl]quinolinium, hydroxide, inner salt
1-[2-[[[3-(Dodecyloxy)-2-methoxyphenoxy]hydroxyphosphinyl]oxy]phenyl]
methyl]quinolinium, hydroxide, inner salt
1-[2-[[[3-(Dodecyloxy)-2-nitrophenoxy]hydroxyphosphinyl]oxy]phenyl]
methyl]quinolinium, hydroxide, inner salt
1-[2-[[[3-(Dodecyloxy)-2-carbomethoxyphenoxy]hydroxyphosphinyl]oxy]phenyl]
methyl]quinolinium, hydroxide, inner salt
1-[2-[[[3-(Dodecyloxy)-5-methoxyphenoxy]hydroxyphosphinyl]oxy]phenyl]
methyl]quinolinium, hydroxide, inner salt
1-[2-[[[2-(Hexadecyloxy)phenoxy]hydroxyphosphinyl]oxy]phenyl]
methyl]quinolinium, hydroxide, inner salt
1-[2-[[[2-(Hexadecyloxy)-5-methylphenoxy]hydroxyphosphinyl]oxy]phenyl]
methyl]quinolinium, hydroxide, inner salt
1-[2-[[[2-(Hexadecyloxy)-5-methoxyphenoxy]hydroxyphosphinyl]oxy]phenyl]
methyl]quinolinium, hydroxide, inner salt
1-[2-[[[2-(Hexadecyloxy)-3-chlorophenoxy]hydroxyphosphinyl]oxy]phenyl]
methyl]quinolinium, hydroxide, inner salt
1-[2-[[[2-(Tetradecyloxy)phenoxy]hydroxyphosphinyl]oxy]phenyl]
methyl]pyridinium, hydroxide, inner salt
1-[2-[[[2-(Dodecyloxy)phenoxy]hydroxyphosphinyl]oxy]phenyl]
methyl]quinolinium, hydroxide, inner salt
1-[2-[[[2-(Dodecyloxy)-5-methylphenoxy]hydroxyphosphinyl]oxy]phenyl]
methyl]quinolinium, hydroxide, inner salt
1-[2-[[[2-(Dodecyloxy)-5-methoxyphenoxy]hydroxyphosphinyl]oxy]phenyl]
methyl]quinolinium, hydroxide, inner salt
1-[2-[[[2-(Dodecyloxy)-3-chlorophenoxy]hydroxyphosphinyl]oxy]phenyl]
methyl]quinolinium, hydroxide, inner salt
1-[2-[[[4-(Hexadeoyloxy)phenoxy]hydroxyphosphinyl]oxy]phenyl]
methyl]quinolinium, hydroxide, inner salt
1-[2-[[[4-(Hexadecyloxy)-2-methylphenoxy)hydroxyphosphinyl]oxy]phenyl]
methyl]quinolinium, hydroxide, inner salt
1-[2-[[[4-(Hexadecyloxy)-2-methoxyphenoxy]hydroxyphosphinyl]oxy]phenyl]
methyl]quinolinium, hydroxide, inner salt
1-[2-[[[4-(Hexadecyloxy)-2-nitrophenoxy]hydroxyphosphinyl]oxy]phenyl]
methyl]quinolinium, hydroxide, inner salt
1-[2-[[[4-(Hexadecyloxy)-2-carbomethoxyphenoxy]hydroxyphosphinyl]oxy]phenyl]
methyl]quinolinium, hydroxide, inner salt
1-[2-[[[4-(Hexadecyloxy)-2,5-di-t-butylphenoxy]hydroxyphosphinyl]oxy]phenyl]
methyl]quinolinium, hydroxide, inner salt
1-[2-[[[4-(Hexadecyloxy)-2,5-dichlorophenoxy]hydroxyphosphinyl]oxy]phenyl]
methyl]quinolinium, hydroxide, inner salt
1-[2-[[[4-(Hexadecyloxy)-3-chlorophenoxy]hydroxyphosphinyl]oxy]phenyl]
methyl]quinolinium, hydroxide, inner salt
1-[2-[[[4-(Tetradecyloxy)phenoxy]hydroxyphosphinyl]oxy]phenyl]
methyl]pyridinium, hydroxide, inner salt
1-[2-[[[4-(Tetradecyloxy)-2-methylphenoxy]hydroxyphosphinyl]oxy]phenyl]
methyl]pyridinium, hydroxide, inner salt
1-[2-[[[4-(Tetradecyloxy)-2-methoxyphenoxy]hydroxyphosphinyl]oxy]phenyl]

TABLE II-continued methyl]pyridinium, hydroxide, inner salt
1-[2-[[[4-(Tetradecyloxy)-2-nitrophenoxy]hydroxyphosphinyl]oxy]phenyl]
methyl]pyridinium, hydroxide, inner salt
1-[2-[[[4-(Tetradecyloxy)-3-chlorophenoxy]hydroxyphosphinyl]oxy]phenyl]
methyl]pyridinium, hydroxide, inner salt
1-[2-[[[4-(Dodecyloxy)phenoxy]hydroxyphosphinyl]oxy]phenyl]
methyl]quinolinium, hydroxide, inner salt
1-[2-[[[4-(Dodecyloxy)-2-methylphenoxy]hydroxyphosphinyl]oxy]phenyl]
methyl]quinolinium, hydroxide, inner salt
1-[2-[[[4-(Dodecyloxy)-2-methoxyphenoxy]hydroxyphosphinyl]oxy]phenyl]
methyl]quinolinium, hydroxide, inner salt
1-[2-[[4-(Dodecyloxy)-2-nitrophenoxy]hydroxyphosphinyl]oxy]phenyl]
methyl]quinolinium, hydroxide, inner salt
1-[2-[[[4-(Dodecyloxy)-2-carbomethoxyphenoxy]hydroxyphosphinyl]oxy]phenyl]
methyl]quinolinium, hydroxide, inner salt
1-[2-[[[4-(Dodecyloxy)-2,5-di-t-butylphenoxy]hydroxyphosphinyl]oxy]phenyl]
methyl]quinolinium, hydroxide, inner salt
1-[2-[[[4-(Dodecyloxy)-2,5-dichlorophenoxy]hydroxyphosphinyl]oxy]phenyl]
methyl]quinolinium, hydroxide, inner salt
1-[2-[[[4-(Dodecyloxy)-2-chlorophenoxy]hydroxyphosphinyl]oxy]phenyl]
methyl]quinolinium, hydroxide, inner salt
1-[2-[[[4-(Dodecyloxy)-3-chlorophenoxy]hydroxyphosphinyl]oxy]phenyl]
methyl]quinolinium, hydroxide, inner salt
1-[4-[[[3-(Hexadecyloxy)-2-methoxyphenoxy]hydroxyphosphinyl]oxy]phenyl]
methyl]quinolinium, hydroxide, inner salt
1-[4-[[[3-(Hexadecyloxy)-2-nitrophenoxy]hydroxyphosphinyl]oxy]phenyl]
methyl]quinolinium, hydroxide, inner salt
1-[4-[[[3-(Hexadecyloxy)-2-carbomethoxyphenoxy]hydroxyphosphinyl]oxy]phenyl]
methyl]quinolinium, hydroxide, inner salt
1-[4-[[[3-(Hexadecyloxy)-5-methylphenoxy]hydroxyphosphinyl]oxy]phenyl]
methyl]quinolinium, hydroxide, inner salt
1-[4-[[[3-(Hexadecyloxy)-5-methoxyphenoxy]hydroxyphosphinyl]oxy]phenyl]
methyl]quinolinium, hydroxide, inner salt
1-[4-[[[3-(Tetradecyloxy)-2-methoxyphenoxy]hydroxyphosphinyl]oxy]phenyl]
methyl]pyridinium, hydroxide, inner salt
1-[4-[[[3-(Tetradecyloxy)-2-nitrophenoxy]hydroxyphosphinyl]oxy]phenyl]
methyl]pyridinium, hydroxide, inner salt
1-[4-[[[3-(Tetradecyloxy)-2-carbomethoxyphenoxy]hydroxyphosphinyl]oxy]phenyl]
methyl]pyridinium, hydroxide, inner salt
1-[4-[[[3-(Tetradecyloxy)-5-methylphenoxy]hydroxyphosphinyl]oxy]phenyl]
methyl]pyridinium, hydroxide, inner salt
1-[4-[[[3-(Tetradecyloxy)-5-methoxyphenoxy]hydroxyphosphinyl]oxy]phenyl]
methyl]pyridinium, hydroxide, inner salt
1-[4-[[[3-(Dodecyloxy)phenoxy]hydroxyphosphinyl]oxy]phenyl]
methyl]quinolinium, hydroxide, inner salt
1-[4-[[[Dodecyloxy)-2-methylphenoxy]hydroxyphosphinyl]oxy]phenyl]
methyl]quinolinium, hydroxide, inner salt
1-[4-[[[3-(Dodecyloxy)-2-methoxyphenoxy]hydroxyphosphinyl]oxy]phenyl]
methyl]quinolinium, hydroxide, inner salt
1-[4-[[[3-(Dodecyloxy)-2-nitrophenoxy]hydroxyphosphinyl]oxy]phenyl]
methyl]quinolinium, hydroxide, inner salt
1-[4-[[[4-(Hexadecyloxy)-2,5-di-t-butylphenoxy]hydroxyphosphinyl]
methyl]quinolinium, hydroxide, inner salt
1-[4-[[[4-(Hexadecyloxy)-2,5-dichlorophenoxy]hydroxyphosphinyl]oxy]
methyl]quinolinium, hydroxide, inner, salt
1-[4-[[[4-(Hexadecyloxy)-2-chlorophenoxy]hydroxyphosphinyl]oxy]phenyl]
methyl]quinolinium, hydroxide, inner salt
1-[4-[[[4-(Tetradecyloxy)-2-methylphenoxy]hydroxyphosphinyl]oxy]phenyl]
methyl]pyridinium, hydroxide, inner salt
1-[4-[[[4-(Tetradecyloxy)-2-methoxyphenoxy]hydroxyphosphinyl]oxy]phenyl]
methyl]pyridinium, hydroxide, inner salt
1-[4-[[[4-(Tetradecyloxy)-2-nitrophenoxy]hydroxyphosphinyl]oxy]phenyl]
methyl]pyridinium, hydroxide, inner salt
1-[4-[[[4-(Tetradecyloxy)-2-carbomethoxyphenoxy]hydroxyphosphinyl]oxy]phenyl]
methyl]pyridinium, hydroxide, inner salt
1-[4-[[[4-(Tetradecyloxy)-2,5-di-t-butylphenoxy]hydroxyphosphinyl]oxy]phenyl]
methyl]pyridinium, hydroxide, inner salt
1-[4-[[[4-(Tetradecyloxy)-2,5-dichlorophenoxy]hydroxyphosphinyl]oxy]phenyl]
methyl]pyridinium, hydroxide, inner salt
1-[4-[[[4-(Tetradecyloxy)-2-chlorophenoxy]hydroxyphosphinyl]oxy]phenyl]
methyl]pyridinium, hydroxide, inner salt
1-[4-[[[4-(Dodecyloxy)-2-methylphenoxy]hydroxyphosphinyl]oxy]phenyl]
methyl]quinolinium, hydroxide, inner salt
1-[4-[[[4-(Dodecyloxy)-2-methoxyphenoxy]hydroxyphosphinyl]oxy]phenyl]
methyl]quinolinium, hydroxide, inner salt
1-[4-[[[4-(Dodecyloxy)-2-nitrophenoxy]hydroxyphosphinyl]oxy]phenyl]
methyl]quinolinium, hydroxide, inner salt
1-[4-[[[4-(Dodecyloxy)-2-carbomethoxyphenoxy]hydroxyphosphinyl]oxy]phenyl]
methyl]quinolinium, hydroxide, inner salt
1-[4-[[[4-(Dodecyloxy)-2,5-di-t-butylphenoxy]hydroxyphosphinyl]oxy]phenyl]
methyl]quinolinium, hydroxide, inner salt
1-[4-[[[4-(Dodecyloxy)-2,5-dichlorophenoxy]hydroxyphosphinyl]oxy]phenyl]

TABLE II-continued methyl]quinolinium, hydroxide, inner salt
1-[4-[[[4-(Dodecyloxy)-2-chlorophenoxy]hydroxyphosphinyl]oxy]phenyl] methyl]quinolinium, hydroxide, inner salt
3-[[3-[[[[6-(Dodecyloxy)-2-naphthalenyl]oxy]hydroxyphosphinyl]oxy]phenyl] methyl]thiazolium, hydroxide, inner salt
3-[[3-[[[[4-(Dodecyloxy)-1-naphthalenyl]oxy]hydroxyphosphinyl]oxy]phenyl] methyl]thiazolium, hydroxide, inner salt
3-[[3-[[[[3-(Dodecyloxy)-2-naphthalenyl]oxy]hydroxyphosphinyl]oxy]phenyl] methyl]thiazolium, hydroxide, inner salt
3-[[3-[[[15-(Dodecyloxy)-1-naphthalenyl]oxy]hydroxyphosphinyl]oxy]phenyl] methyl]thiazolium, hydroxide, inner salt
3-[[3-[[[[8-(Dodecyloxy)-1-naphthalenyl]oxy]hydroxyphosphinyl]oxy]phenyl] methyl]thiazolium, hydroxide, inner salt
3-[[3-[[[[7-(Tetradecyloxy)-2-naphthalenyl]oxy]hydroxyphosphinyl]oxy]phenyl] methyl]thiazolium, hydroxide, inner salt In addition to the utilities described hereinabove, many of the compounds of this invention are useful as precursors to other compounds of this invention.

We claim:

1. A method of treating a malady selected from the group consisting of asthma, anaphylactic and septic shock, adult respiratory distress, transplant rejection, thrombosis, stroke and cardiac anaphylaxis in a mammal which comprises administering to the mammal an effective amount of a compound of the formula:

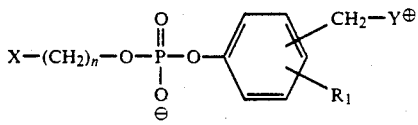

wherein:
X is a phenyl or naphthyl ring optionally substituted in any position with one to five substituents on the phenyl group and one to seven substituents to the naphthyl group of;
(i) —$R_2$, wherein $R_2$ is $C_1$–$C_{25}$ alkyl, $C_1$–$C_{25}$ alkenyl, $C_1$–$C_{25}$ alkoxy, $C_1$–$C_{25}$ thioalkyl, $C_1$–$C_{25}$ alkenyloxy, phenyl, phenoxy, substituted phenyl or substituted phenoxy wherein the substituents are $C_1$–$C_{20}$ alkyl, $C_1$–$C_{20}$ alkoxy, halogen or trifluoromethyl;
(ii) hydrogen, halogen, trifluoromethyl, cyano and nitro;
(iii) —$CO_2R_3$, —$CONHR_3$, —CHO, $OCONHR_3$, and —$NHCOR_3$ wherein $R_3$ is $C_1$–$C_{25}$ alkyl, $C_1$–$C_{25}$ alkenyl, phenyl or substituted phenyl wherein the substituents are $C_1$–$C_{20}$ alkyl, $C_1$–$C_{20}$ alkoxy, halogen or trifluoromethyl;
$R_1$ is one or more substituents of the aromatic ring which may be in any position and are hydrogen, $C_1$–$C_5$ alkyl, $C_1$–$C_5$ alkoxy or halogen;

—$CH_2$—Y is a single substituent of the aromatic ring which may occupy any position wherein Y is

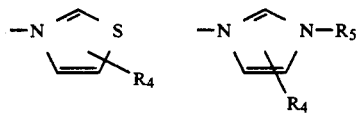

wherein $R_4$ represents one or more substituents of the heterocyclic ring which may occupy a non-hetero atom position and is $C_1$–$C_5$ alkyl, $C_1$–$C_5$ alkoxy, hydrogen or halogen; the moiety $R_5$ is $C_1$–$C_5$ alkyl or hydrogen and; n is the integer 0 to 1.

2. A method of claim 1 wherein n=0.

3. The method of claim 2 wherein $R_1$ is hydrogen.

4. A method of treating asthma in a mammal which comprises administering to the mammal an antiasthmatic amount of a compound of claim 1.

5. A method of treating anaphylactic and septic shock in a mammal which comprises administering to said mammal an effective amount of a compound of claim 1.

6. A method of treating adult respiratory distress syndrome in a mammal which comprises administering to the mammal an effective amount of a compound of claim 1.

7. A method of treating transplant rejection in a mammal which comprises administering to the mammal an effective amount of a compound of claim 1.

8. A method of treating thrombosis in a mammal which comprises administering to the mammal an effective amount of a compound of claim 1.

9. A method of treating stroke in a mammal which comprises administering to the mammal an effective amount of a compound of claim 1.

10. A method of treating cardiac anaphylaxis in a mammal which comprises administering to the mammal an effective amount of a compound of claim 1.

* * * * *